(12) United States Patent
Kottas et al.

(10) Patent No.: US 9,783,564 B2
(45) Date of Patent: Oct. 10, 2017

(54) ORGANIC ELECTROLUMINESCENT MATERIALS AND DEVICES

(75) Inventors: Gregg Kottas, Ewing, NJ (US); James Fiordeliso, Ewing, NJ (US); Bin Ma, Plainsboro, NJ (US); Chuanjun Xia, Lawrenceville, NJ (US); Scott Beers, Flemington, NJ (US); Jason Brooks, Philadelphia, PA (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 856 days.

(21) Appl. No.: 13/588,968

(22) Filed: Aug. 17, 2012

(65) Prior Publication Data

US 2013/0082245 A1     Apr. 4, 2013
US 2017/0240579 A9     Aug. 24, 2017

Related U.S. Application Data

(60) Provisional application No. 61/511,385, filed on Jul. 25, 2011, provisional application No. 61/541,769, filed on Sep. 30, 2011.

(30) Foreign Application Priority Data

Jul. 24, 2012    (EP) .................................... 12177646

(51) Int. Cl.
*H01L 51/54*     (2006.01)
*C09K 11/06*     (2006.01)
(Continued)

(52) U.S. Cl.
CPC .......... *C07F 15/0086* (2013.01); *C09K 11/06* (2013.01); *H01L 51/0087* (2013.01);
(Continued)

(58) Field of Classification Search
None
See application file for complete search history.

(56) References Cited

U.S. PATENT DOCUMENTS 4,769,292 A    9/1988    Tang et al.
5,061,569 A    10/1991   VanSlyke et al.
(Continued)

FOREIGN PATENT DOCUMENTS

EP    0650955       5/1995
EP    1683804 A2    7/2006
(Continued)

OTHER PUBLICATIONS

Baldo et al., "Highly Efficient Phosphorescent Emission from Organic Electroluminescent Devices," Nature, vol. 395, 151-154, (1998).
(Continued)

*Primary Examiner* — Marie R. Yamnitzky
(74) *Attorney, Agent, or Firm* — Duane Morris LLP

(57) ABSTRACT

Novel phosphorescent tetradentate platinum compounds of Formula I are provided. The complexes contain a dibenzo moiety, which allows for the creation of OLED devices with improved properties when compounds of Formula I are incorporated into such devices. Compounds of Formula I' that comprise two ligands that contain a 5-membered carbocyclic or heterocyclic ring, one of which contains an imidazole ring with a twisted aryl group attached to N-1 and a second aromatic ring that is attached to the platinum via a carbon atom. These compounds may be advantageously used in OLEDs.

20 Claims, 4 Drawing Sheets

Formula I

(51) Int. Cl.
*C07F 15/00* (2006.01)
*H05B 33/10* (2006.01)
*H01L 51/50* (2006.01)
*H01L 51/00* (2006.01)

(52) U.S. Cl.
CPC ...... *H05B 33/10* (2013.01); *C09K 2211/1007* (2013.01); *C09K 2211/1014* (2013.01); *C09K 2211/1029* (2013.01); *C09K 2211/1044* (2013.01); *C09K 2211/185* (2013.01); *H01L 51/0067* (2013.01); *H01L 51/5012* (2013.01); *H01L 51/5016* (2013.01)

(56) References Cited

U.S. PATENT DOCUMENTS

| | | |
|---|---|---|
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,442,797 B2 | 10/2008 | Itoh et al. |
| 7,445,855 B2 | 11/2008 | Mackenzie et al. |
| 7,501,190 B2 | 3/2009 | Ise |
| 7,534,505 B2 | 5/2009 | Lin et al. |
| 7,566,505 B2 | 7/2009 | Ise et al. |
| 7,579,093 B2 * | 8/2009 | Sano .................. C09K 11/06 257/E51.044 |
| 7,655,323 B2 | 2/2010 | Walters et al. |
| 7,771,845 B2 | 8/2010 | Sano et al. |
| 7,781,074 B2 | 8/2010 | Sano et al. |
| 8,263,236 B2 * | 9/2012 | Kinoshita et al. ............ 428/690 |
| 8,710,235 B2 * | 4/2014 | Kinoshita et al. ............ 548/103 |
| 2002/0034656 A1 | 3/2002 | Thompson et al. |
| 2002/0125818 A1 | 9/2002 | Sato et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0227112 A1 | 10/2005 | Ise et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0073359 A1 | 4/2006 | Ise et al. |
| 2006/0134460 A1 | 6/2006 | Kondakova et al. |
| 2006/0134461 A1 | 6/2006 | Huo et al. |
| 2006/0202194 A1 | 9/2006 | Jeong et al. |
| 2006/0202197 A1 | 9/2006 | Nakayama et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0059552 A1 | 3/2007 | Takeda et al. |
| 2007/0103060 A1 | 5/2007 | Itoh et al. |
| 2007/0190359 A1 | 8/2007 | Knowles et al. |
| 2007/0278938 A1 | 12/2007 | Yabunouchi et al. |
| 2008/0001530 A1 | 1/2008 | Ise et al. |
| 2008/0015355 A1 | 1/2008 | Schafer et al. |
| 2008/0018221 A1 | 1/2008 | Egen et al. |
| 2008/0036373 A1 | 2/2008 | Itoh et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0241589 A1 * | 10/2008 | Fukunaga et al. ............ 428/690 |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0079340 A1 * | 3/2009 | Kinoshita et al. ............ 313/504 |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0128008 A1 | 5/2009 | Ise et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2009/0267500 A1 | 10/2009 | Kinoshita et al. |
| 2011/0049496 A1 | 3/2011 | Fukuzaki |
| 2011/0073848 A1 | 3/2011 | Takada et al. |
| 2012/0302753 A1 | 11/2012 | Li et al. |

FOREIGN PATENT DOCUMENTS

| | | |
|---|---|---|
| EP | 1725079 | 11/2006 |
| EP | 2034538 | 3/2009 |
| EP | 2123640 | 11/2009 |
| EP | 2177646 | 4/2010 |
| JP | 200511610 | 1/2005 |
| JP | 2007123392 | 5/2007 |
| JP | 2007254297 | 10/2007 |
| JP | 2008074939 | 4/2008 |
| JP | 2009096800 | 5/2009 |
| JP | 2009231516 | 10/2009 |
| JP | 2009266943 | 11/2009 |
| JP | 2009267171 | 11/2009 |
| JP | 2009267244 | 11/2009 |
| JP | 2011054695 | 3/2011 |
| JP | 2011089103 | 5/2011 |
| JP | 2011213674 | 10/2011 |
| JP | 2011213918 | 10/2011 |
| TW | 201038563 | 11/2010 |
| TW | 201307365 | 2/2013 |
| WO | WO 0139234 | 5/2001 |
| WO | WO 0202714 | 1/2002 |
| WO | WO 0215645 | 2/2002 |
| WO | WO 03040257 | 5/2003 |
| WO | WO 03060956 | 7/2003 |
| WO | WO 2004093207 | 10/2004 |
| WO | WO 2004/108857 | 12/2004 |
| WO | WO 2004107822 | 12/2004 |
| WO | WO 2005014551 | 2/2005 |
| WO | WO 2005019373 | 3/2005 |
| WO | WO 2005030900 | 4/2005 |
| WO | WO 2005089025 | 9/2005 |
| WO | WO 2005123873 | 12/2005 |
| WO | WO 2006009024 | 1/2006 |
| WO | WO 2006056418 | 6/2006 |
| WO | WO 2006072002 | 7/2006 |
| WO | WO 2006082742 | 8/2006 |

(56) References Cited

FOREIGN PATENT DOCUMENTS

| | | |
|---|---|---|
| WO | WO 2006098120 | 9/2006 |
| WO | WO 2006100298 | 9/2006 |
| WO | WO 2006103874 | 10/2006 |
| WO | WO 2006114966 | 11/2006 |
| WO | WO 2006132173 | 12/2006 |
| WO | WO 2007002683 | 1/2007 |
| WO | WO 2007004380 | 1/2007 |
| WO | WO 2007063754 | 6/2007 |
| WO | WO 2007063796 | 6/2007 |
| WO | WO 2008056746 | 5/2008 |
| WO | WO 2008101842 | 8/2008 |
| WO | WO 2008132085 | 11/2008 |
| WO | WO 2009000673 | 12/2008 |
| WO | WO 2009003898 | 1/2009 |
| WO | WO 2009008311 | 1/2009 |
| WO | 2009021126 A2 | 2/2009 |
| WO | WO 2009018009 | 2/2009 |
| WO | WO 2009021126 | 2/2009 |
| WO | WO 2009050290 | 4/2009 |
| WO | WO 2009062578 | 5/2009 |
| WO | WO 2009063833 | 5/2009 |
| WO | WO 2009066778 | 5/2009 |
| WO | WO 2009066779 | 5/2009 |
| WO | WO 2009086028 | 7/2009 |
| WO | WO 2009100991 | 8/2009 |
| WO | WO 2010/118026 | 10/2010 |
| WO | 2011013628 A1 | 2/2011 |

OTHER PUBLICATIONS

Baldo et al., "Very high-efficiency green organic light-emitting devices based on electrophosphorescence," Appl. Phys. Lett., vol. 75, No. 1, 4-6 (1999).
U.S. Appl. No. 61/541,769, filed Sep. 30, 2011.
U.S. Appl. No. 61/511,385, filed Jul. 25, 2011.
U.S. Appl. No. 61/445,864, filed Feb. 23, 2011.
Search Report corresponding to European patent application No. EP 12177646, (dated Nov. 20, 2012).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Tung, Yung-Liang et al., "Organic Light-Emitting Diodes Based on Charge-Neutral $Ru^{II}$ PHosphorescent Emitters," Adv. Mater., 17(8):1059-1064 (2005).
Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).
Wong, Wai-Yeung, "Multifunctional Iridium Complexes Based on Carbazole Modules as Highly Efficient Electrophosphors," Angew. Chem. Int. Ed., 45:7800-7803 (2006).
Tang, C.W. and VanSLYKE, S.A., "Organic Electroluminescent Diodes," Appl. Phys. Lett., 51(12):913-915 (1987).
Adachi, Chihaya et al., "Organic Electroluminescent Device Having a Hole Conductor as an Emitting Layer," Appl. Phys. Lett., 55(15):1489-1491 (1989).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Gao, Zhiqiang et al., "Bright-Blue Electroluminescence From a Silyl-Substituted ter-(phenylene-vinylene) derivative," Appl. Phys. Lett., 74(6):865-867 (1999).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Hung, L.S. et al., "Anode Modification in Organic Light-Emitting Diodes by Low-Frequency Plasma Polymerization of $CHF_3$," Appl. Phys. Lett., 78(5):673-675 (2001).
Ikai, Masamichi et al., "Highly Efficient Phosphorescence From Organic Light-Emitting Devices with an Exciton-Block Layer," Appl. Phys. Lett., 79(2):156-158 (2001).
Wang, Y. et al., "Highly Efficient Electroluminescent Materials Based on Fluorinated Organometallic Iridium Compounds," Appl. Phys. Lett., 79(4):449-451 (2001).
Kwong, Raymond C. et al., "High Operational Stability of Electrophosphorescent Devices," Appl. Phys. Lett., 81(1):162-164 (2002).
Holmes, R.J. et al., "Blue Organic Electrophosphorescence Using Exothermic Host-Guest Energy Transfer," Appl. Phys. Lett., 82(15):2422-2424 (2003).
Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).
Okumoto, Kenji et al., "Green Fluorescent Organic Light-Emitting Device with External Quantum Efficiency of Nearly 10%," Appl. Phys. Lett., 89:063504-1-063504-3 (2006).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Aonuma, Masaki et al., "Material Design of Hole Transport Materials Capable of Thick-Film Formation in Organic Light Emitting Diodes," Appl. Phys. Lett., 90:183503-1-183503-3 (2007).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
Adachi, Chihaya et al., "High-Efficiency Red Electrophosphorescence Devices," Appl. Phys. Lett., 78(11):1622-1624 (2001).
Wong, Keith Man-Chung et al.,"A Novel Class of Phosphorescent Gold(III) Alkynyl-Based Organic Light-Emitting Devices with Tunable Colour," Chem. Commun., 2906-2908 (2005).
Hamada, Yuji et al., "High Luminance in Organic Electroluminescent Devices with Bis(10-hydroxybenzo[h]quinolinato)beryllium as an Emitter," Chem. Lett., 905-906 (1993).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4):592-593 (2005).
Mi, Bao-Xiu et al., "Thermally Stable Hole-Transporting Material for Organic Light-Emitting Diode: an Isoindole Derivative," Chem. Mater., 15(16):3148-3151 (2003).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Niu, Yu-Hua et al., "Highly Efficient Electrophosphorescent Devices with Saturated Red Emission from a Neutral Osmium Complex," Chem. Mater., 17(13):3532-3536 (2005).
Lo, Shih-Chun et al., "Blue Phosphorescence from Iridium(III) Complexes at Room Temperature," Chem. Mater., 18(21):5119-5129 (2006).
Takizawa, Shin-ya et al., "Phosphorescent Iridium Complexes Based on 2-Phenylimidazo[1,2- α]pyridine Ligands: Tuning of Emission Color toward the Blue Region and Application to Polymer Light-Emitting Devices," Inorg. Chem., 46(10):4308-4319 (2007).
Lamansky, Sergey et al., "Synthesis and Characterization of Phosphorescent Cyclometalated Iridium Complexes," Inorg. Chem., 40(7):1704-1711 (2001).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Noda, Tetsuya and Shirota,Yasuhiko, "5,5'-Bis(dimesitylboryl)-2,2'-bithiophene and 5,5"-Bis(dimesitylboryl)-2,2':5',2"-terthiophene as a Novel Family of Electron-Transporting Amorphous Molecular Materials," J. Am. Chem. Soc., 120 (37):9714-9715 (1998).

(56) References Cited

OTHER PUBLICATIONS

Sakamoto, Youichi et al., "Synthesis, Characterization, and Electron-Transport Property of Perfluorinated Phenylene Dendrimers," *J. Am. Chem. Soc.*, 122(8):1832-1833 (2000).

Adachi, Chihaya et al., "Nearly 100% Internal Phosphorescence Efficiency in an Organic Light Emitting Device," *J. Appl. Phys.*, 90(10):5048-5051 (2001).

Shirota, Yasuhiko et al., "Starburst Molecules Based on π-Electron Systems as Materials for Organic Electroluminescent Devices," *Journal of Luminescence*, 72-74:985-991 (1997).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).

Kido, Junji et al.,"1,2,4-Triazole Derivative as an Electron Transport Layer in Organic Electroluminescent Devices," *Jpn. J. Appl. Phys.*, 32:L917-L920 (1993).

Van Slyke, S. A. et al., "Organic Electroluminescent Devices with Improved Stability," *Appl. Phys. Lett.*, 69(15):2160-2162 (1996).

Guo, Tzung-Fang et al., "Highly Efficient Electrophosphorescent Polymer Light-Emitting Devices," *Organic Electronics*, 1:15-20 (2000).

Palilis, Leonidas C., "High Efficiency Molecular Organic Light-Emitting Diodes Based on Silole Derivatives and Their Exciplexes," *Organic Electronics*, 4:113-121 (2003).

Ikeda, Hisao et al., "P-185: Low-Drive-Voltage OLEDs with a Buffer Layer Having Molybdenum Oxide," *SID Symposium Digest*, 37:923-926 (2006).

T. Östergård et al., "Langmuir-Blodgett Light-Emitting Diodes of Poly(3-Hexylthiophene): Electro-Optical Characteristics Related to Structure," *Synthetic Metals*, 87:171-177 (1997).

Hu, Nan-Xing et al., "Novel High $T_g$ Hole-Transport Molecules Based on Indolo[3,2-b]carbazoles for Organic Light-Emitting Devices," *Synthetic Metals*, 111-112:421-424 (2000).

Salbeck, J. et al., "Low Molecular Organic Glasses for Blue Electroluminescence," *Synthetic Metals*, 91:209-215 (1997).

Chinese Patent Office, Notification of the First Office Action and English Version of Chinese Office Action regarding corresponding Chinese Application No. 201210258961.3 issued Apr. 17, 2015, pp. 1-14.

Chinese Patent Office, International Search Report regarding corresponding Chinese Application No. 201210258961.3 issued Apr. 17, 2015, pp. 1-4.

Chinese Patent Office, Notification of the First Office Action and English Version of Chinese Office Action regarding corresponding Chinese Application No. 201210375323.X issued Jun. 30, 2015, pp. 1-12.

Chinese Patent Office, International Search Report regarding corresponding Chinese Application No. 201210375323.X issued Jun. 30, 2015, pp. 1-4. 201210375323.X.

Search Report issued on Apr. 25, 2016 for corresponding Taiwanese Patent Application No. 101126680.

Office Action dated Jun. 15, 2015 for corresponding Taiwan Patent Application No. 101126680.

Notice of Reasons for Rejection dated Sep. 14, 2015 for corresponding JP Patent Application No. 2012-163363.

\* cited by examiner

Formula I

Formula I'

ORGANIC ELECTROLUMINESCENT MATERIALS AND DEVICES

CROSS-REFERENCES TO RELATED APPLICATIONS

This application claims priority to U.S. Application Ser. No. 61/511,385, filed Jul. 25, 2011, to U.S. Application Ser. No. 61/541,769, filed Sep. 30, 2011, and to European Application No. 12177646.2 filed Jul. 24, 2012, the disclosures of which are herein expressly incorporated by reference in their entirety.

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to compounds suitable for incorporation into OLED devices, specifically the compounds comprise tetradentate platinum complexes. The compounds also comprise cyclometallated tetradentate Pt(II) complexes comprising two ligands that each contain at least one 5-membered carbocyclic or heterocyclic ring. One ligand comprises an imidazole ring with a twisted aryl group bonded to N–1 and an aromatic ring that is coordinated to the platinum via, a carbon atom.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

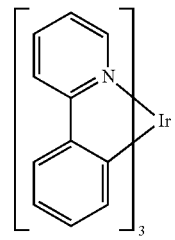

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

A compound having the formula:

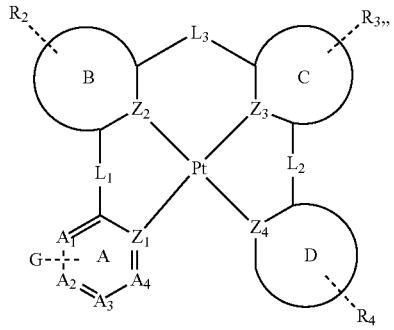

Formula I is provided, wherein G has the structure

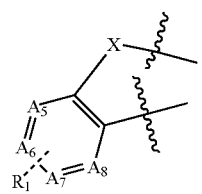

and wherein G is fused to any two adjacent carbon atoms on ring A. Ring B, ring C, and ring D are 5- or 6-membered carbocyclic or heterocyclic aromatic rings. $L_1$, $L_2$, and $L_3$ are independently selected from the group consisting of a single bond, BR, NR, PR, O, S, Se, C=O, S=O, $SO_2$, CRR', SiRR', and GeRR'. At least one of $L_1$, $L_2$, and $L_3$ is not a single bond, and X is selected from the group consisting of BR, NR, PR, O, S, Se, C=O, S=O, $SO_2$, CRR', SiRR', and GeRR'. $Z_1$, $Z_2$, $Z_3$, and $Z_4$ are nitrogen or carbon atoms, and $A_1$, $A_2$, $A_3$, $A_4$, $A_5$, $A_6$, $A_7$, and $A_8$ comprise carbon or nitrogen. $R_1$, $R_2$, $R_3$, and $R_4$ independently represent mono-, di-, tri-, or tetra-substitution, wherein $R_1$ is optionally fused, $R_2$ is optionally fused to ring B, $R_3$ is optionally fused to ring C, and $R_4$ is optionally fused to ring D. $R_3$ and $R_1$ are optionally linked to form a ring. If $L_2$ is not a single bond, $R_3$ and $L_2$ or $R_4$ and $L_2$ are optionally linked to form a ring. R, R', $R_1$, $R_2$, $R_3$, and $R_4$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one embodiment, the compound has a neutral charge. In one embodiment, at least two of $Z_1$, $Z_2$, $Z_3$, and $Z_4$ are nitrogen atoms. In another embodiment, at least two of $Z_1$, $Z_2$, $Z_3$, and $Z_4$ are carbon atoms.

In one embodiment, at least one of ring B, ring C, and ring D comprises a carbene ligand coordinated to Pt. In another embodiment, at least one of $Z_1$, $A_1$, $A_2$, $A_3$, $A_4$, $A_5$, $A_6$, $A_7$, and $A_8$ is a nitrogen atom.

In one embodiment, the compound has the formula:

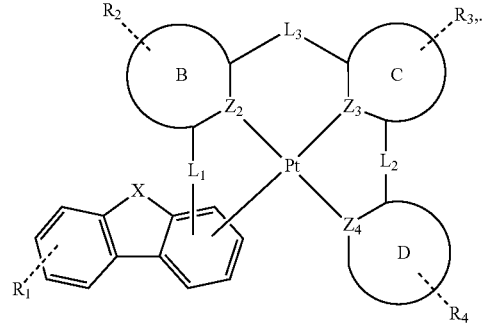

Formula II

In another embodiment, the compound has the formula:

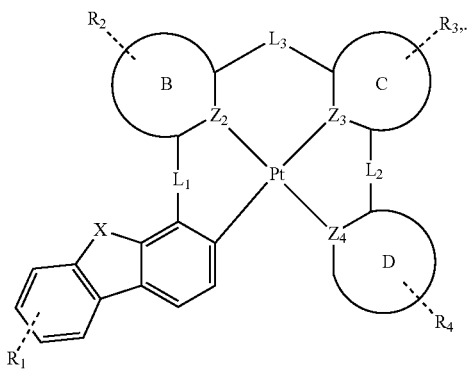

Formula III

In one embodiment, the compound has the formula:

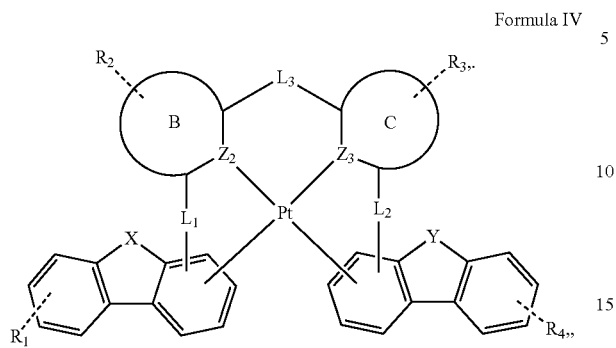

Formula IV wherein Y is selected from the group consisting of BR, NR, PR, O, S, Se, C=O, S=O, SO$_2$, CRR', SiRR', and GeRR'.

In another embodiment, the compound has the formula:

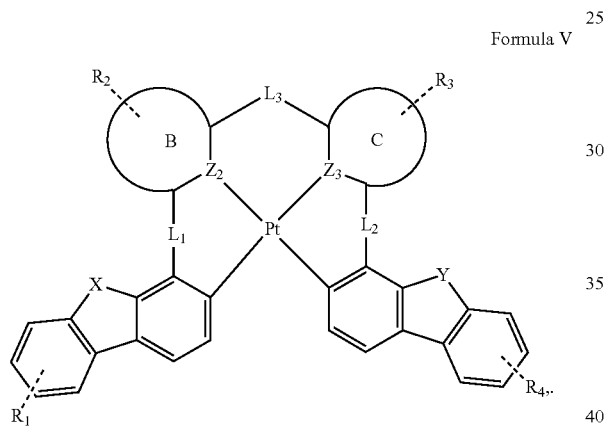

Formula V

In one embodiment, L$_1$ and L$_2$ are single bonds. In another embodiment, L$_3$ is independently selected from the group consisting of O, S, and NR. In another embodiment, L$_3$ is NR, and R is phenyl or substituted phenyl. In one embodiment, L$_3$ is O.

In one embodiment, Z$_2$ and Z$_3$ are nitrogen atoms. In another embodiment, Z$_2$ and Z$_4$ are nitrogen atoms. In one embodiment, X is independently selected from the group consisting of O, S, and NR. In one embodiment, X is O.

In one embodiment, the compound is selected from the group consisting of:

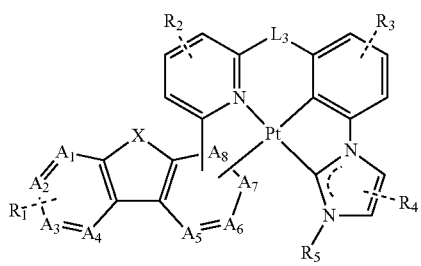

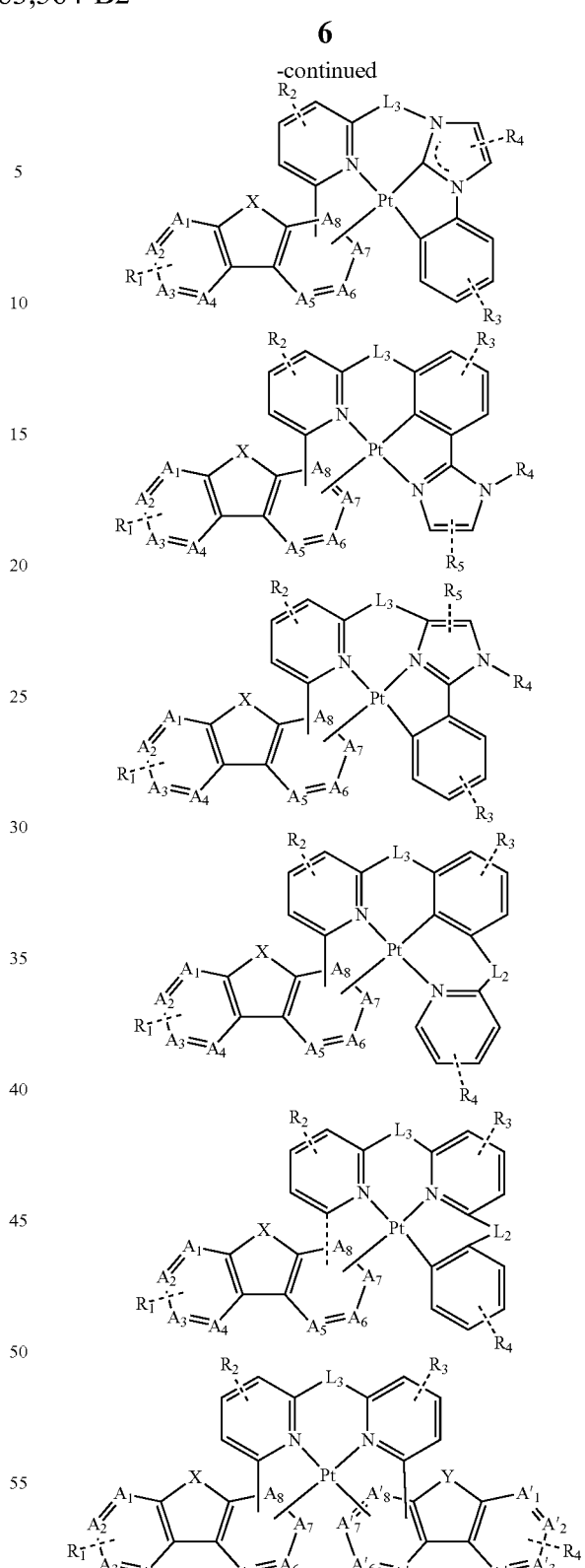

wherein Y is selected from the group consisting of BR, NR, PR, O, S, Se, C=O, S=O, SO$_2$, CRR', SiRR', and GeRR'. A$_1$', A$_2$', A$_3$', A$_4$', A$_5$', A$_6$', A$_7$', and A$_8$' comprise carbon or nitrogen. At most one of A$_1$, A$_2$, A$_3$, A$_4$ is nitrogen, and at most one of A$_1$', A$_2$', A$_3$', A$_4$' is nitrogen. At most one of A$_5$, A$_6$, A$_7$, A$_8$ is nitrogen, and the nitrogen is not bound to Pt. At most one of A$_5$', A$_6$', A$_7$', A$_8$' is nitrogen, and the nitrogen is not bound to Pt. The Pt forms at least two Pt—C bonds and $R_3$ and $R_4$ may be fused together to form a ring. $R_5$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

A first device is provided. The first device comprises a first organic light emitting device, further comprising an anode, a cathode, and an organic layer, disposed between the anode and the cathode, comprising a compound having the formula:

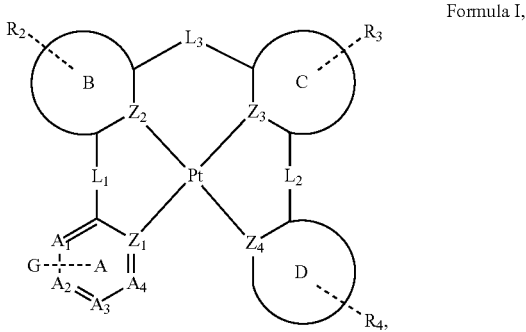

Formula I, is provided, wherein G has the structure

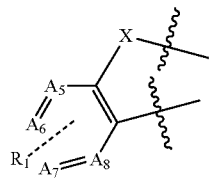

and wherein G is fused to any two adjacent carbon atoms on ring A. Ring B, ring C, and ring D are 5- or 6-membered carbocyclic or heterocyclic aromatic rings. $L_1$, $L_2$, and $L_3$ are independently selected from the group consisting of a single bond, BR, NR, PR, O, S, Se, C=O, S=O, $SO_2$, CRR', SiRR', and GeRR'. At least one of $L_1$, $L_2$, and $L_3$ is not a single bond, and X is selected from the group consisting of BR, NR, PR, O, S, Se, C=O, S=O, $SO_2$, CRR', SiRR', and GeRR'. $Z_1$, $Z_2$, $Z_3$, and $Z_4$ are nitrogen or carbon atoms, and $A_1$, $A_2$, $A_3$, $A_4$, $A_5$, $A_6$, $A_7$, and $A_8$ comprise carbon or nitrogen, $R_1$, $R_2$, $R_3$, and $R_4$ independently represent mono-, di-, tri-, or tetra-substitution, wherein $R_1$ is optionally fused, $R_2$ is optionally fused to ring B, $R_3$ is optionally fused to ring C, and $R_4$ is optionally fused to ring D. R, R', $R_1$, $R_2$, $R_3$, and $R_4$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one embodiment, the first device is a consumer product. In another embodiment, the first device is an organic light-emitting device, in one embodiment, the first device comprises a lighting panel. In one embodiment, the organic layer is an emissive layer and the compound is an emissive dopant. In another embodiment, the organic layer is an emissive layer and the compound is a non-emissive dopant.

In one embodiment, the organic layer further comprises a host. In another embodiment, the host comprises a triphenylene containing benzo-fused thiophene or benzo-fused furan, wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, CH=CH—$C_nH_{2n+1}$, C≡C$C_nH_{2n+1}$, $Ar_1$, $Ar_1$—$Ar_2$, $C_nH_{2n}$—$Ar_1$, or no substitution, wherein $Ar_1$ and $Ar_2$ are independently selected from the group consisting of benzene, biphenyl, naphthalene, triphenylene, carbazole, and heteroaromatic analogs thereof, and n is from 1 to 10.

In one embodiment, the host has the formula

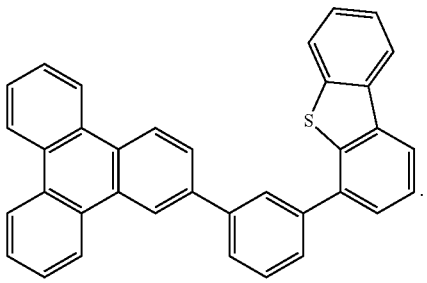 [SMILES: c1cc(-c2ccc3c4ccccc4c4ccccc4c3c2)cc(-c2cccc3c2sc2ccccc23)c1]

In another embodiment, the host is selected from the group consisting of

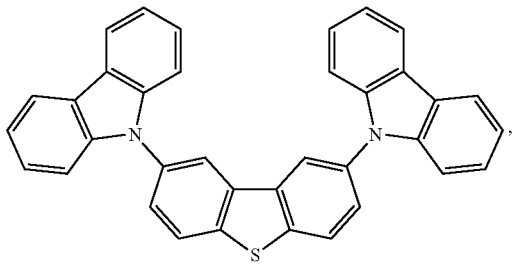

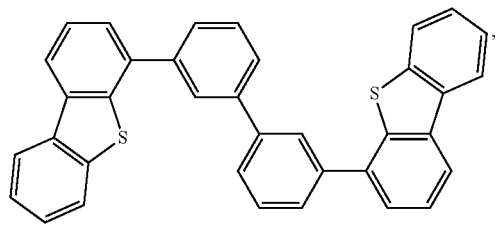

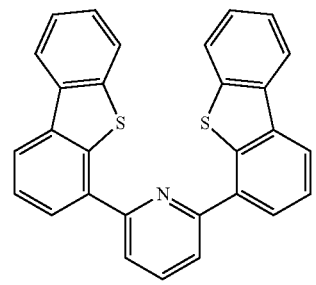

-continued

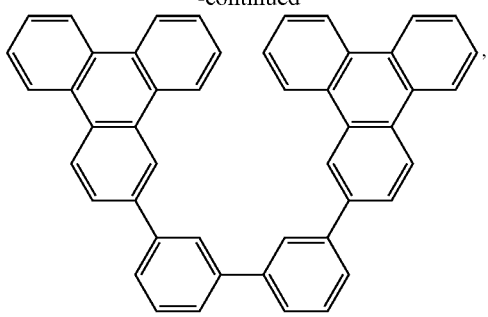

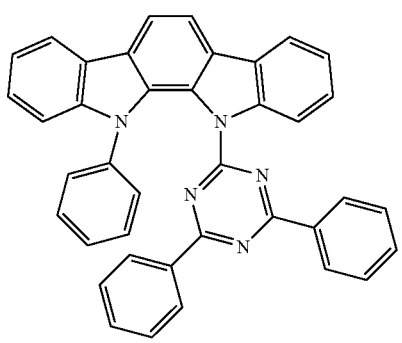

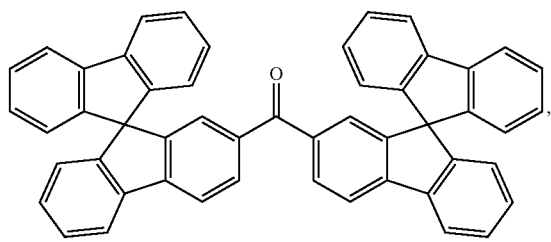

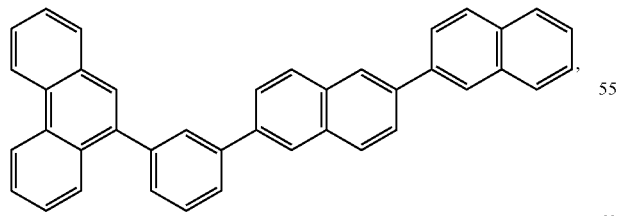

and combinations thereof.

In one embodiment, the host is a metal complex.

Cyclometallated tetradentate Pt(II) compounds comprising an imidazole ring with a twisted aryl group are provided. The compounds have the formula:

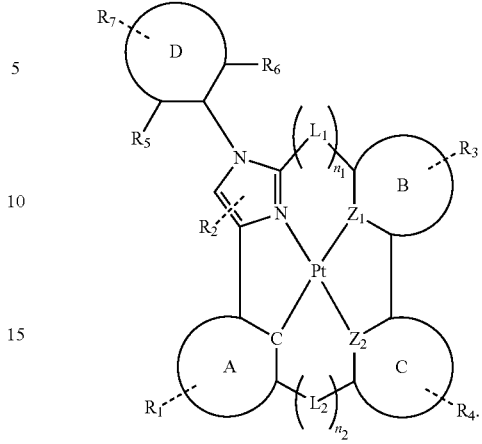

Formula I'

Ring A, ring B, ring C and ring D are each independently a 5- or 6-membered carbocyclic or heterocyclic ring. $L_1$ and $L_2$ are independently selected from the group consisting of a single bond, BR, NR, O, Se, C=O, S=O, $SO_2$, CRR', SiRR', and GeRR'. $n_1$ is 0 or 1. $n_2$ is 0 or 1, $n_1+n_2$ is at least equal to 1. $Z_1$ and $Z_2$ are independently a nitrogen atom or a carbon atom. $R_1$, $R_2$, $R_3$, $R_4$, and $R_7$ may represent mono-, di-, tri-, or tetra-substitutions. $R_1$ is optionally fused to ring A. $R_3$ is optionally fused to ring B. $R_4$ is optionally fused to ring C. $R_7$ is optionally fused to ring D. $R_3$ and $R_4$ are optionally joined to form into a ring. At least one of ring B and ring C is a 5-membered carbocyclic or heterocyclic ring. $R_1$, $R_2$, $R_3$, $R_4$, $R_5$, $R_6$, and $R_7$ are independently selected from the group consisting of hydrogen, deuterium, halide, alkyl, cycloalkyl, heteroalkyl, arylalkyl, alkoxy, aryloxy, amino, silyl, alkenyl, cycloakenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. At least one of $R_5$ and $R_6$ is not hydrogen or deuterium.

In one aspect, at least one of $R_5$ and $R_6$ is an alkyl in another aspect, at least one of $R_5$ and $R_6$ is an alkyl containing at least 3 carbons. In yet another aspect, at least one of $R_5$ and $R_6$ is a cycloalkyl.

In one aspect, each of $R_5$ and $R_6$ is an aryl.

In one aspect, $R_3$ or $R_4$ is a substituted aryl. In another aspect, $R_3$ or $R_4$ is a 2,6-disubstituted aryl.

Preferably, $R_3$ or $R_4$ is

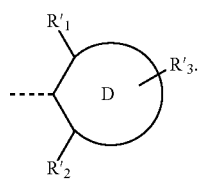

$R'_1$ and $R'_2$, are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. At least one of $R'_1$ and $R'_2$ is not hydrogen or deuterium. D is 5-membered or 6-membered carbocyclic or heterocyclic ring that is optionally further substituted with R'$_3$. R'$_3$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the compound has the formula:

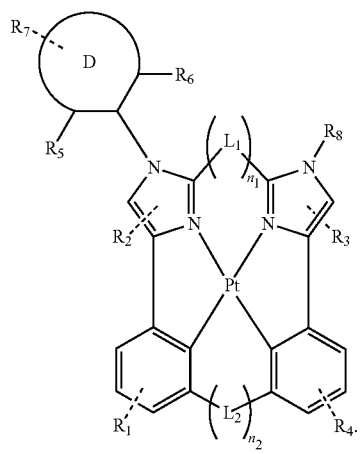

Formula II'

R$_8$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In another aspect, the compound has the formula:

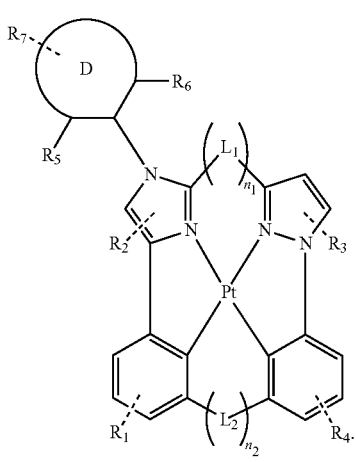

Formula III'

In yet another aspect, the compound has the formula:

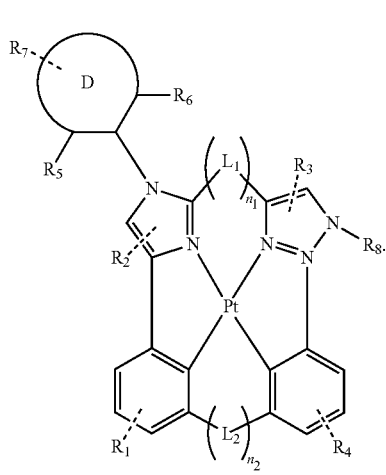

Formula IV'

R$_8$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In a further aspect, the compound has the formula:

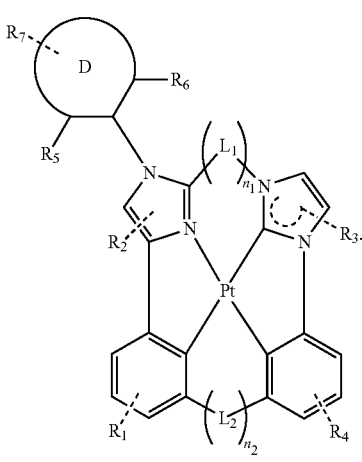

Formula V'

In another aspect, the compound has the formula:

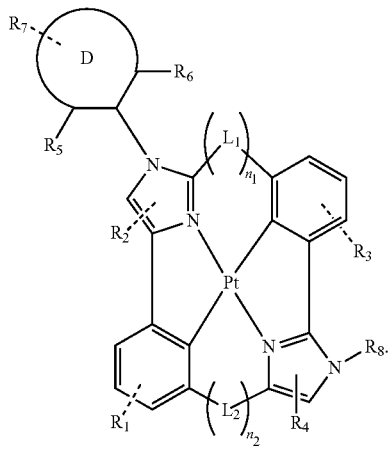

Formula VI'

$R_8$ is selected from the group consisting of hydrogen, deuterium, halide, alkyl, cycloalkyl, heteroalkyl, arylalkyl, alkoxy, aryloxy, amino, silyl, alkenyl, cycloakenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In yet another aspect, the compound has the formula:

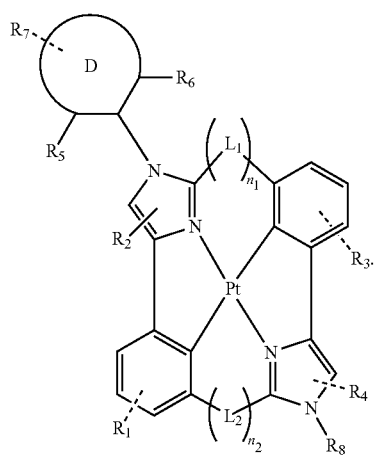

Formula VII'

$R_8$ is selected from the group consisting of hydrogen, deuterium, halide, alkyl, cycloalkyl, heteroalkyl, arylalkyl, alkoxy, aryloxy, amino, silyl, alkenyl, cycloakenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In another aspect, the compound has the formula:

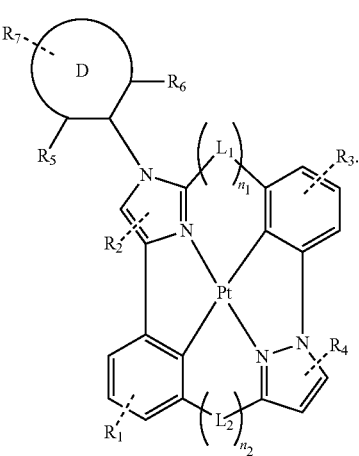

Formula VIII'

In yet another aspect, the compound had the formula:

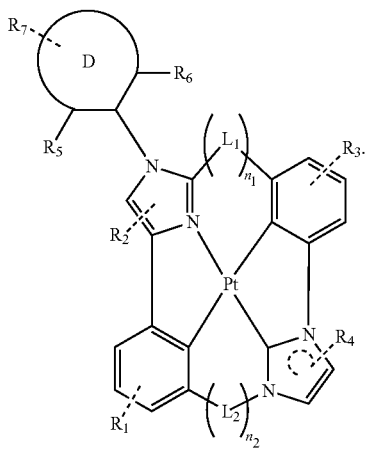

Formula IX'

Specific examples of cyclometallated tetradentate Pt(II) compounds comprising an imidazole ring with a twisted aryl group are provided. In one aspect, the compound is selected from the group consisting of:

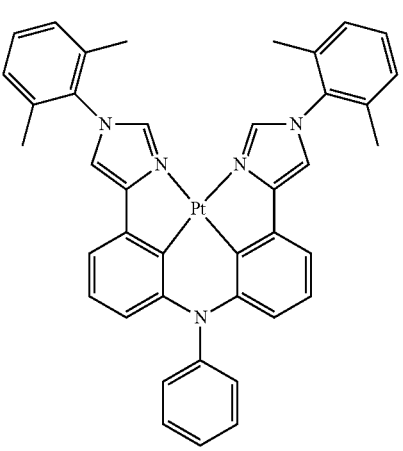

Compound 1'

Compound 2'
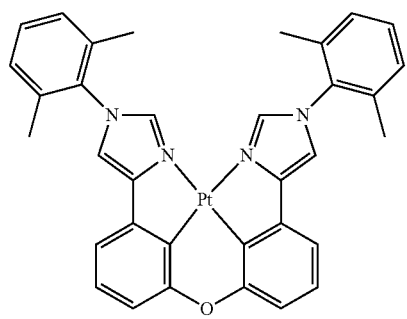
Compound 3'
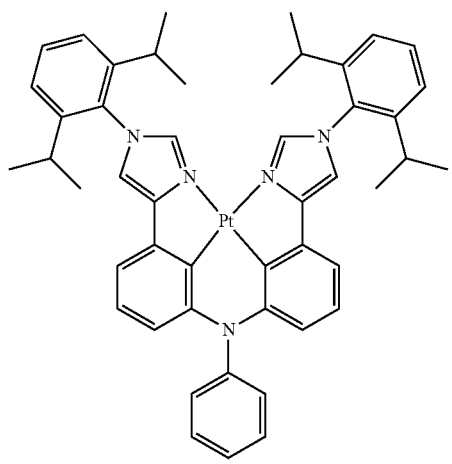
Compound 4'
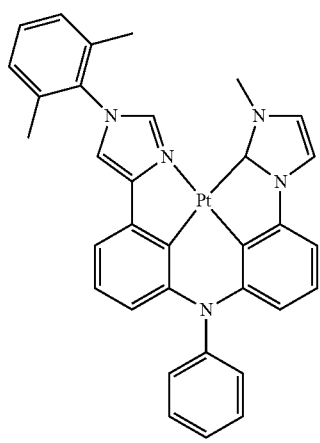
Compound 5'
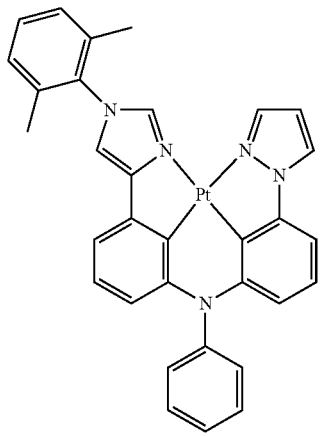
Compound 6'
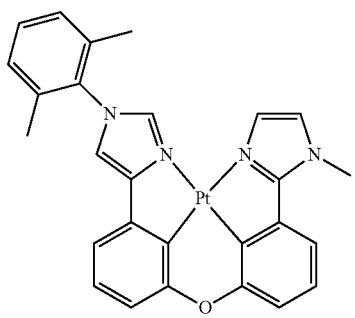
Compound 7'
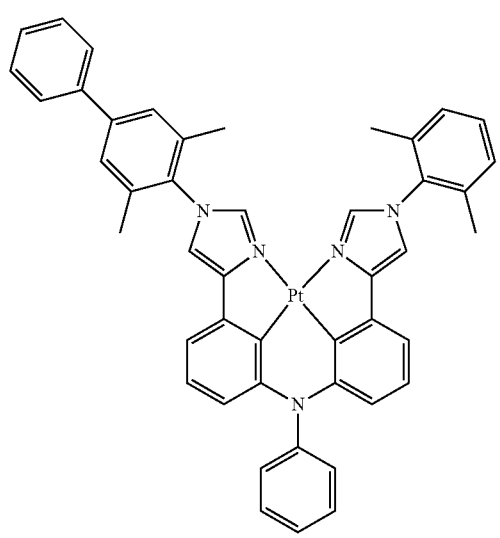

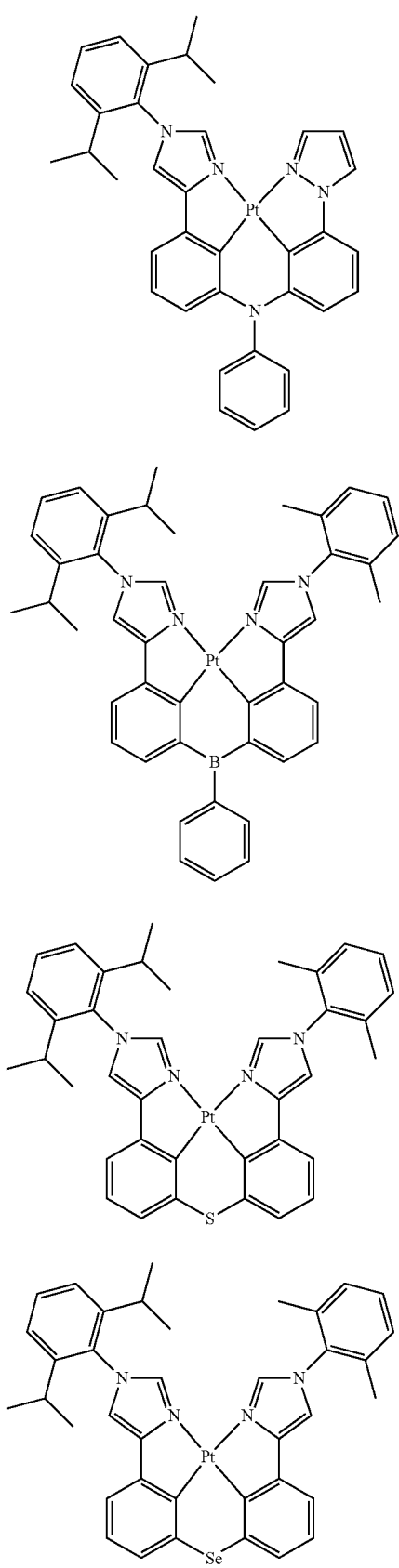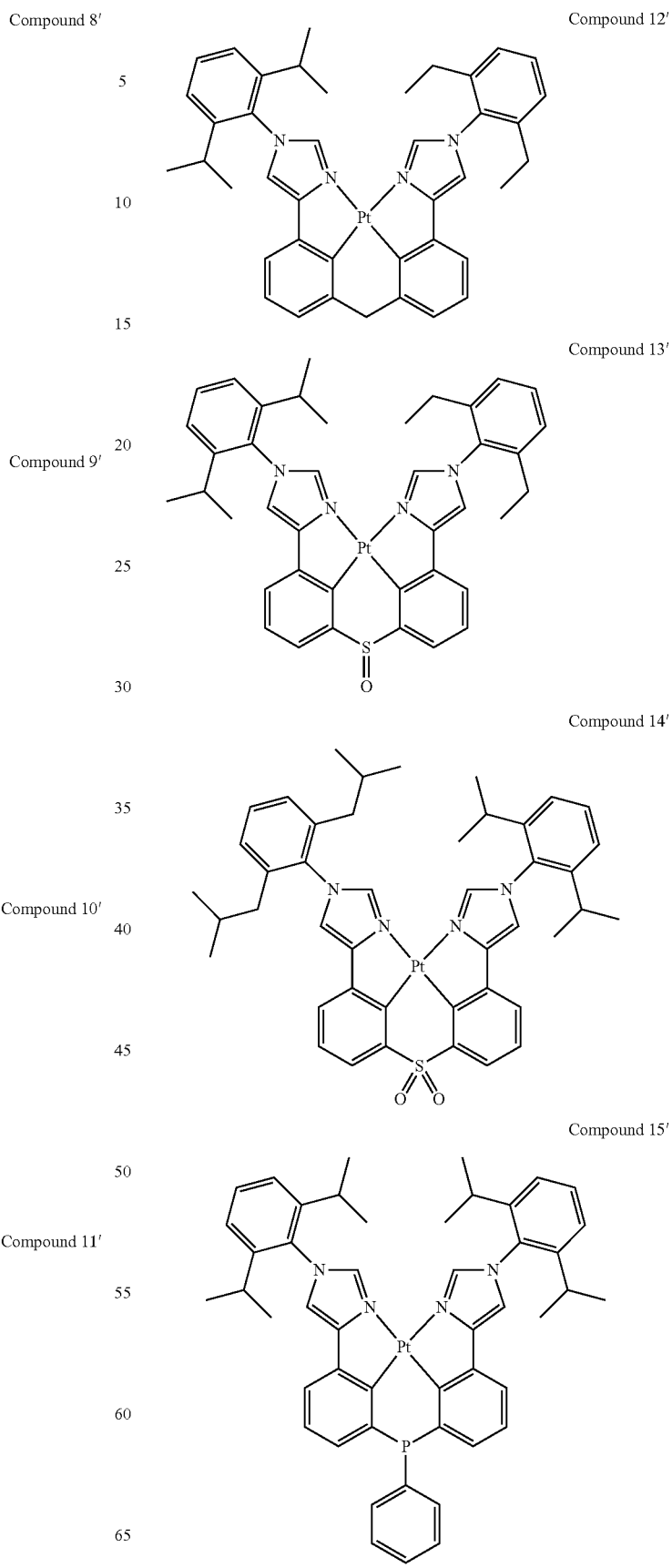

-continued
Compound 16'
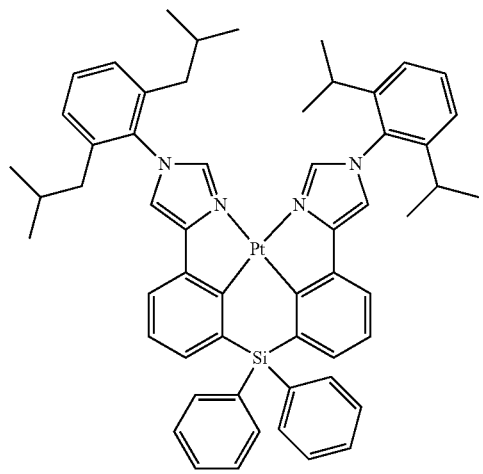
Compound 17'
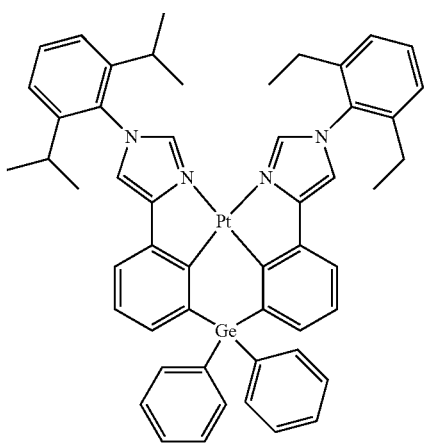
Compound 18'
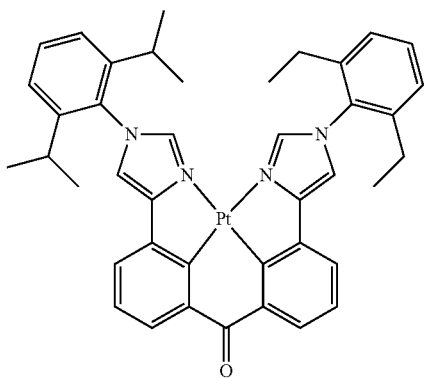
-continued
Compound 19'
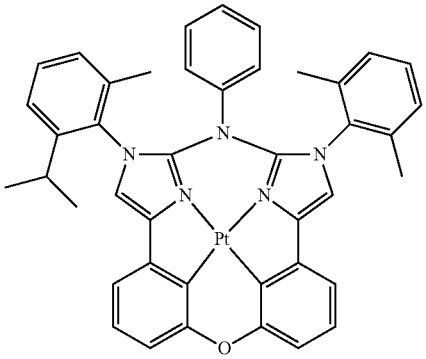
Compound 20'
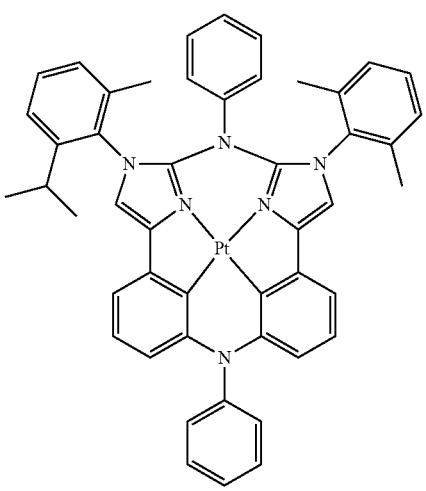
Compound 21'
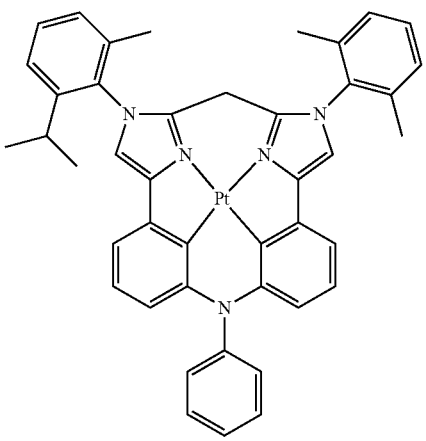

-continued
Compound 22'
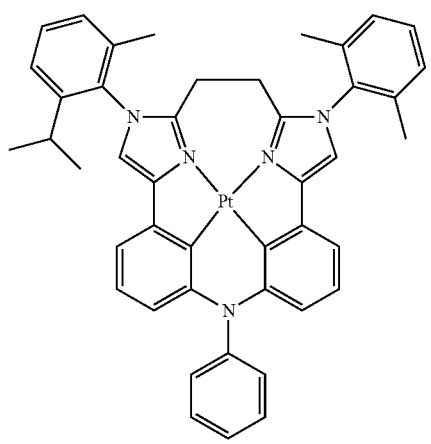
Compound 23'
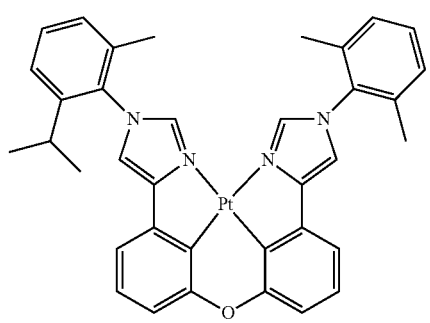
Compound 24'
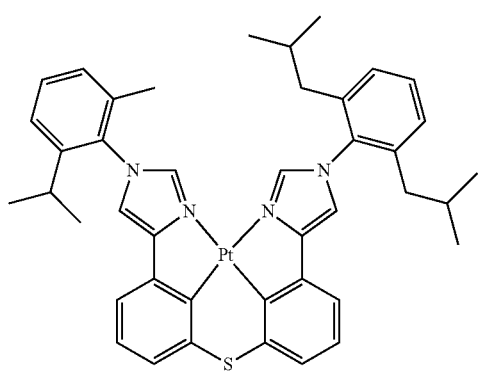
Compound 25'
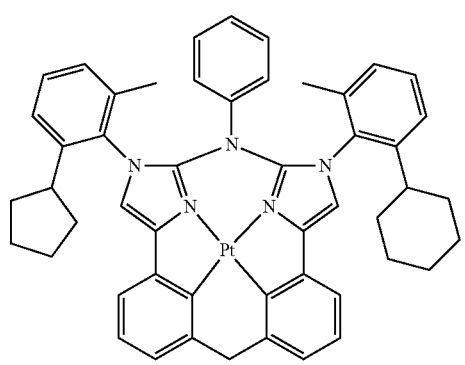
-continued
Compound 26'
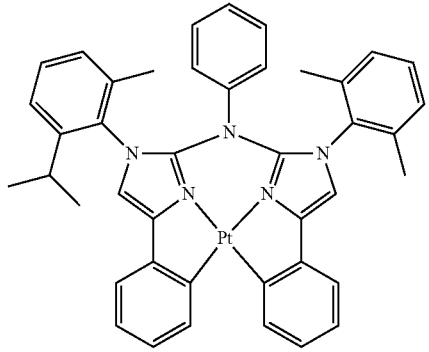
Compound 27'
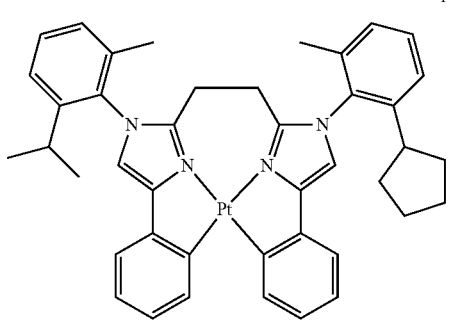
Compound 28'
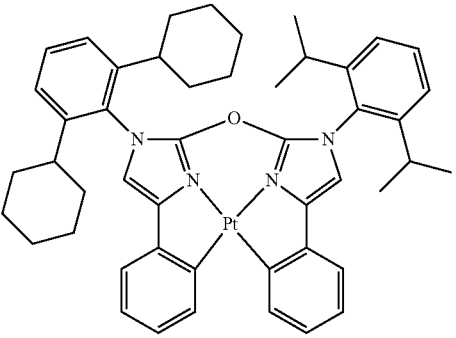
Compound 29'
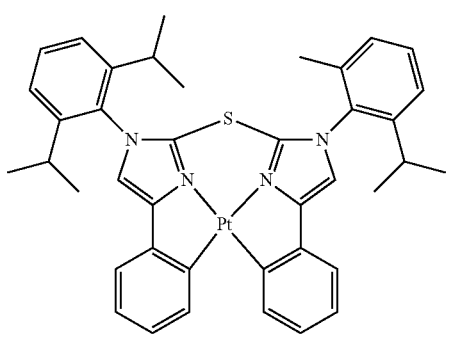

Compound 30'
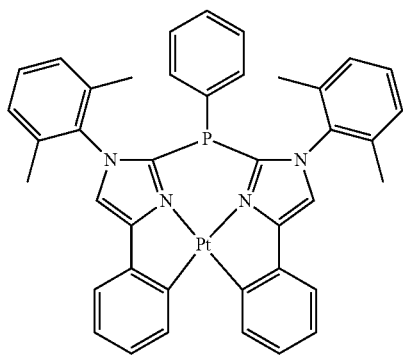
Compound 31'
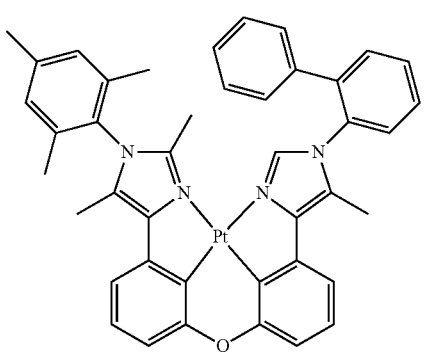
Compound 32'
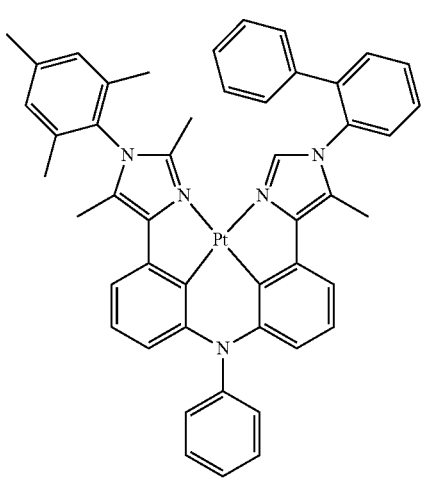
Compound 33'
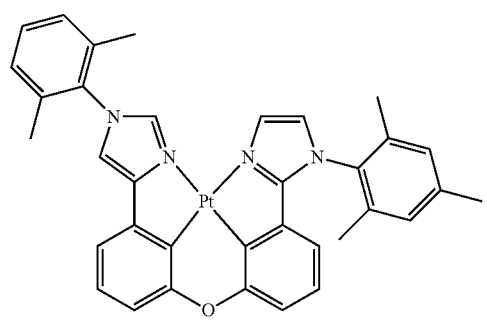
Compound 34'
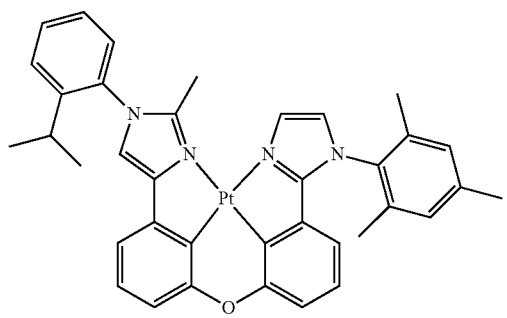
Compound 35'
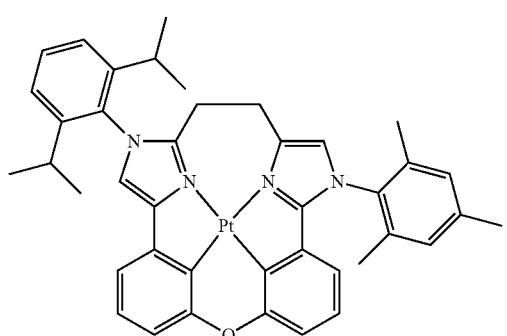
Compound 36'
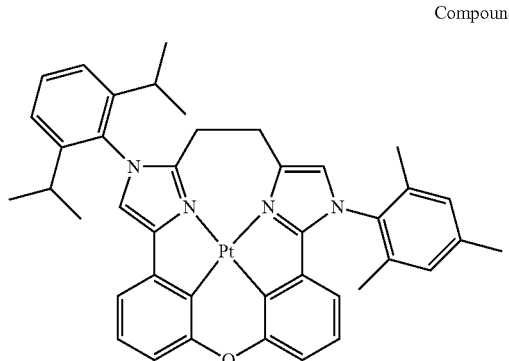
Compound 37'
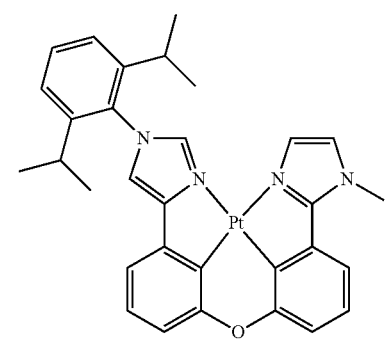

Compound 38'
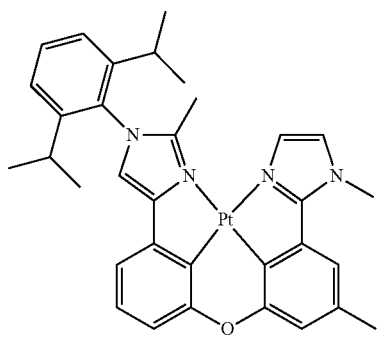
Compound 39'
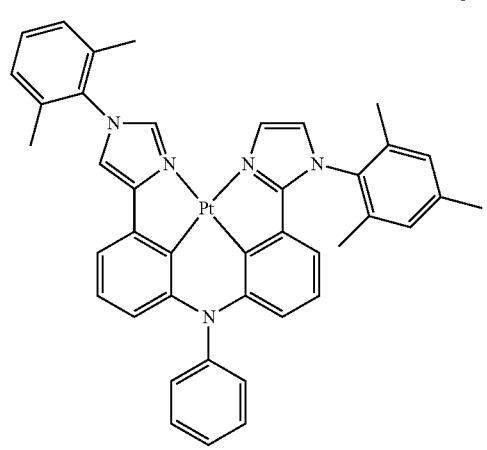
Compound 40'
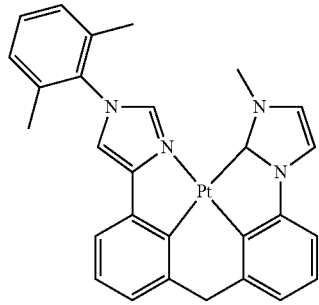
Compound 41'
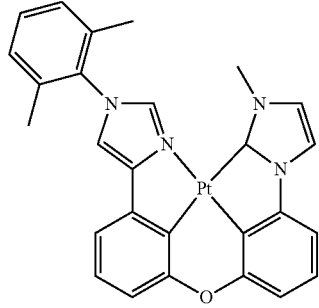
Compound 42'
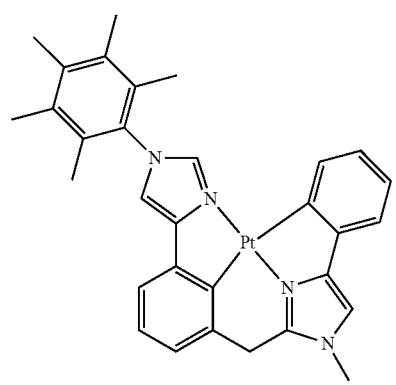
Compound 43'
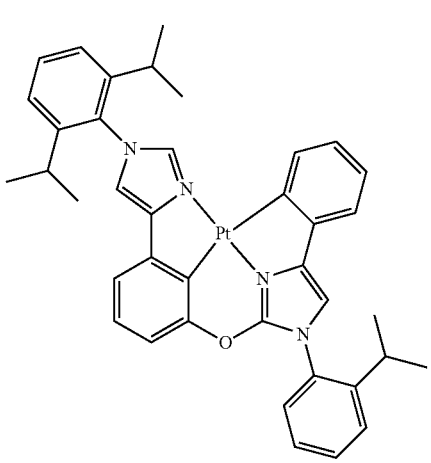
Compound 44'
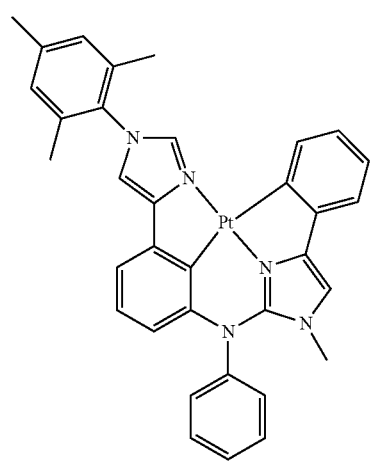
Compound 45'
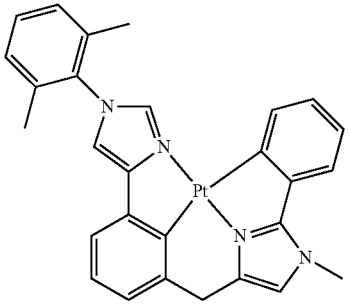

Compound 46'
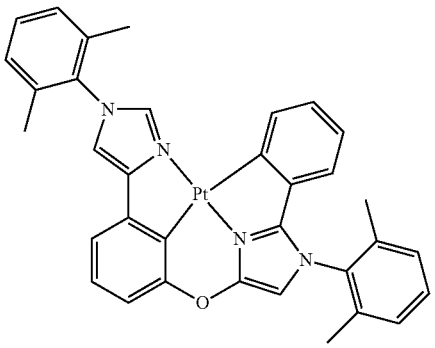
Compound 47'
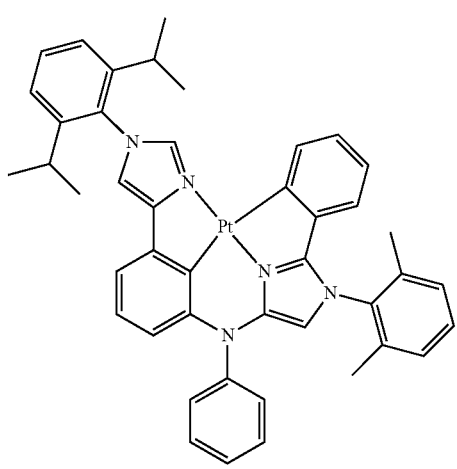
Compound 48'
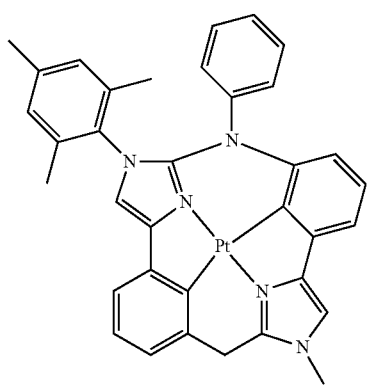
Compound 49'
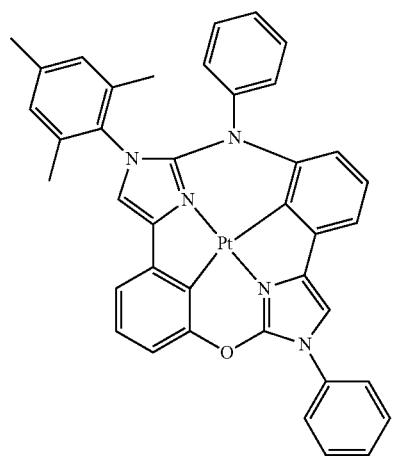
Compound 50'
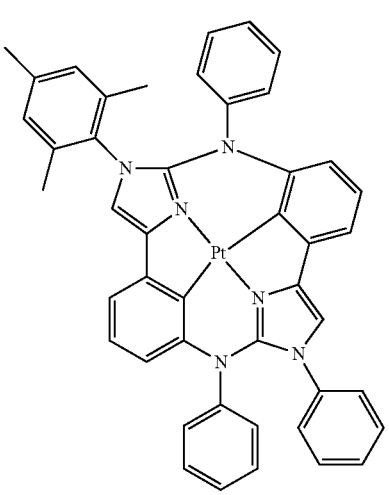
Compound 51'
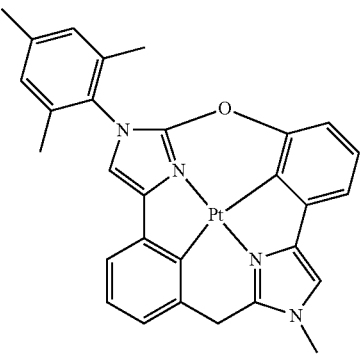
Compound 52'
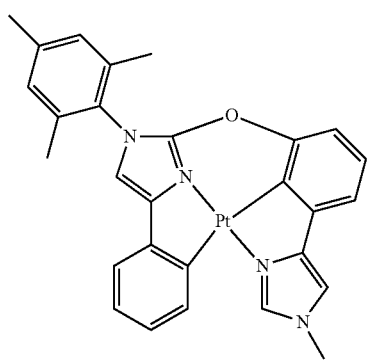

Compound 53'
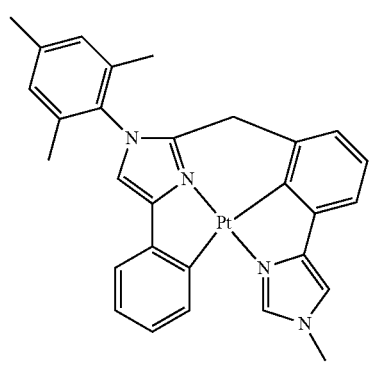
Compound 54'
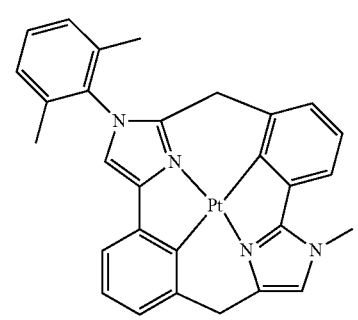
Compound 55'
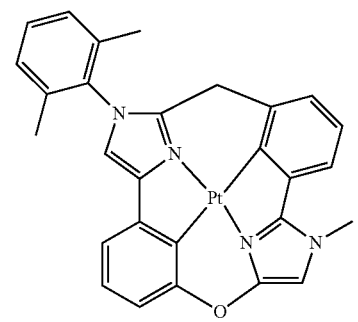
Compound 56'
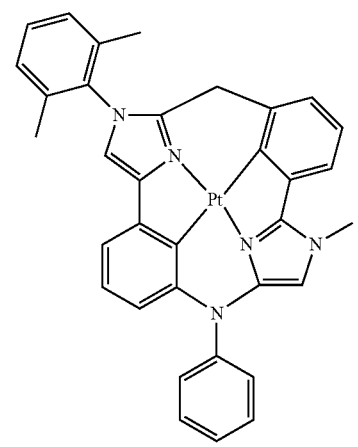
Compound 57'
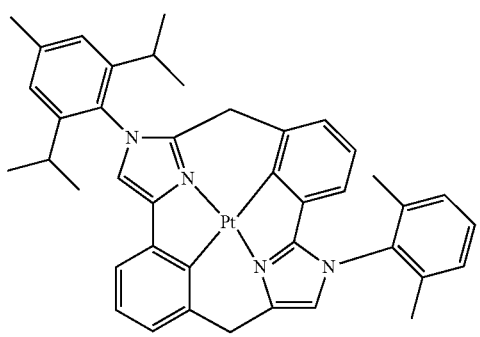
Compound 58'
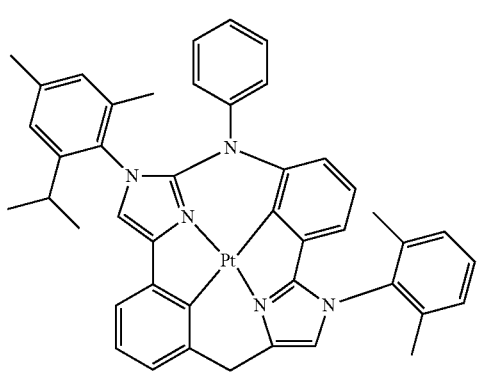
Compound 59'
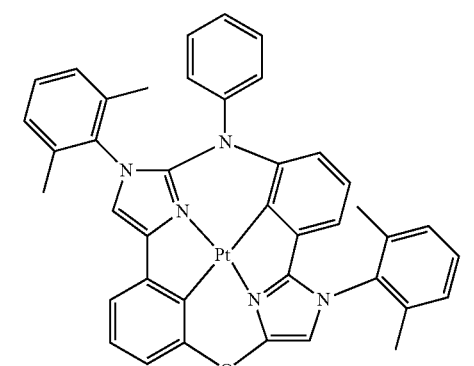
Compound 60'
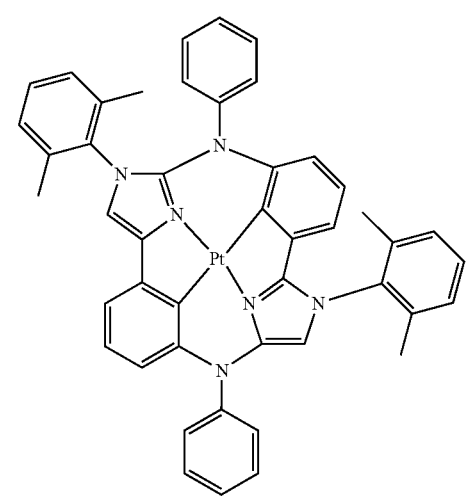

Compound 61'

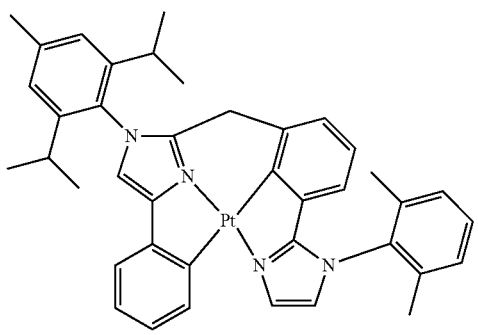

Compound 62'

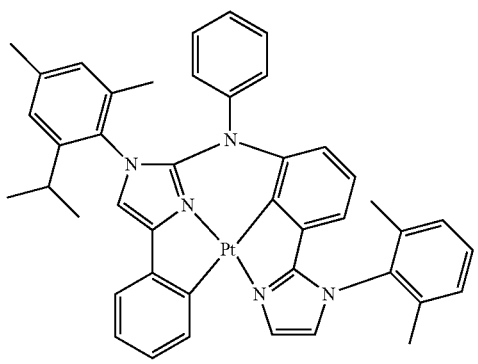

Compound 63'

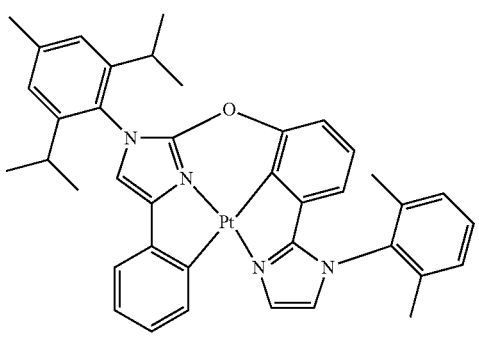

Compound 64'

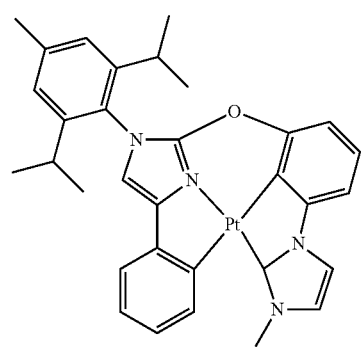

Compound 65'

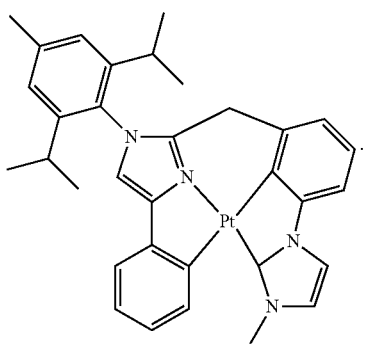

Additionally, a first device comprising an organic light emitting device is provided. The organic light emitting device further comprises an anode, a cathode, and an organic layer. The organic layer is disposed between the anode and the cathode, and it comprises a compound having the formula:

Formula I'

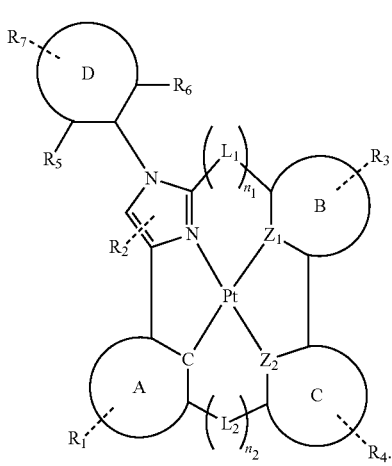

Ring A, ring B, ring C and ring D are each independently a 5- or 6-membered carbocyclic or heterocyclic ring. $L_1$ and $L_2$ are independently selected from the group consisting of a single bond, BR, NR, O, Se, C=O, S=O, $SO_2$, CRR', SiRR', and GeRR'. $n_1$ is 0 or 1. $n_2$ is 0 or 1. $n_1+n_2$ is at least equal to 1. $Z_1$ and $Z_2$ are independently a nitrogen atom or a carbon atom. $R_1$, $R_2$, $R_3$, $R_4$, and $R_7$ may represent mono-, di-, tri-, or tetra-substitutions. $R_1$ is optionally fused to ring A. $R_3$ is optionally fused to ring B. $R_4$ is optionally fused to ring C. $R_7$ is optionally fused to ring D. $R_3$ and $R_4$ are optionally joined to form into a ring. At least one of ring B and ring C is a 5-membered carbocyclic or heterocyclic ring. $R_1$, $R_2$, $R_3$, $R_4$, $R_5$, $R_6$, and $R_7$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. At least one of $R_5$ and $R_6$ is not hydrogen or deuterium.

The various specific aspects discussed above for compounds having Formula I' are also applicable to a compound having Formula I' that is used in the first device. In particular, specific aspects of ring A, ring B, ring C, ring D, $L_1$, $L_2$, $n_1$, $n_2$, $R_1$, $R_2$, $R_3$, $R_4$, $R_5$, $R_6$, $R_7$, $R'_1$, $R'_2$, $R'_3$, Formulas II'-IX', and Compounds 1'-65' of the compound having Formula I' are also applicable to a compound having Formula I' that is used in a device.

In one aspect, the organic layer is an emissive layer and the compound is an emissive dopant.

In one aspect, the organic layer further comprises a host. In another aspect, the host comprises a triphenylene containing benzo-fused thiophene or benzo-fused furan, and any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CC_nH_{2n+1}$, $Ar_1$, $Ar_1-Ar_2$, $C_nH_{2n}-Ar_1$, or no substitution. n is from 1 to 10. $Ar_1$ and $Ar_2$ are independently selected from the group consisting of benzene, biphenyl, naphthalene, triphenylene, carbazole, and heteroaromatic analogs thereof.

In one aspect, the host has the formula:

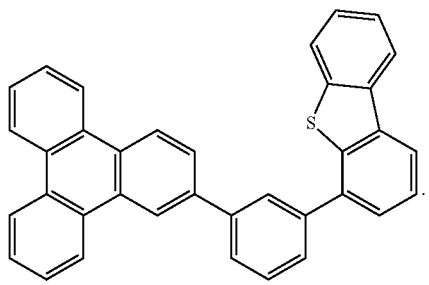 [SMILES: c1cc(-c2ccc3c4ccccc4c4ccccc4c3c2)cc(-c2cccc3c2sc2ccccc23)c1]

In another aspect, the host is selected from the group consisting of:

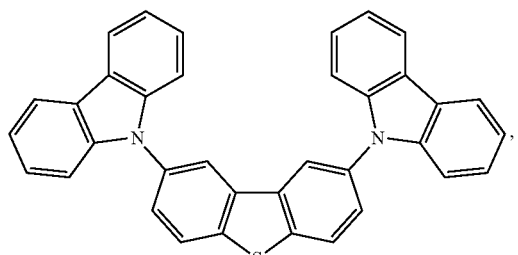

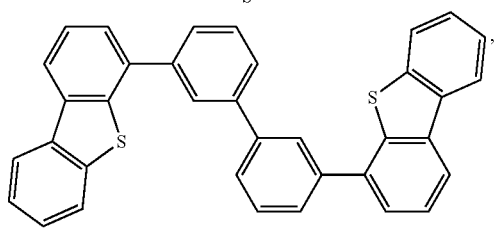

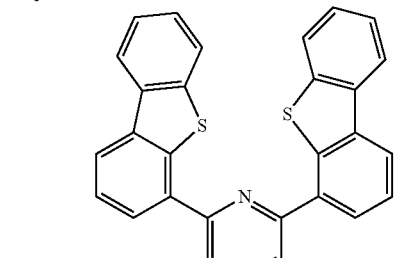

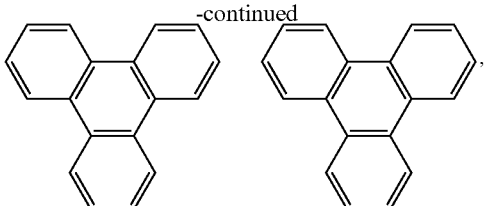

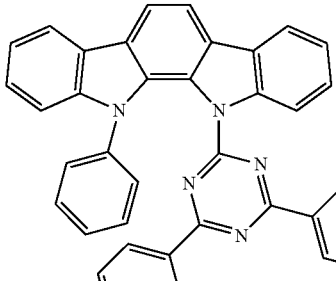

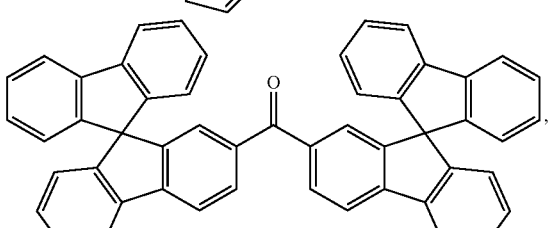

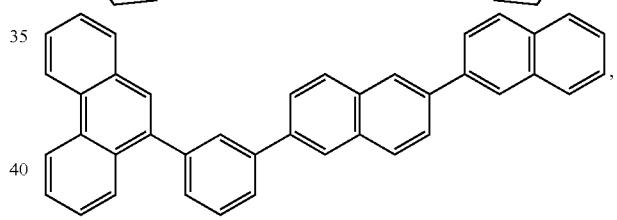

and combinations thereof.

In yet another aspect, the host is a metal complex.

In one aspect, the organic layer is an emissive layer and the compound is a non-emissive dopant.

In one aspect, the first device is a consumer product. In another aspect, the first device is an organic light emitting device. In yet another aspect, the first device comprises a lighting panel.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
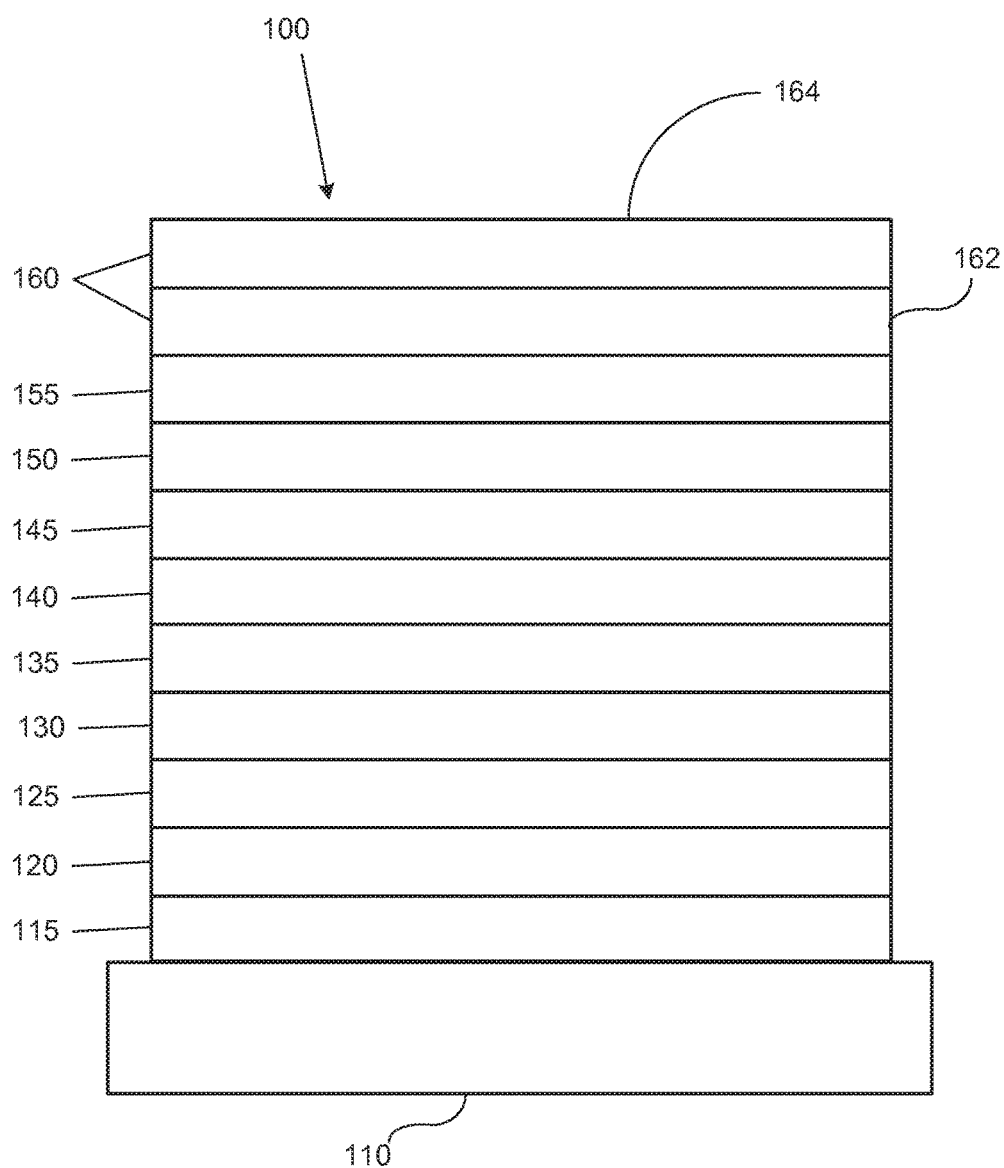
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
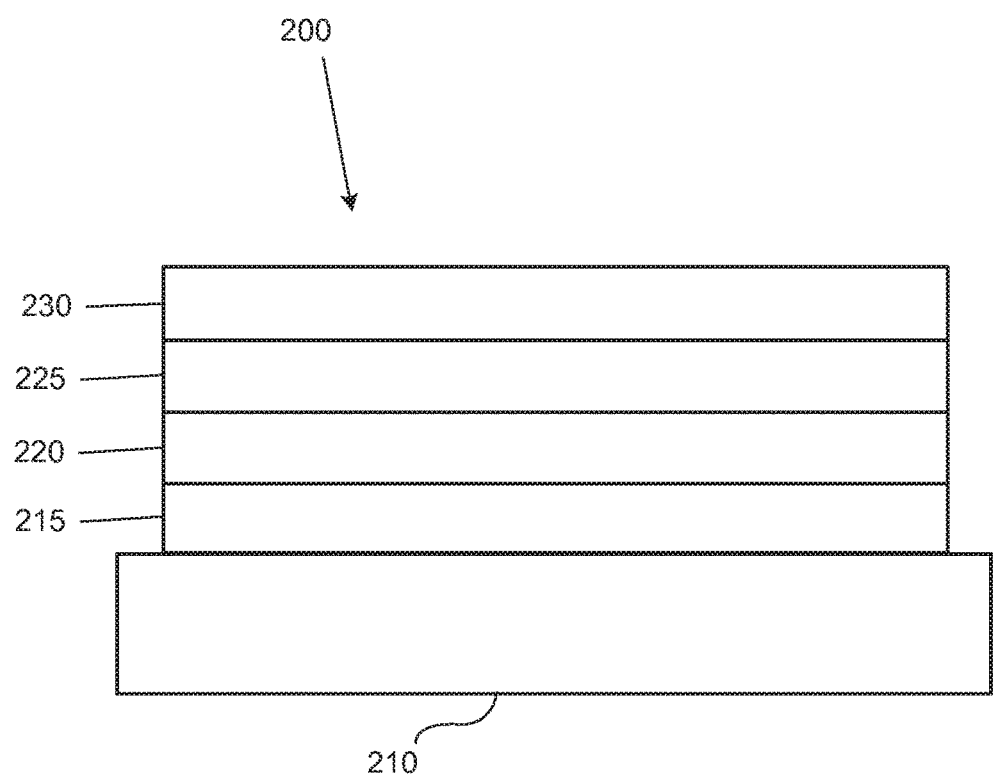
FIG. 2 shows an inverted organic light emitting device that does not have a separate electron transport layer.
Figure 3:
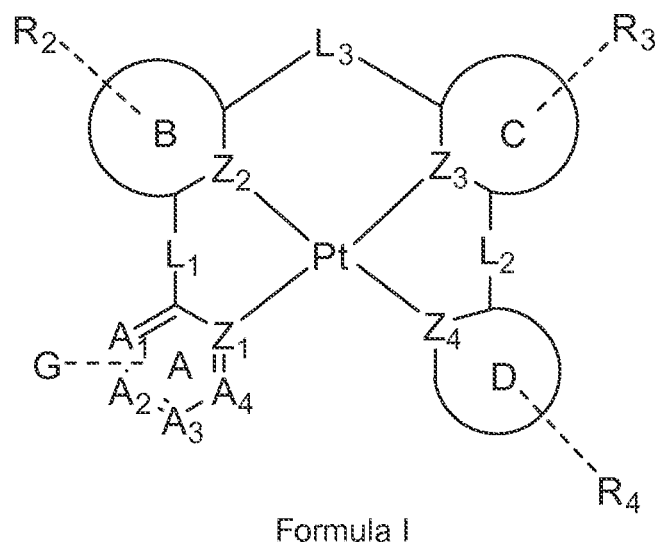
FIG. 3 shows a compound of Formula I.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, now U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, aryalkyl, heterocyclic group, aryl, aromatic group, and heteroaryl are known to the art, and are defined in U.S. Pat. No. 7,279,704 at cols. 31-32, which are incorporated herein by reference.

A compound having the formula:

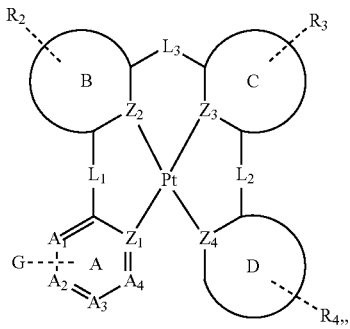

Formula I is provided, wherein G has the structure

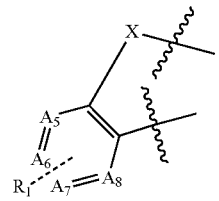

and wherein G is fused to any two adjacent carbon atoms on ring A. Ring B, ring C, and ring D are 5- or 6-membered carbocyclic or heterocyclic aromatic rings. $L_1$, $L_2$, and $L_3$ are independently selected from the group consisting of a single bond, BR, NR, PR, O, S, Se, C=O, S=O, $SO_2$, CRR', SiRR', and GeRR'. At least one of $L_1$, $L_2$, and $L_3$ is not a single bond, and X is selected from the group consisting of BR, NR, PR, O, S, Se, C=O, S=O, $SO_2$, CRR', SiRR', and GeRR'. $Z_1$, $Z_2$, $Z_3$, and $Z_4$ are nitrogen or carbon atoms, and $A_1$, $A_2$, $A_3$, $A_4$, $A_5$, $A_6$, $A_7$, and $A_8$ comprise carbon or nitrogen. $R_1$, $R_2$, $R_3$, and $R_4$ independently represent mono-, di-, tri-, or tetra-substitution, wherein $R_1$ is optionally fused, $R_2$ is optionally fused to ring B, $R_3$ is optionally fused to ring C, and $R_4$ is optionally fused to ring D. $R_3$ and $R_4$ are optionally linked to form a ring. If $L_2$ is not a single bond, $R_3$ and $L_2$ or $R_4$ and $L_2$ are optionally linked to form a ring. R, R', $R_1$, $R_2$, $R_3$, and $R_4$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one embodiment, the compound has a neutral charge. In one embodiment, the platinum center in the compounds of Formula I is platinum(II). In one embodiment, at least two of $Z_1$, $Z_2$, $Z_3$, and $Z_4$ are nitrogen atoms. In another embodiment, at least two of $Z_1$, $Z_2$, $Z_3$, and $Z_4$ are carbon atoms.

In one embodiment, at least one of ring B, ring C, and ring D comprises a carbene ligand coordinated to Pt. In another embodiment, at least one of $Z_1$, $A_1$, $A_2$, $A_3$, $A_4$, $A_5$, $A_6$, $A_7$, and $A_8$ is a nitrogen atom.

In one embodiment, the compound has the formula:

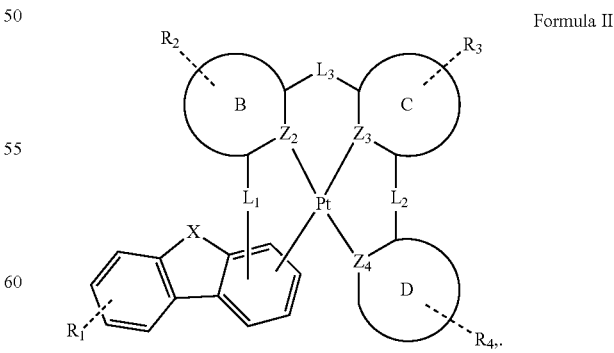

Formula II

In the compound of Formula II, $L_1$ and the bond to the platinum atom can be on any two adjacent atom centers on the illustrated dibenzo ring system.

In another embodiment, the compound has the formula:

Formula III

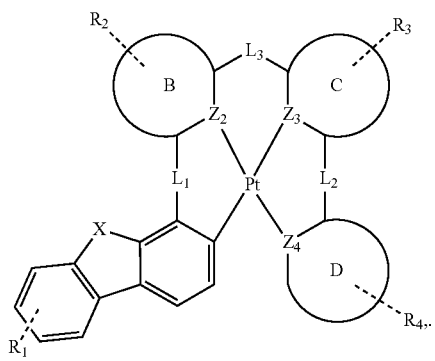

In one embodiment, the compound has the formula:

Formula IV

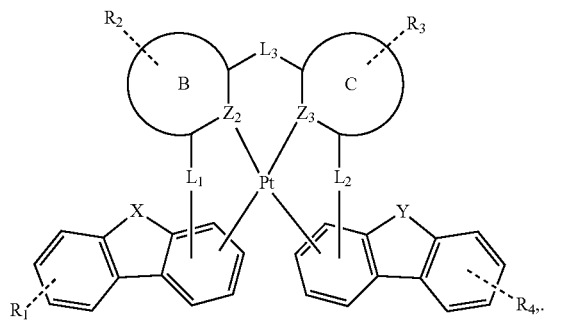

In the compound of Formula IV, $L_1$ and the bond to the platinum atom can be on any two adjacent atom centers on the illustrated dibenzo ring system (i.e. ring system bearing the X fragment, which is also referred to herein as DBX). Similarly, $L_2$ and the bond to the platinum atom can be on any two adjacent atom centers on the illustrated dibenzo ring system (i.e. ring system bearing the Y fragment, which is also referred to herein as DBY). Y is selected from the group consisting of BR, NR, PR, O, S, Se, C=O, S=O, $SO_2$, CRR', SiRR', and GeRR'.

In another embodiment, the compound has the formula:

Formula V

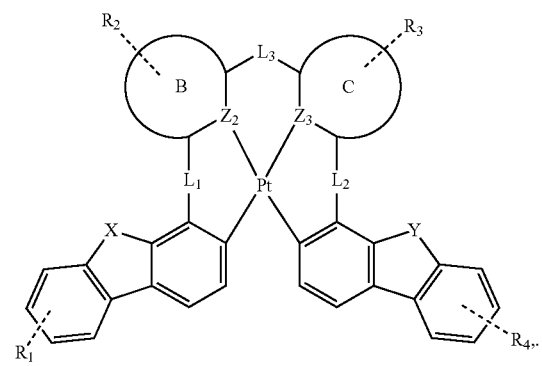

In one embodiment, $L_1$ and $L_2$ are single bonds. In another embodiment, $L_3$ is independently selected from the group consisting of O, S, and NR. In another embodiment, $L_3$ is NR, and R is phenyl or substituted phenyl. In one embodiment, $L_3$ is O.

In one embodiment, $Z_2$ and $Z_3$ are nitrogen atoms. In another embodiment, $Z_2$ and $Z_4$ are nitrogen atoms. In one embodiment, X is independently selected from the group consisting of O, S, and NR. In one embodiment, X is O.

In one embodiment, the compound is selected from the group consisting of:

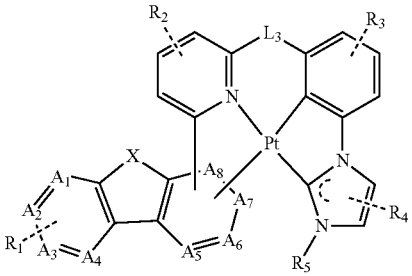

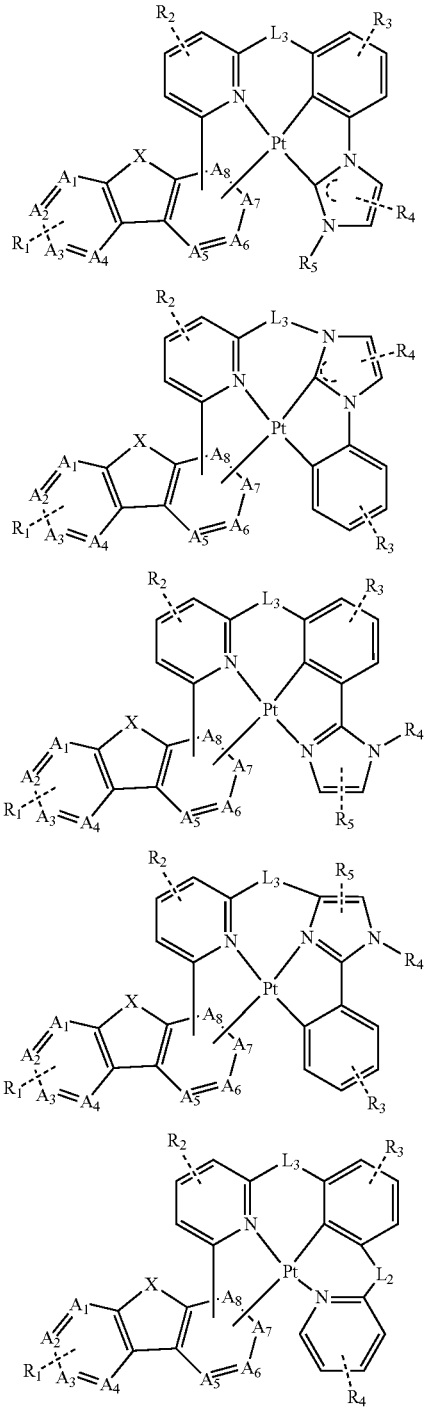

-continued

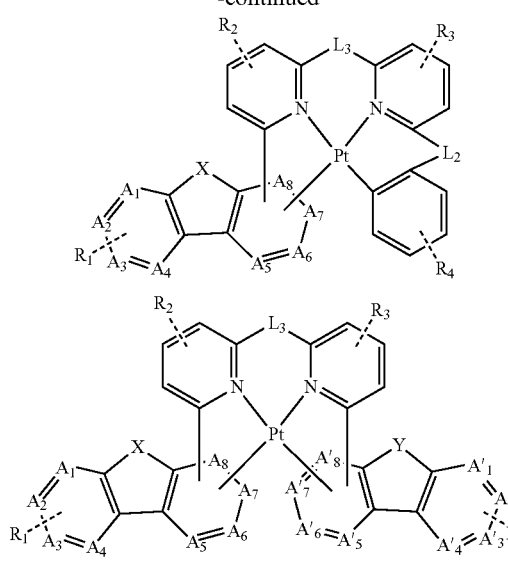

wherein Y is selected from the group consisting of BR, NR, PR, O, S, Se, C=O, S=O, $SO_2$, CRR', SiRR', and GeRR'. $A_1'$, $A_2'$, $A_3'$, $A_4'$, $A_5'$, $A_6'$, $A_7'$, and $A_8'$ comprise carbon or nitrogen. At most one of $A_1$, $A_2$, $A_3$, $A_4$ is nitrogen, and at most one of $A_1'$, $A_2'$, $A_3'$, $A_4'$ is nitrogen. At most one of $A_5$, $A_6$, $A_7$, $A_8$ is nitrogen, and the nitrogen is not bound to Pt. At most one of $A_5'$, $A_6'$, $A_7'$, $A_8'$ is nitrogen, and the nitrogen is not bound to Pt. The Pt forms at least two Pt—C bonds and $R_3$ and $R_4$ may be fused together to form a ring. $R_5$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one embodiment, the compounds of Formula I include:

Compound 1

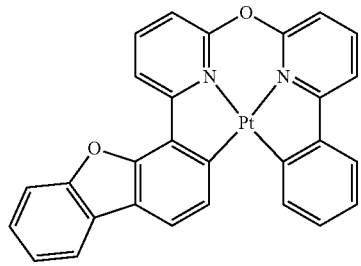

Compound 2

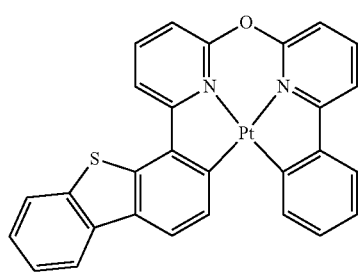

Compound 3

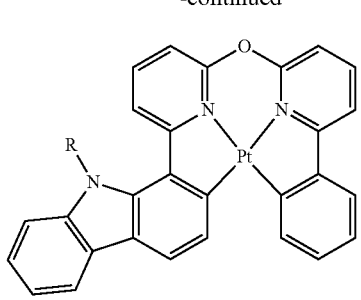

Compound 4

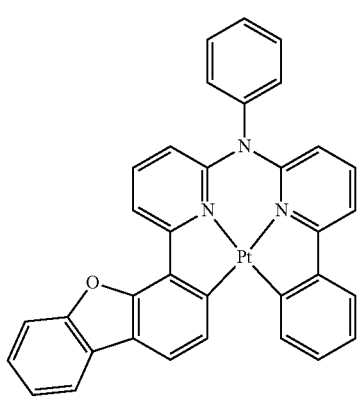

Compound 5

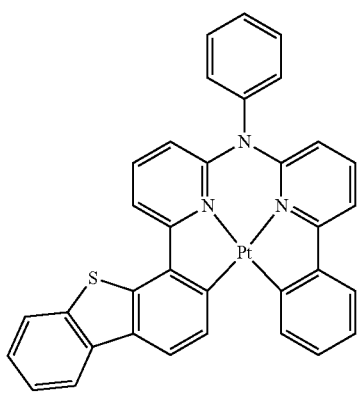

Compound 6

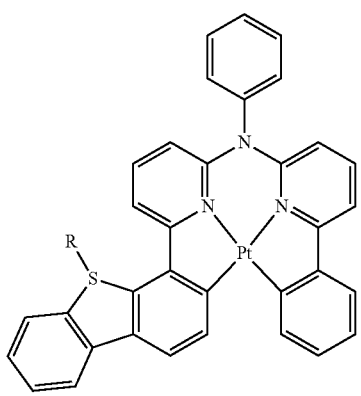

Compound 7
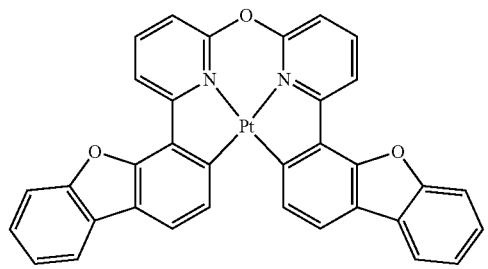
Compound 8
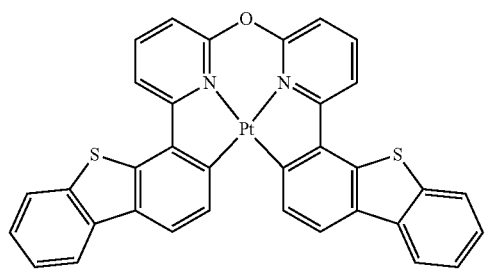
Compound 9
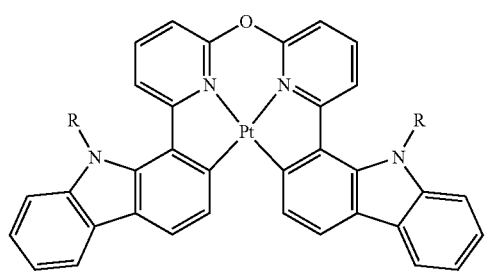
Compound 10
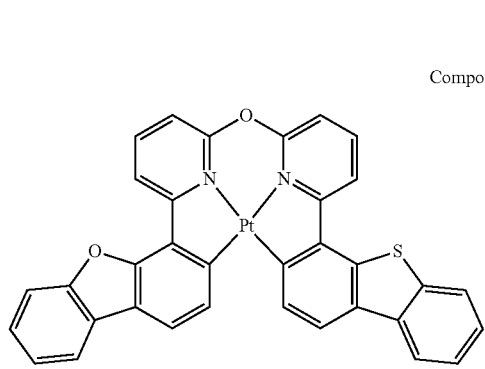
Compound 11
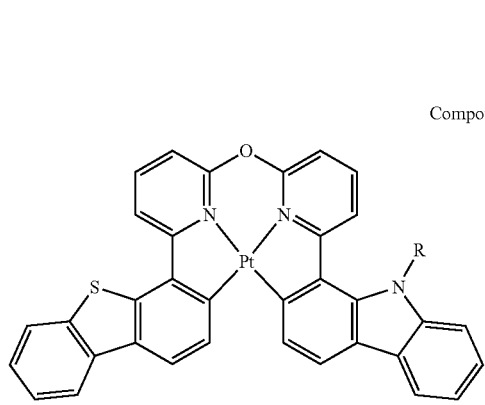
Compound 12
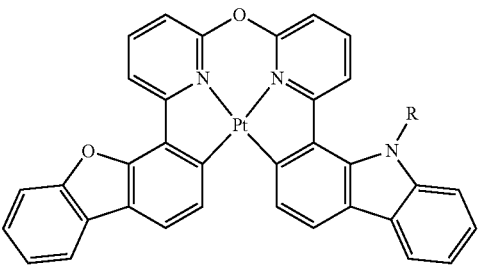
Compound 13
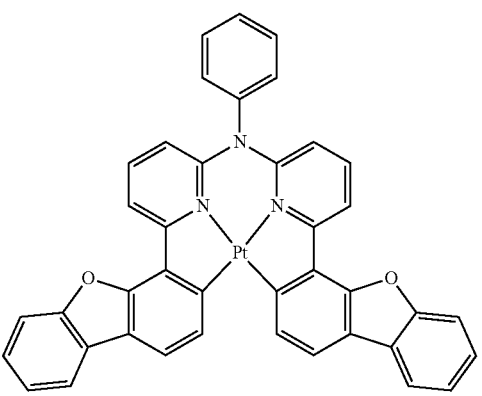
Compound 14
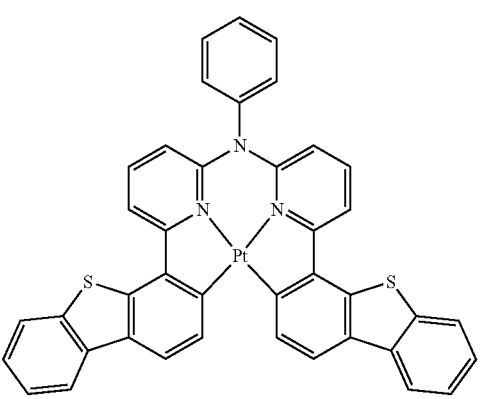
Compound 15
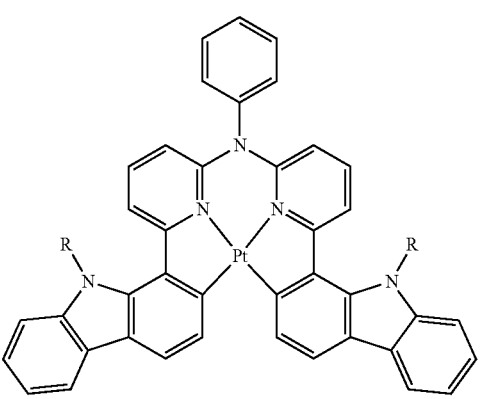

Compound 16
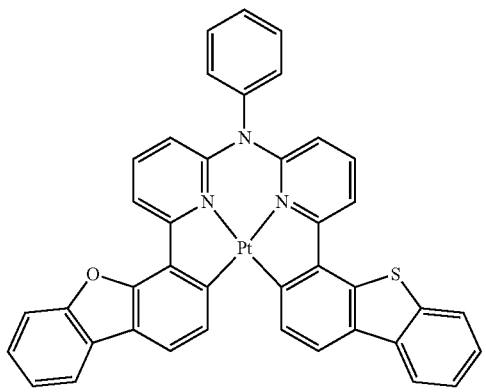
Compound 17
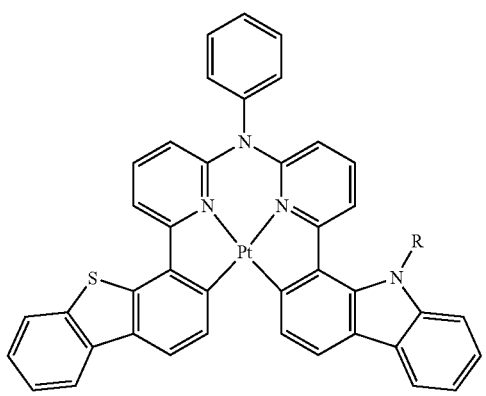
Compound 18
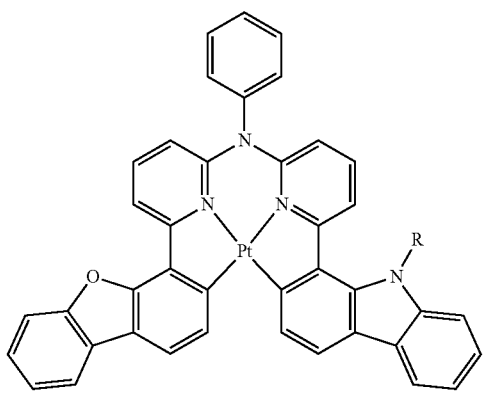
Compound 19
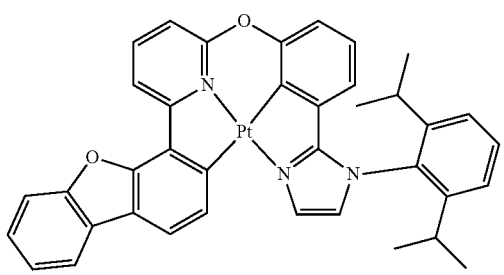
Compound 20
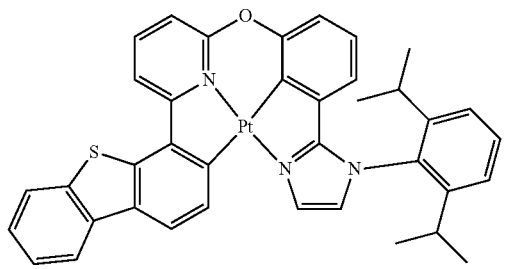
Compound 21
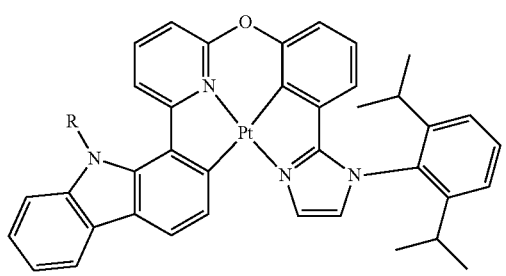
Compound 22
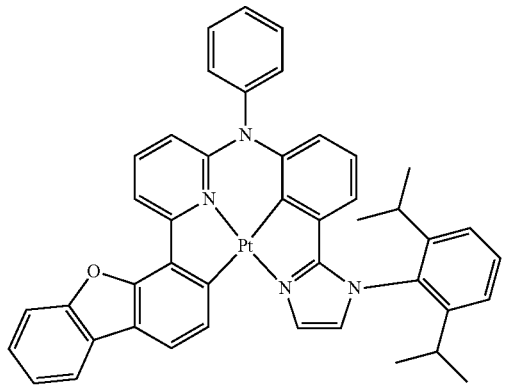
Compound 23
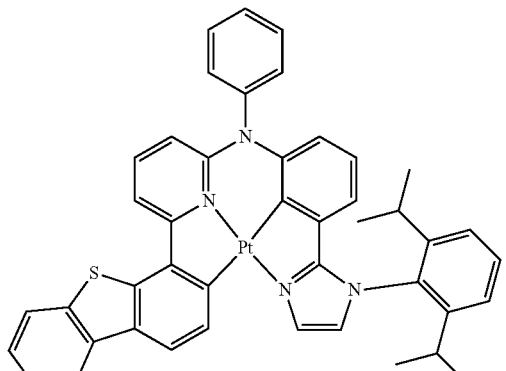

Compound 24
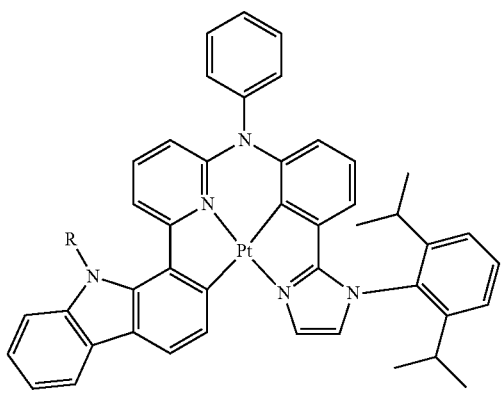
Compound 25
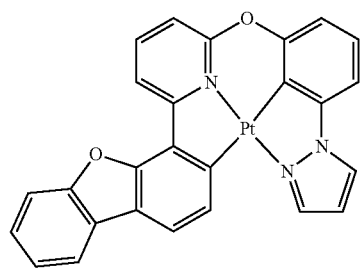
Compound 26
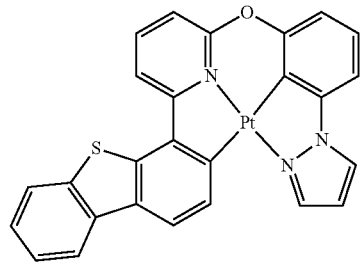
Compound 27
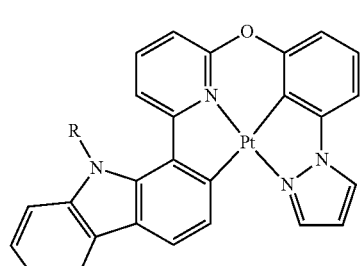
Compound 28
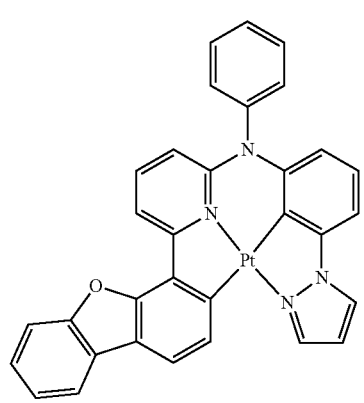
Compound 29
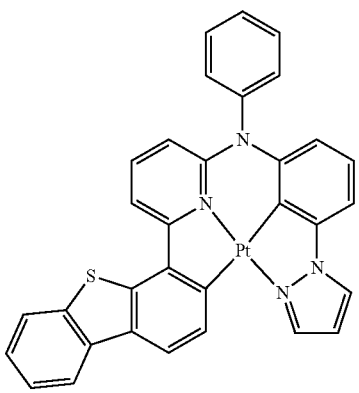
Compound 30
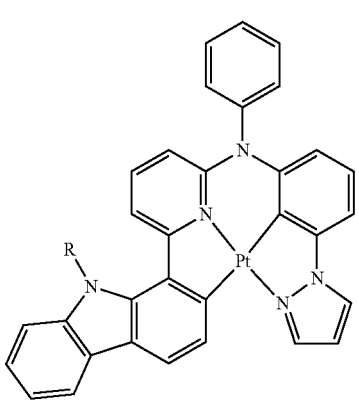
Compound 31
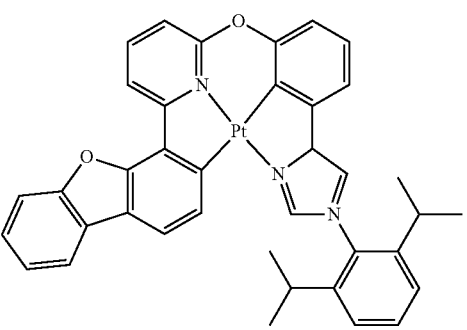
Compound 32
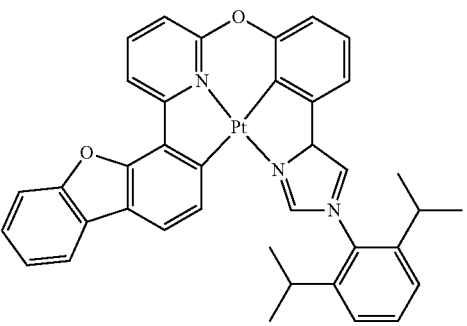

Compound 33
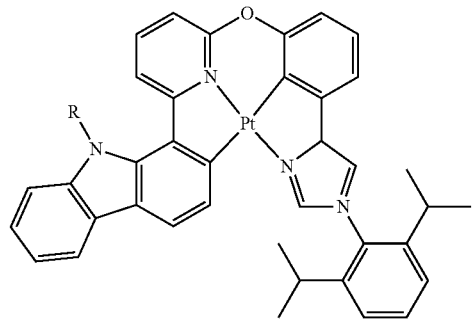
Compound 34
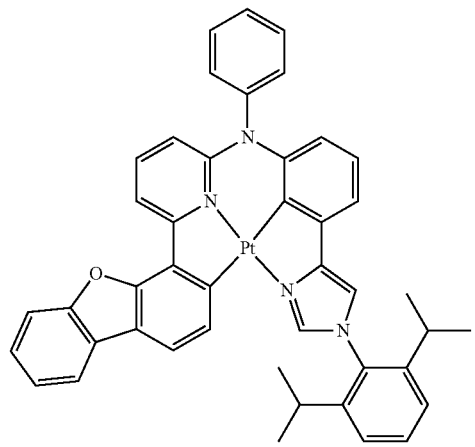
Compound 35
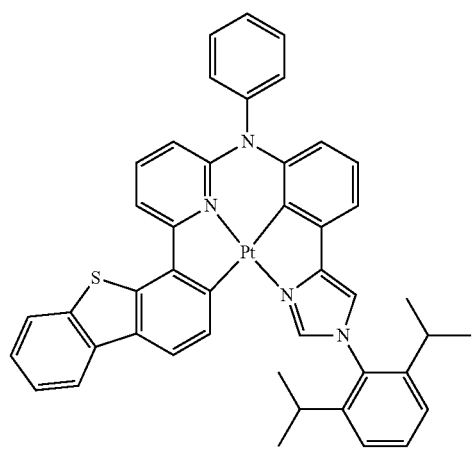
Compound 36
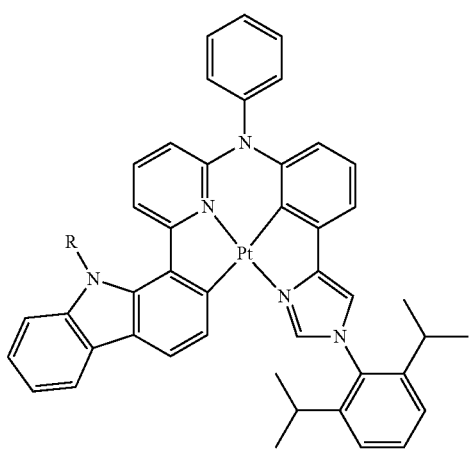
Compound 37
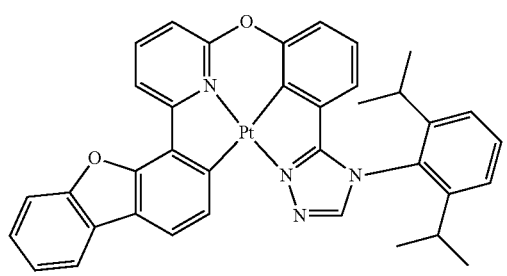
Compound 38
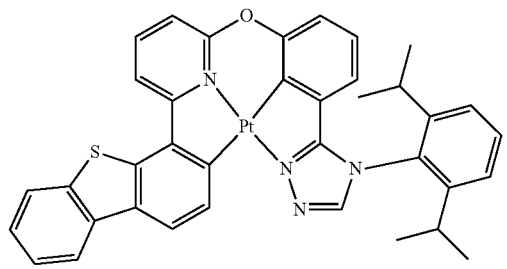
Compound 39
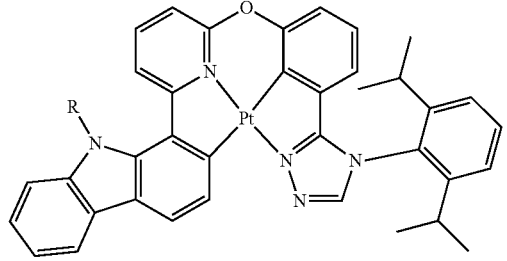

Compound 40
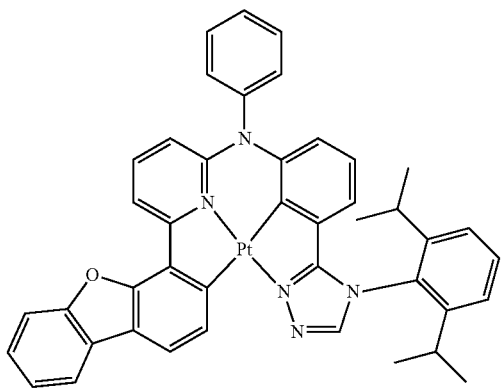
Compound 41
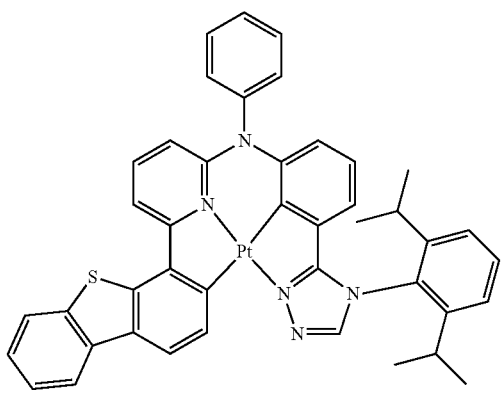
Compound 42
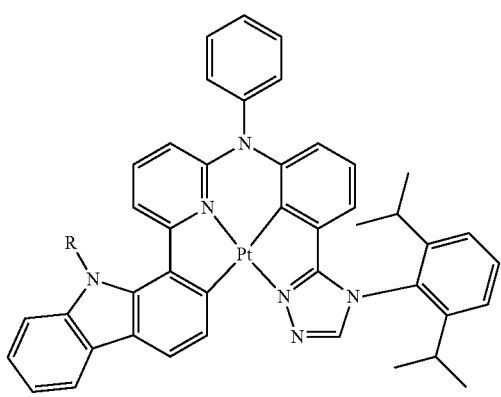
Compound 43
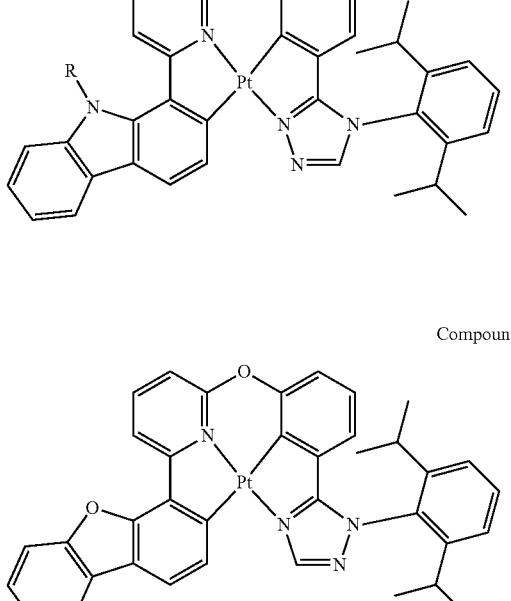
Compound 44
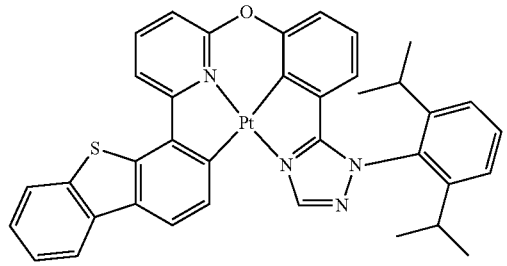
Compound 45
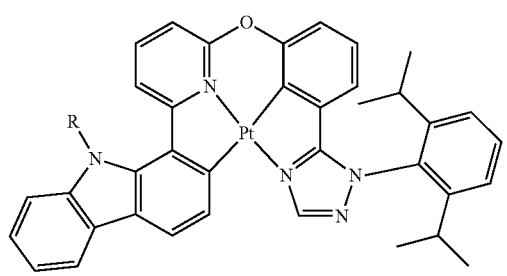
Compound 46
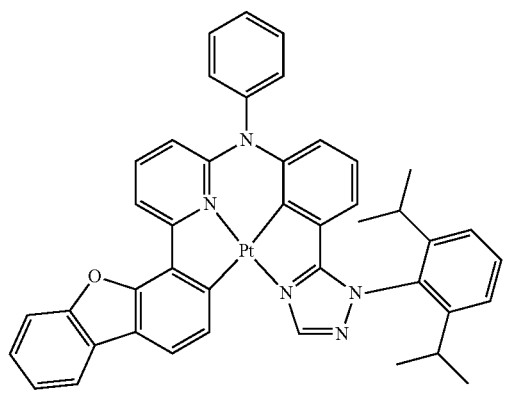
Compound 47
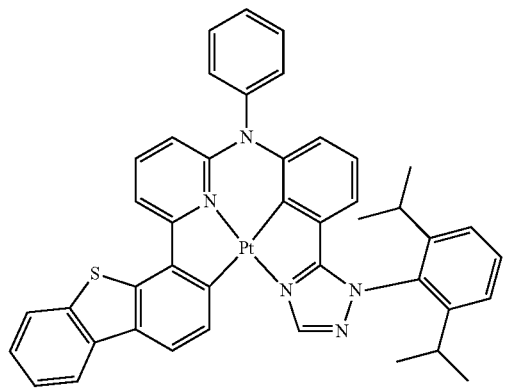

Compound 48
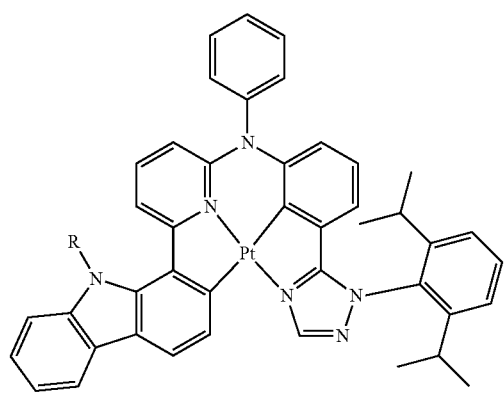
Compound 49
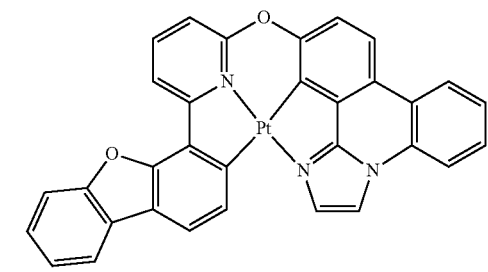
Compound 50
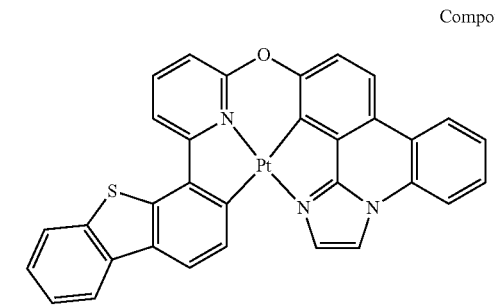
Compound 51
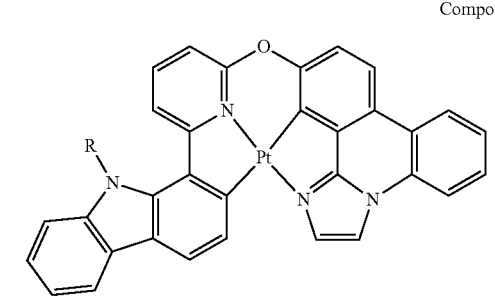
Compound 52
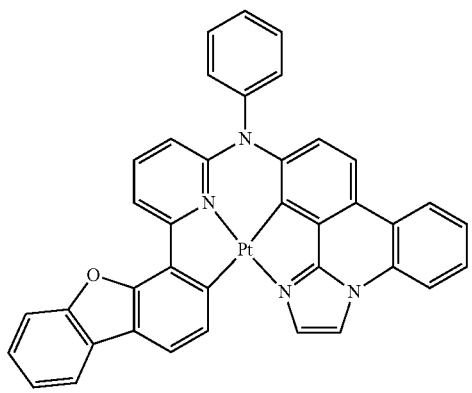
Compound 53
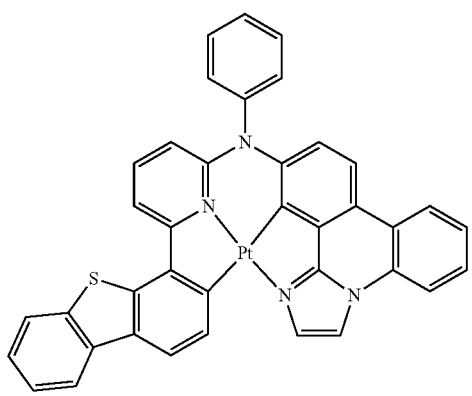
Compound 54
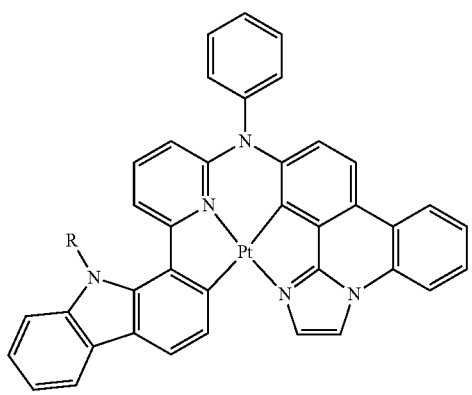
Compound 55
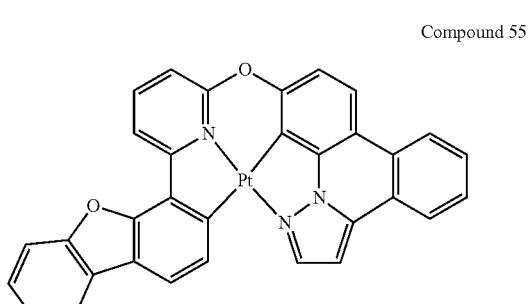

Compound 56
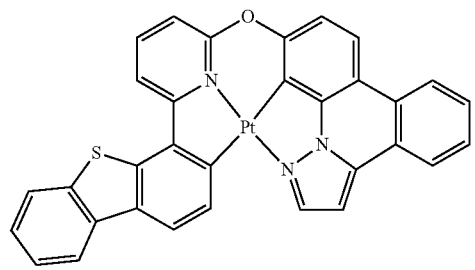
Compound 57
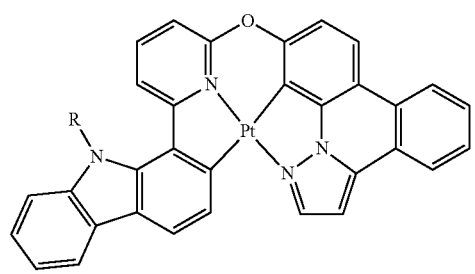
Compound 58
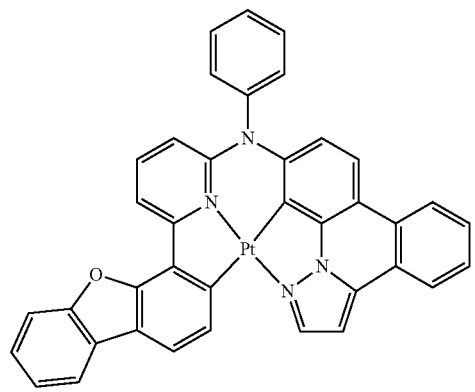
Compound 59
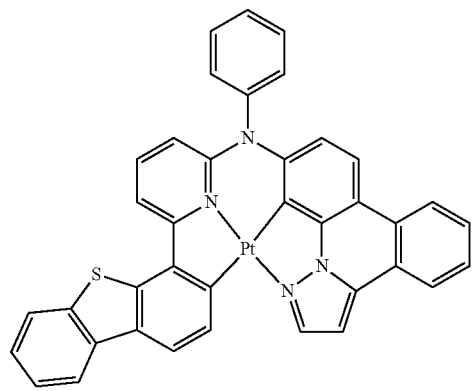
Compound 60
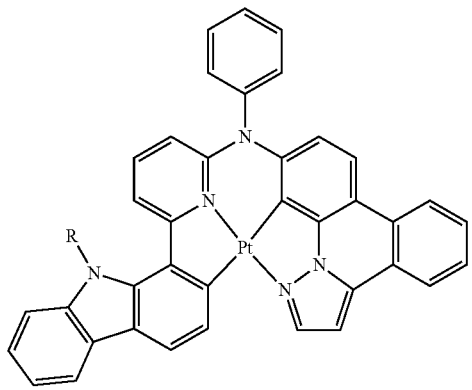
Compound 61
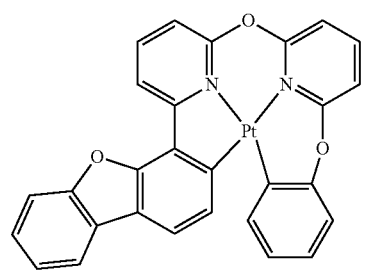
Compound 62
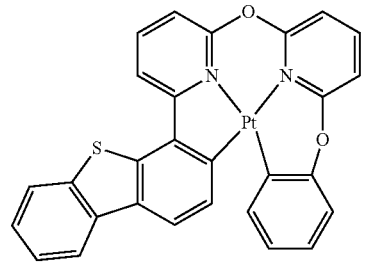
Compound 63
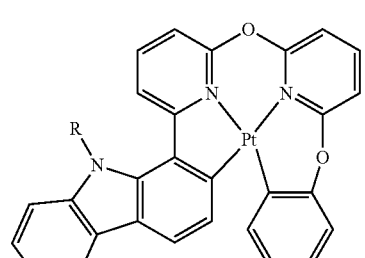
Compound 64
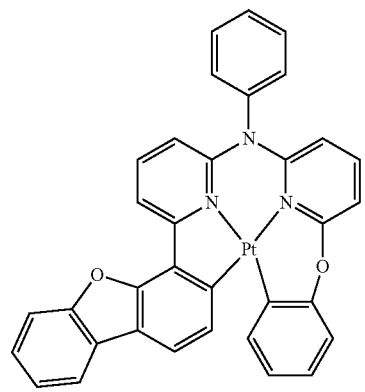

Compound 65
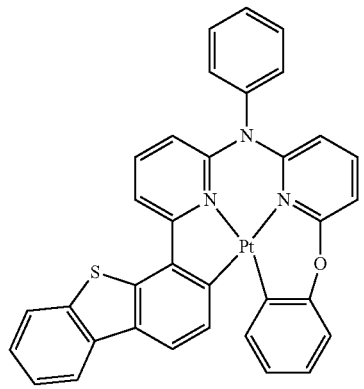
Compound 66
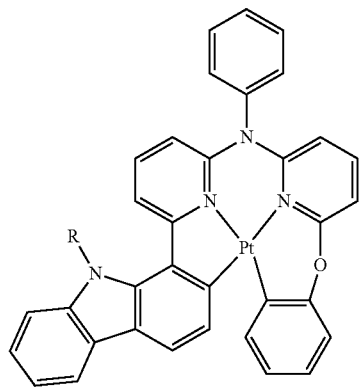
Compound 67
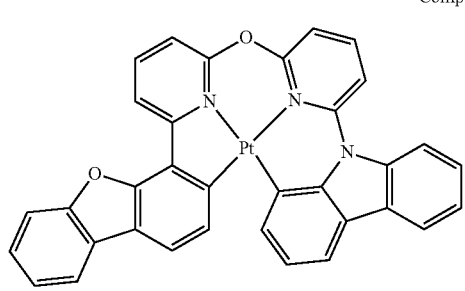
Compound 68
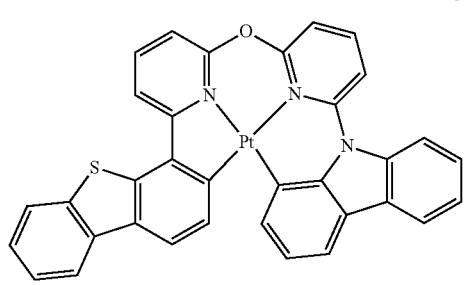
Compound 69
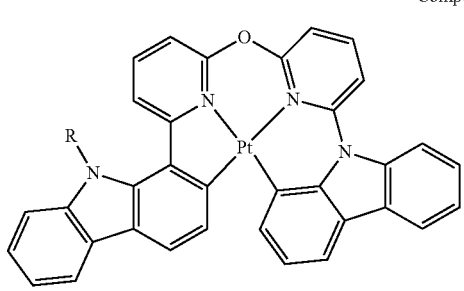
Compound 70
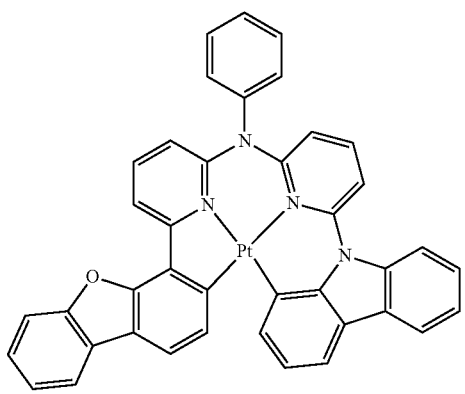
Compound 71
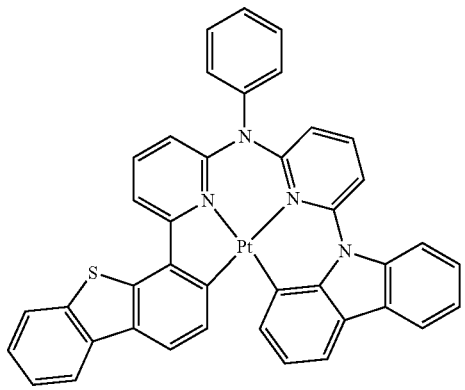
Compound 72
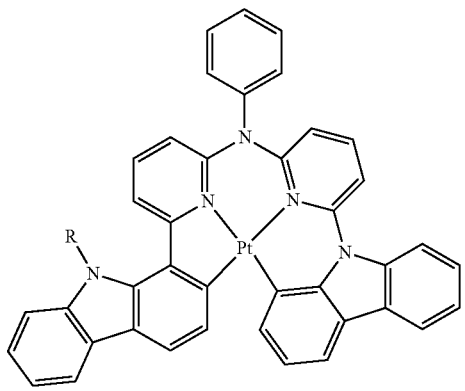

Compound 73
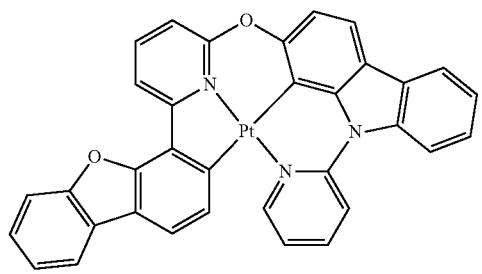
Compound 74
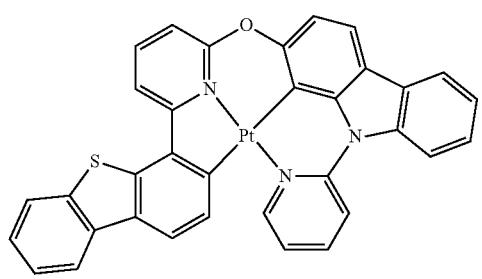
Compound 75
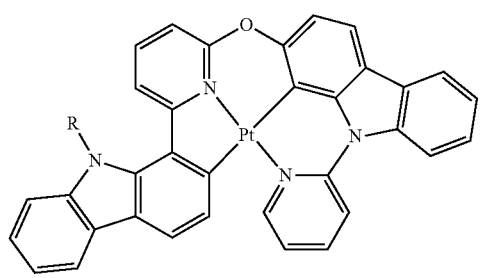
Compound 76
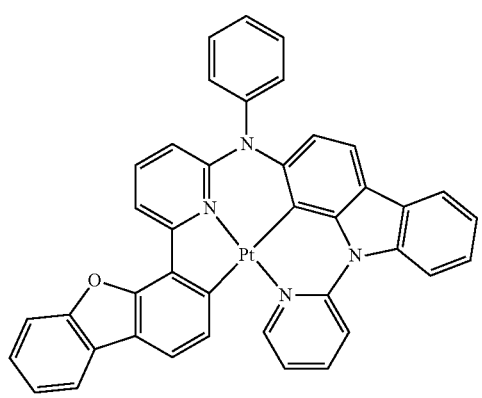
Compound 77
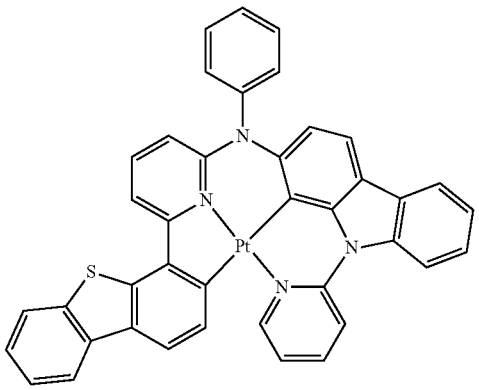
Compound 78
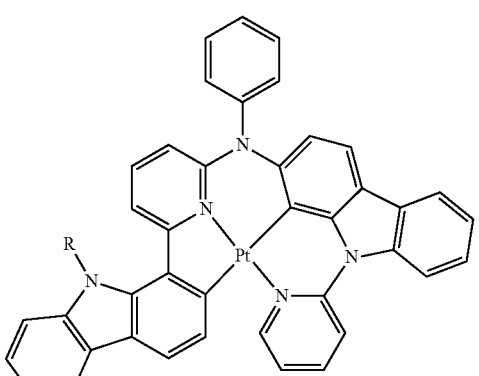
Compound 79
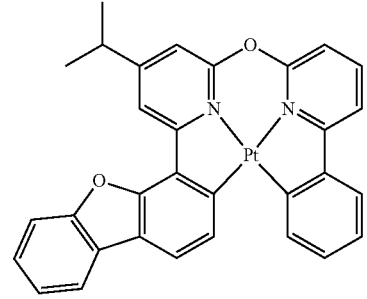
Compound 80
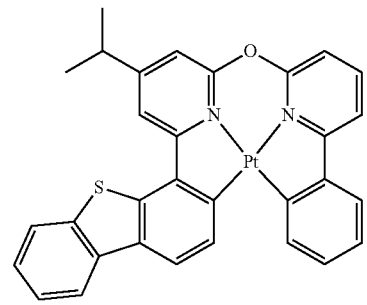

Compound 81
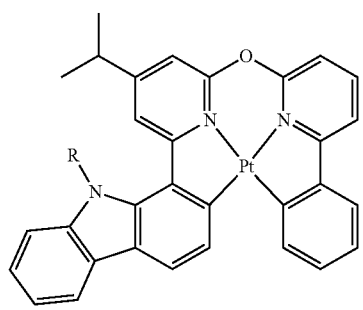
Compound 82
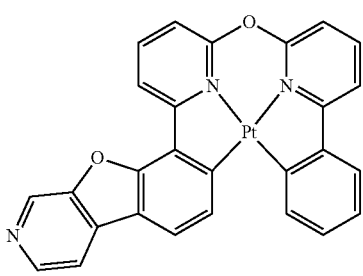
Compound 83
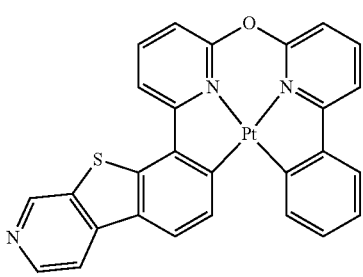
Compound 84
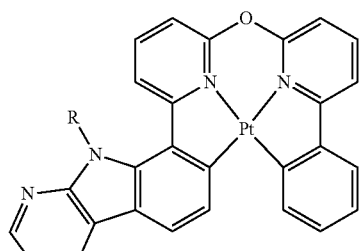
Compound 85
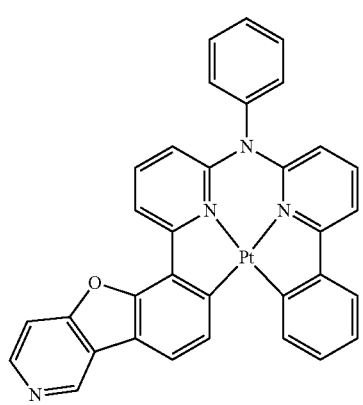
Compound 86
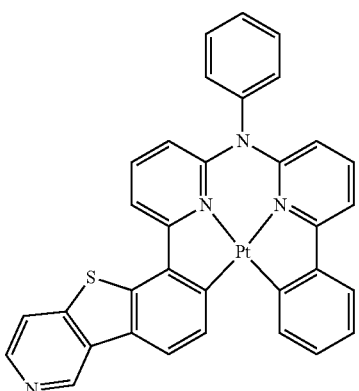
Compound 87
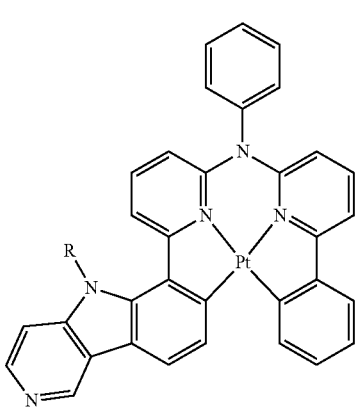
Compound 88
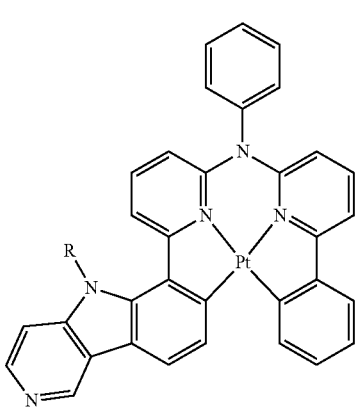
Compound 89
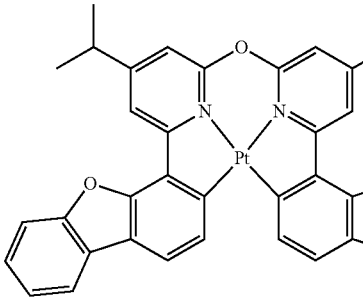

Compound 90
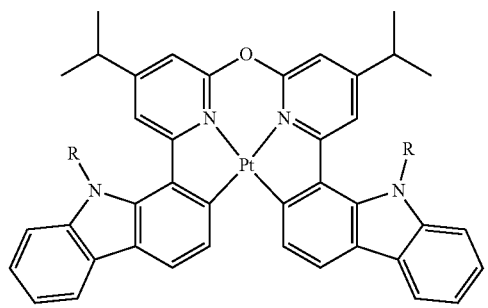
Compound 91
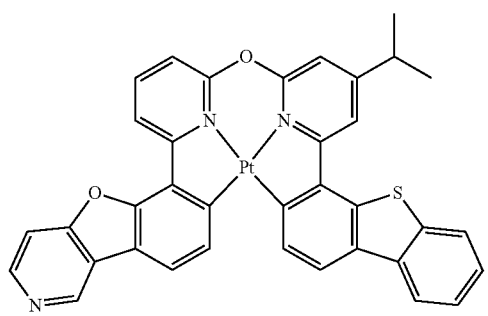
Compound 92
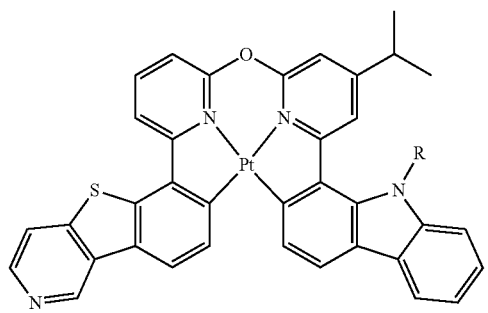
Compound 93
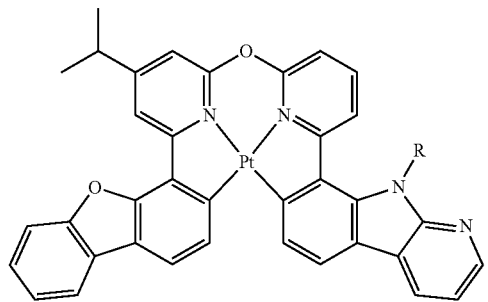
Compound 94
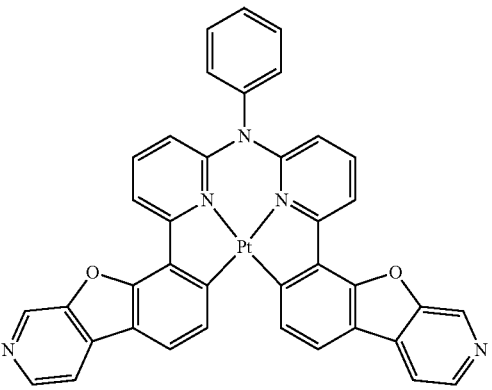
Compound 95
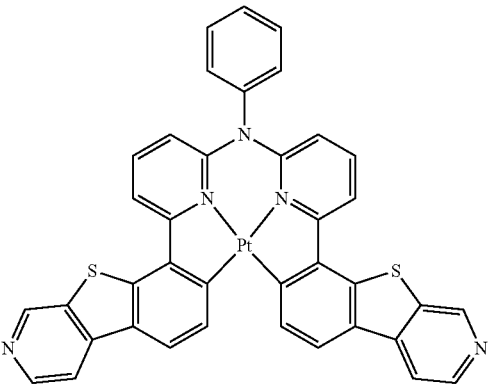
Compound 96
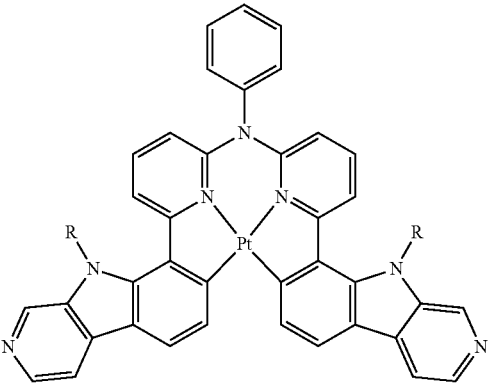
Compound 97
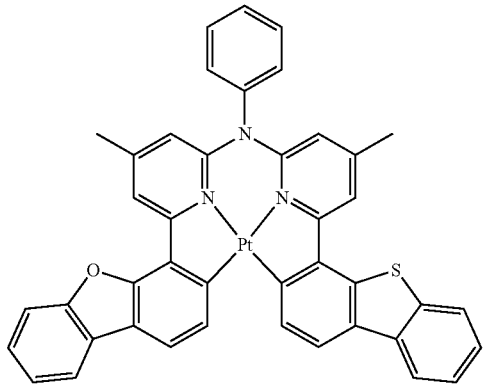

Compound 98
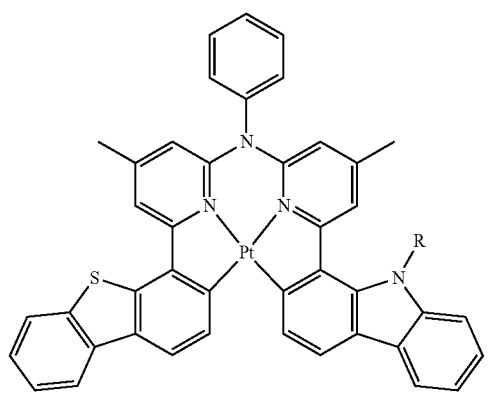
Compound 99
Compound 100
Compound 101
Compound 102
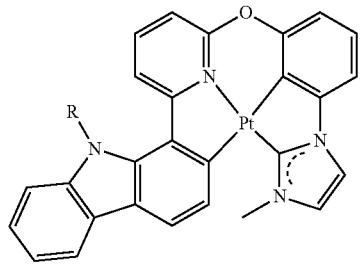
Compound 103
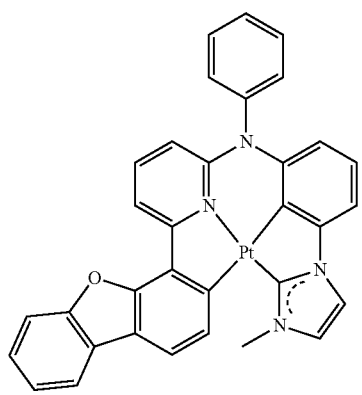
Compound 104
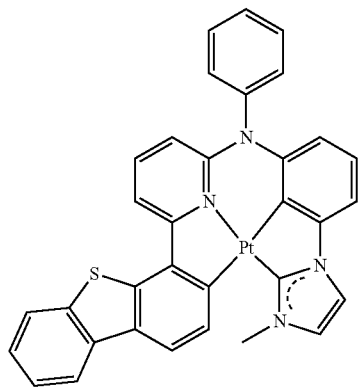
Compound 105
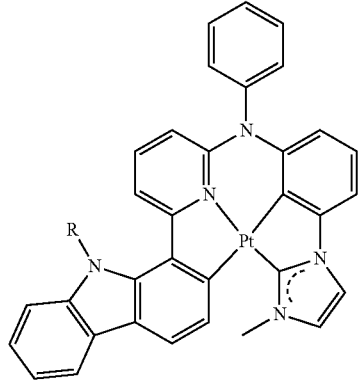

Compound 106
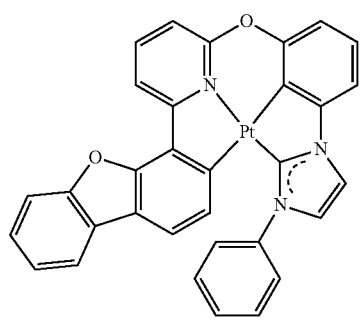
Compound 107
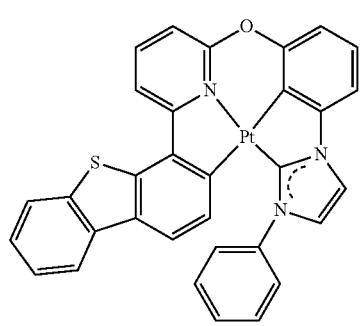
Compound 108
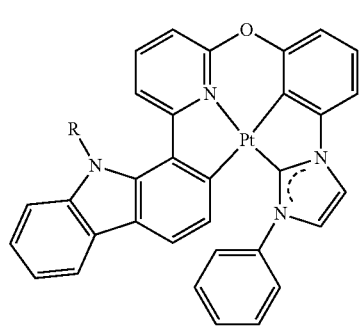
Compound 109
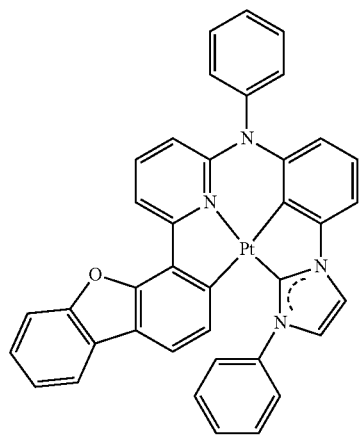
Compound 110
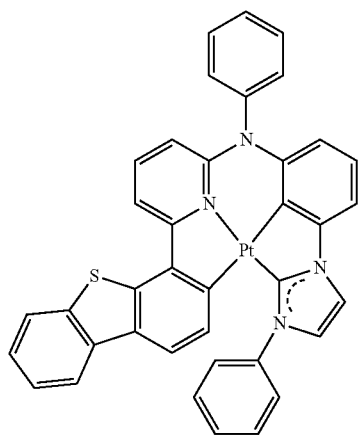
Compound 111
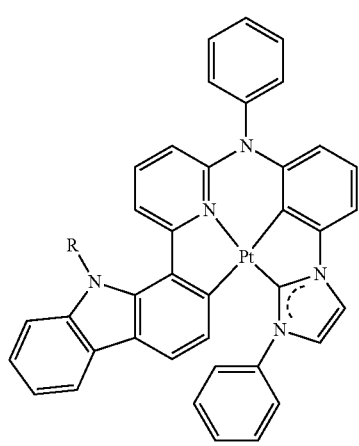
Compound 112
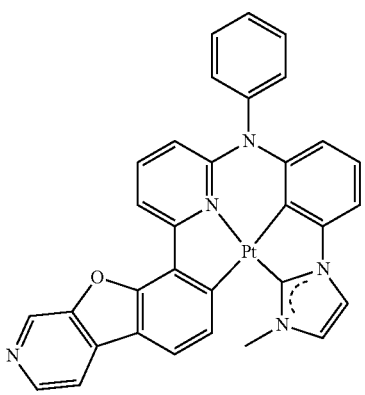

Compound 113
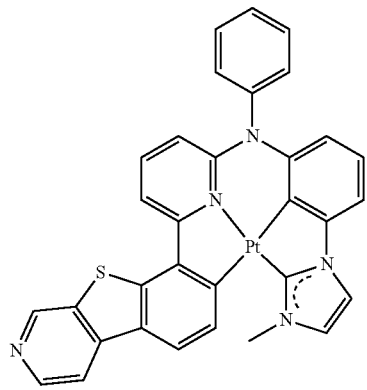
Compound 114
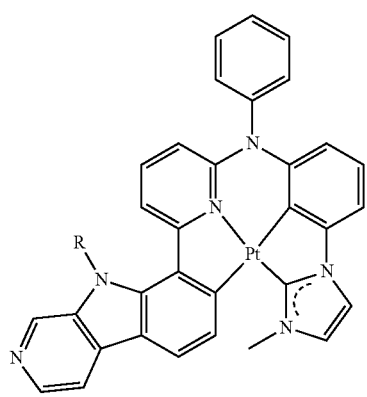
Compound 115
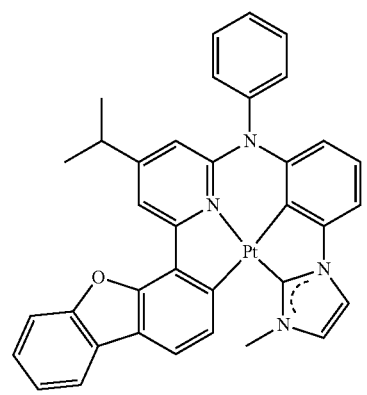
Compound 116
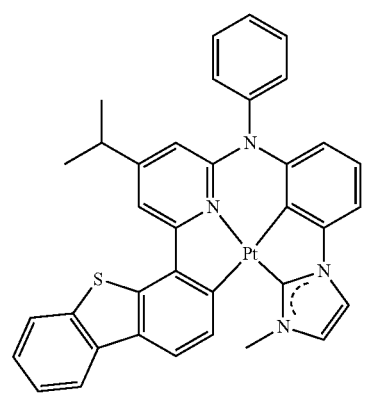
Compound 117
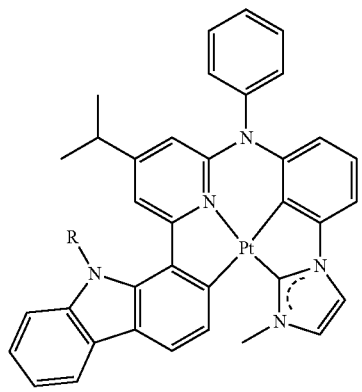
Compound 118
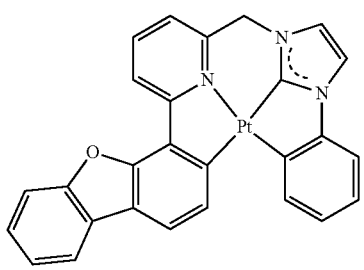
Compound 119
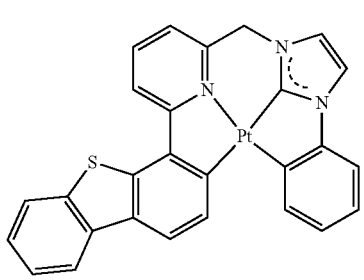
Compound 120
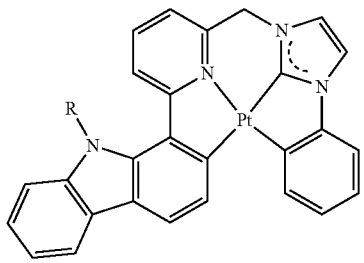
Compound 121
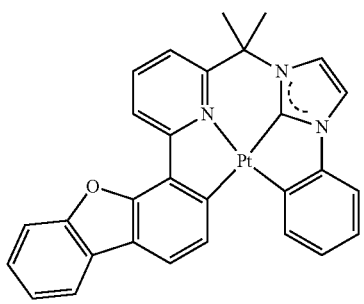

Compound 122
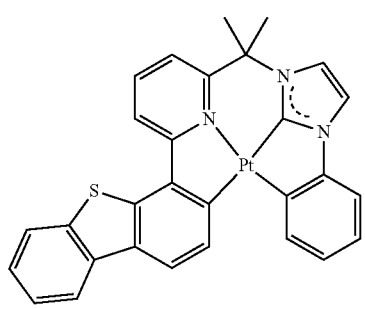
Compound 123
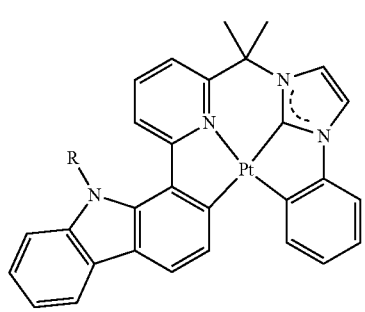
Compound 124
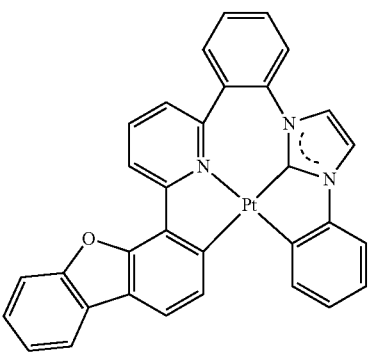
Compound 125
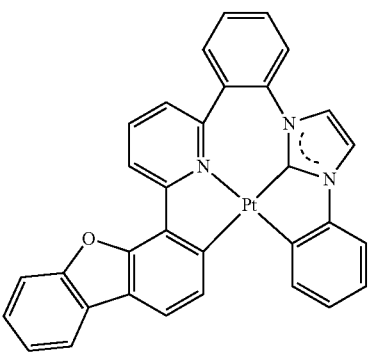
Compound 126
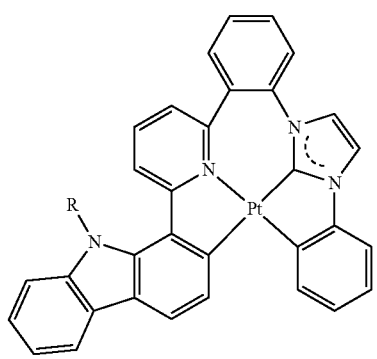
Compound 127
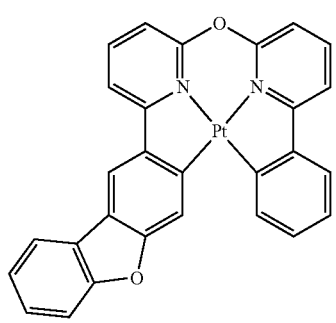
Compound 128
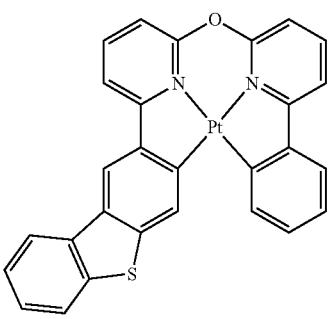
Compound 129
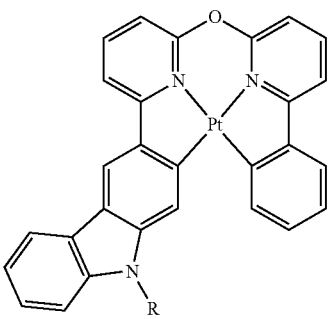

Compound 130
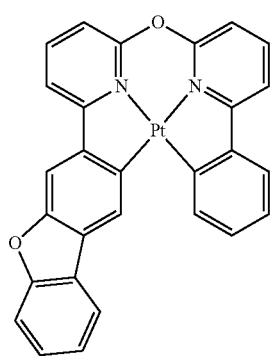
Compound 131
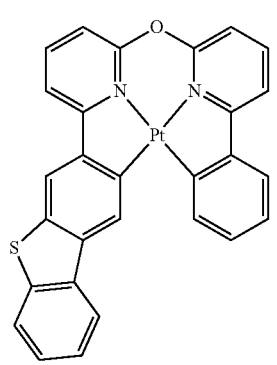
Compound 132
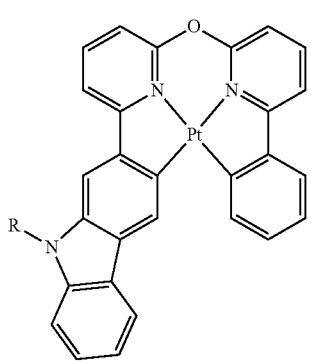
Compound 133
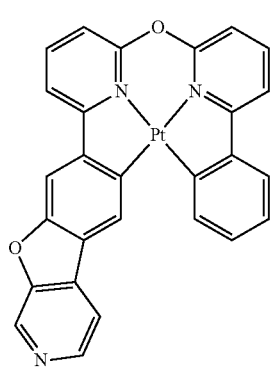
Compound 134
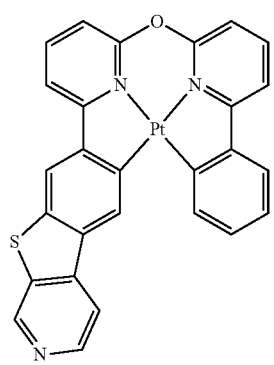
Compound 135
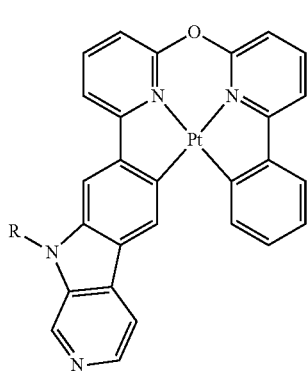
Compound 136
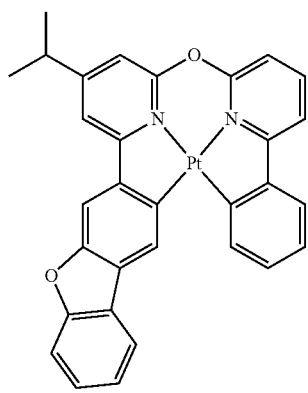
Compound 137
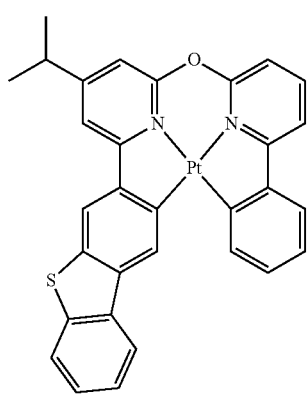

Compound 138
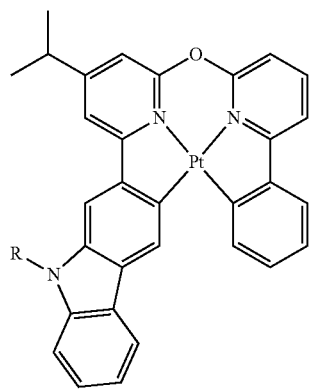
Compound 139
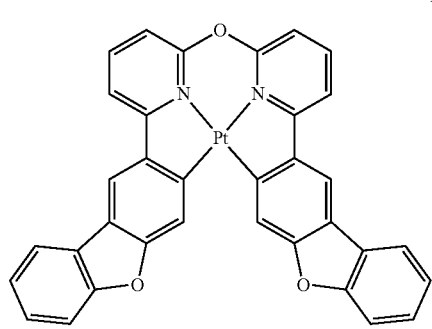
Compound 140
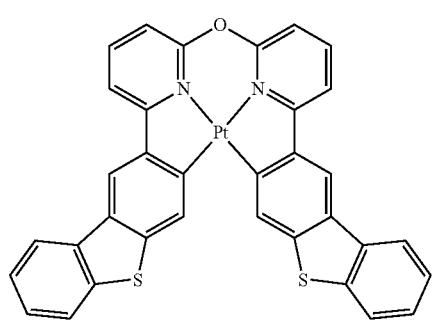
Compound 141
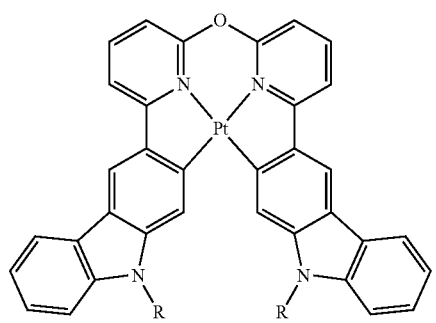
Compound 142
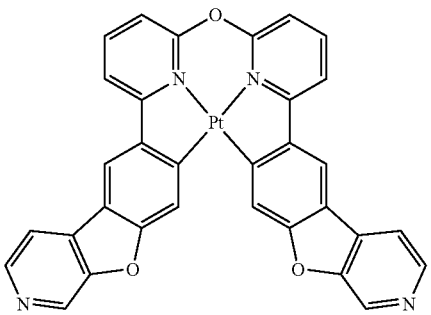
Compound 143
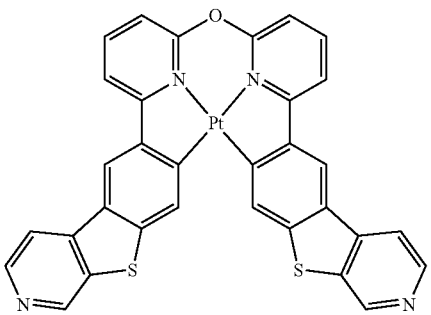
Compound 144
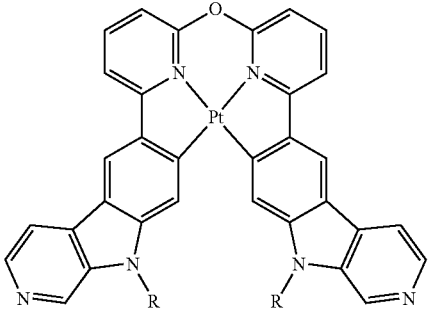
Compound 145
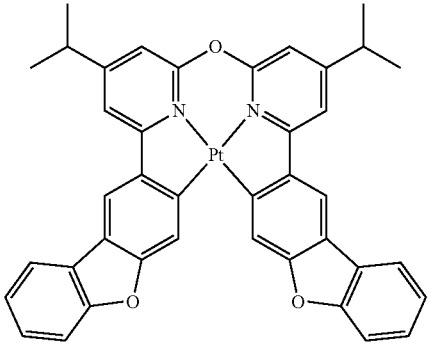

Compound 146
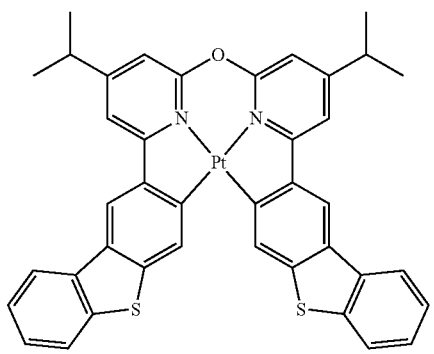
Compound 147
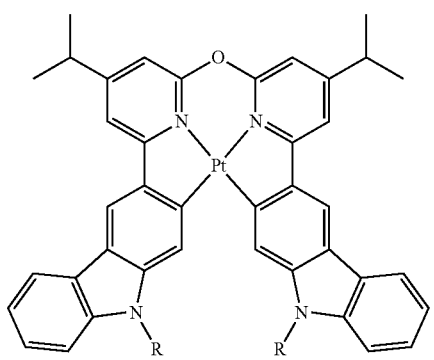
Compound 148
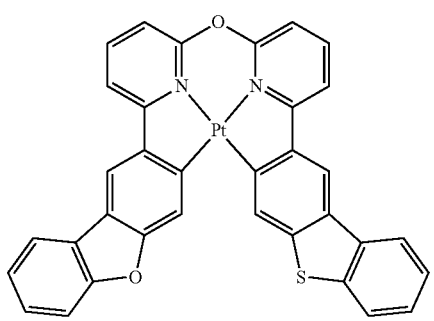
Compound 149
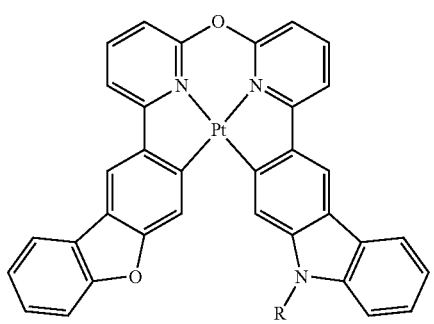
Compound 150
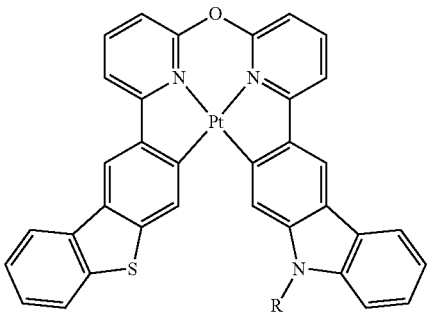
Compound 151
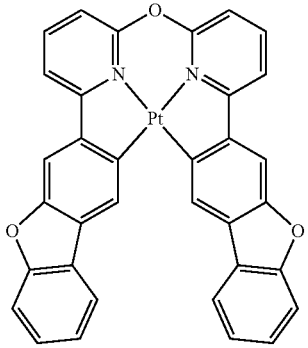
Compound 152
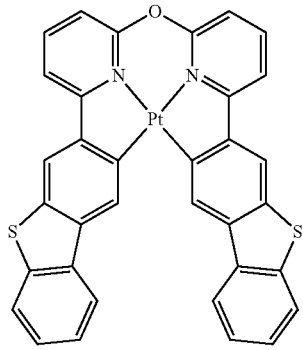
Compound 153
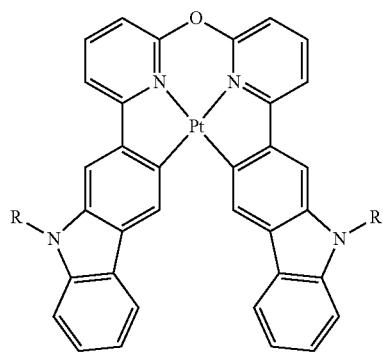

Compound 154
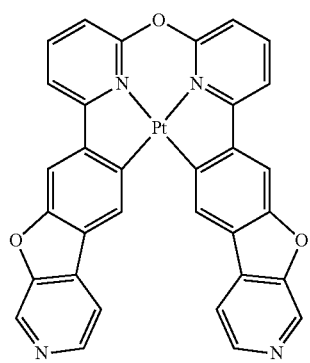
Compound 155
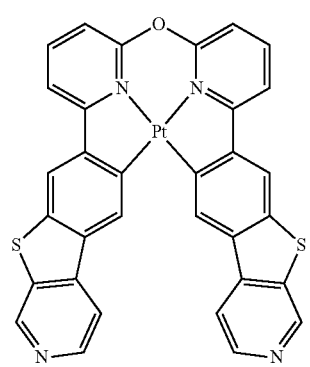
Compound 156
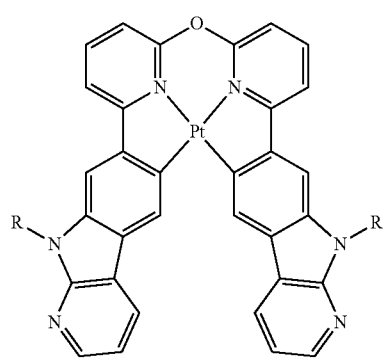
Compound 157
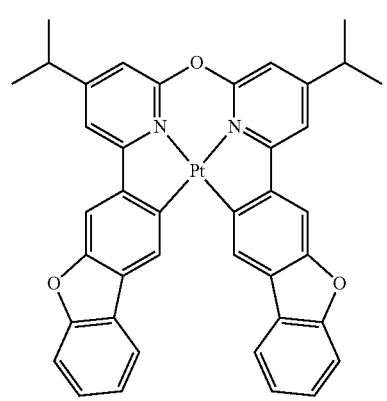
Compound 158
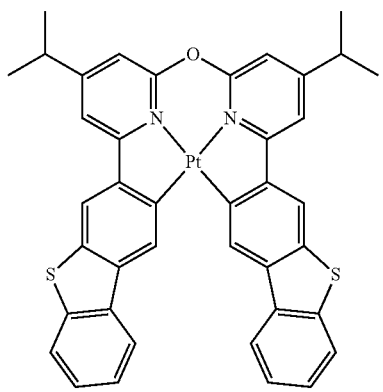
Compound 159
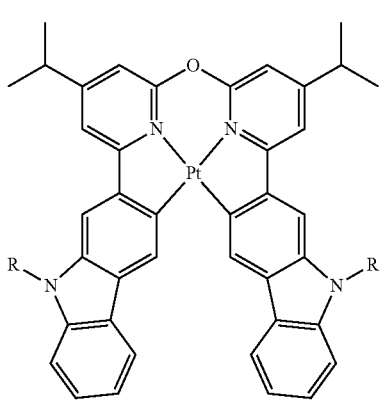
Compound 160
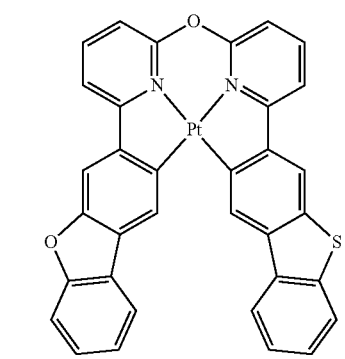
Compound 161
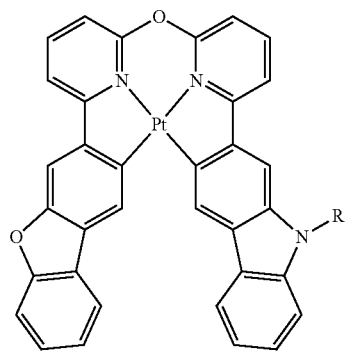

Compound 162
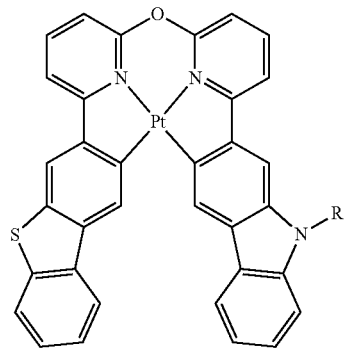
Compound 163
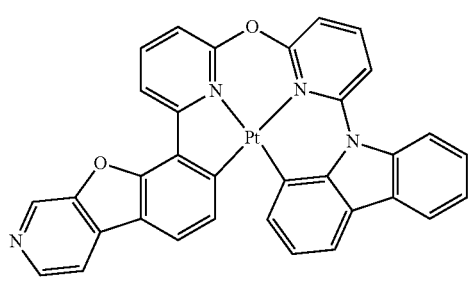
Compound 164
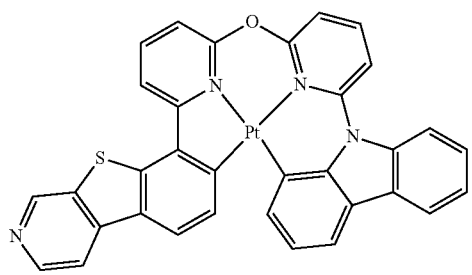
Compound 165
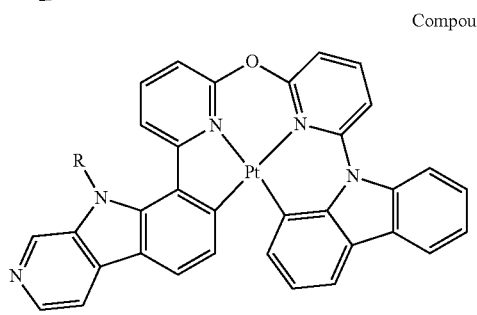
Compound 166
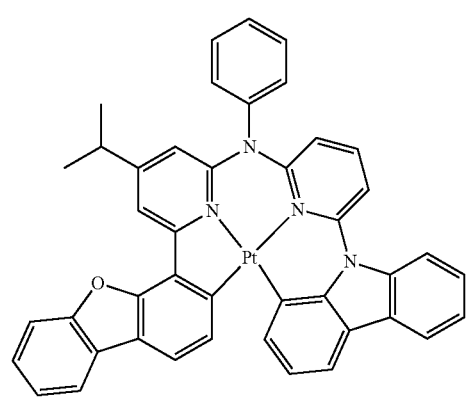
Compound 167
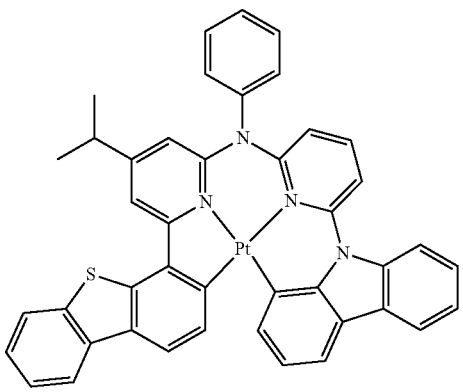
Compound 168
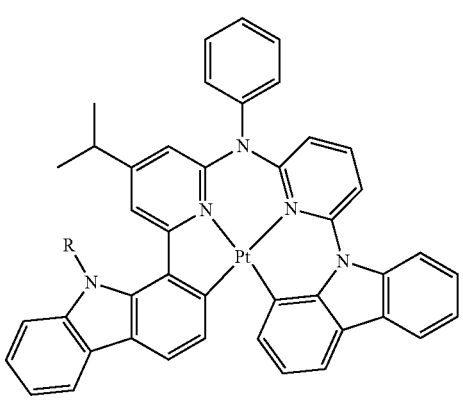
Compound 169
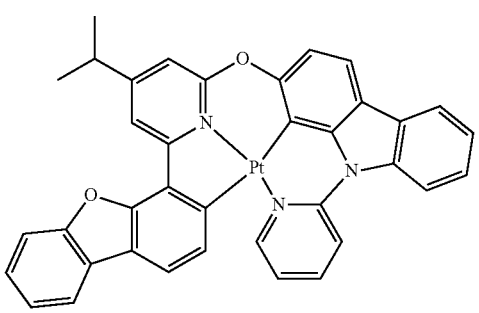
Compound 170
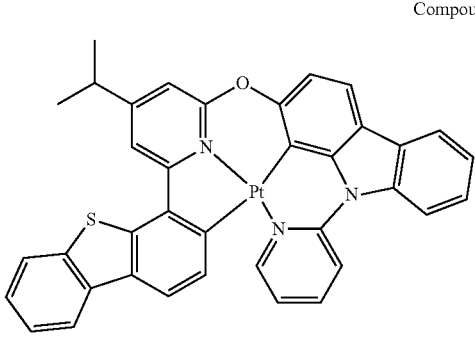

Compound 171
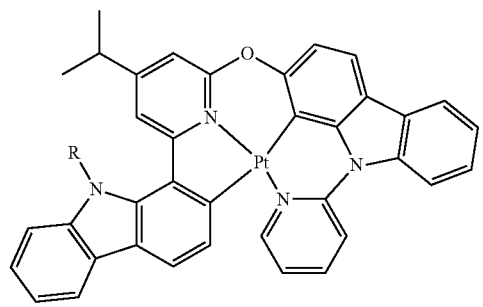
Compound 172
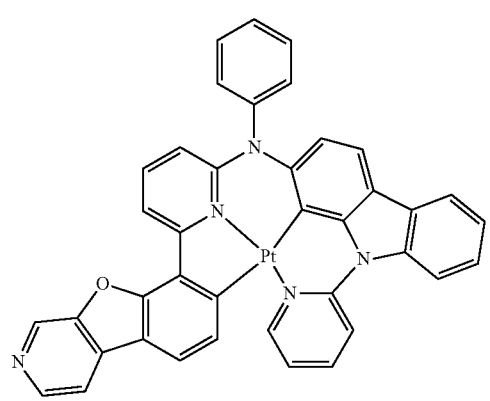
Compound 173
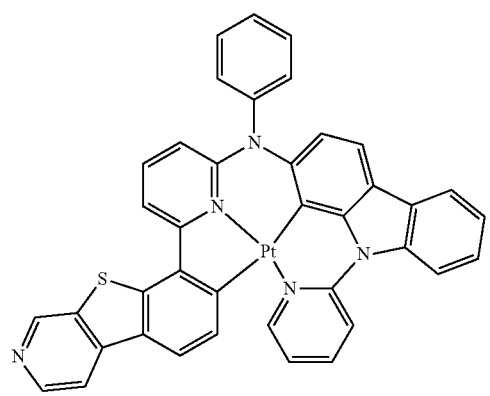
Compound 174
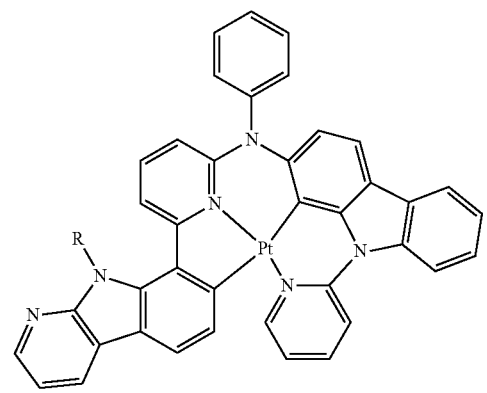
Compound 175
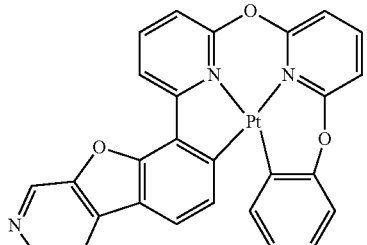
Compound 176
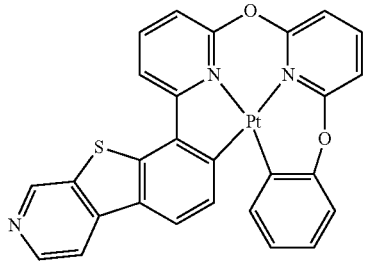
Compound 177
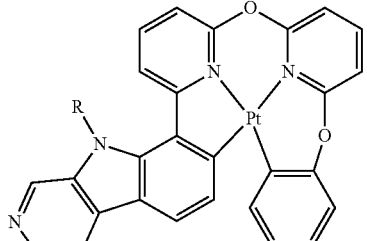
Compound 178
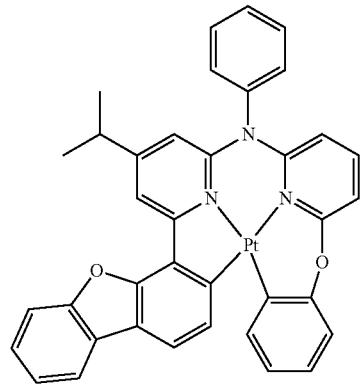
Compound 179
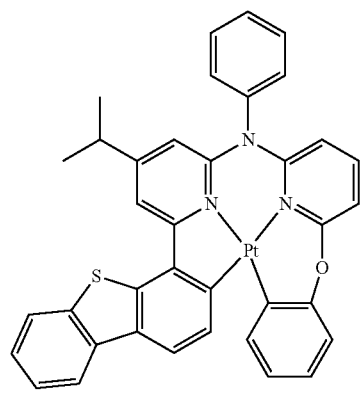

Compound 180
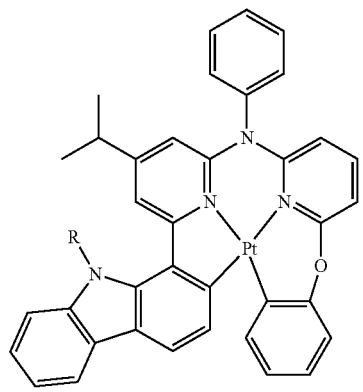
Compound 181
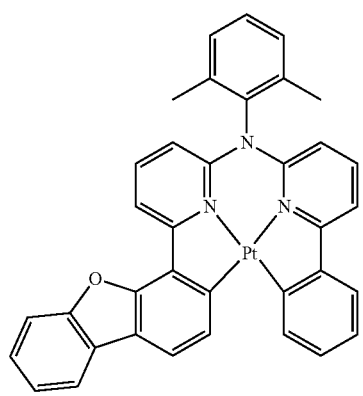
Compound 182
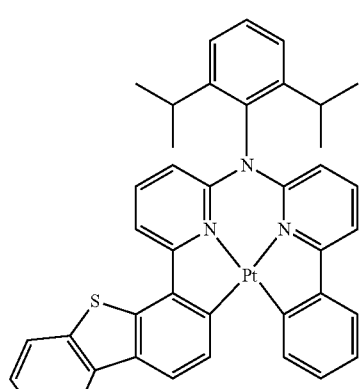
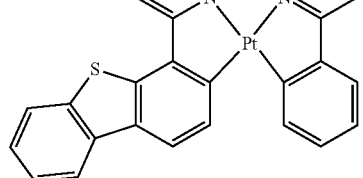
Compound 183
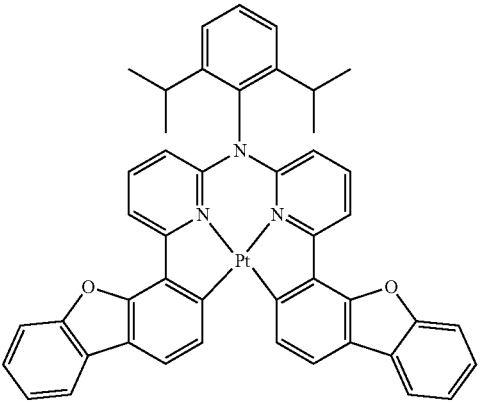
Compound 184
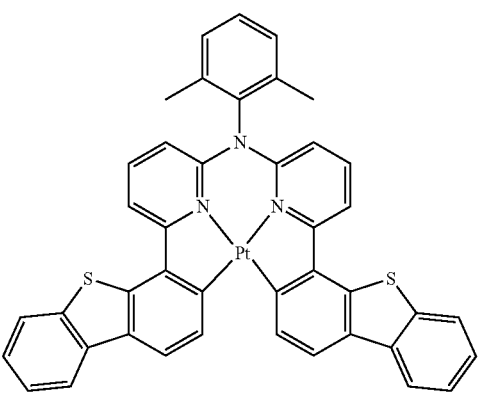
Compound 185
Compound 186
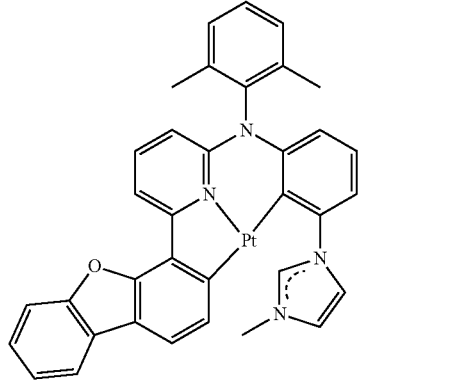

In Compounds 1-186, when R is present it can be hydrogen, deuterium, halide, alkyl, cycloalkyl, heteroalkyl, arylalkyl, aryl, heteroaryl, acyl and combinations thereof.

A first device is provided. The first device comprises a first organic light emitting device, further comprising an anode, a cathode, and an organic layer, disposed between the anode and the cathode, comprising a compound having the formula:

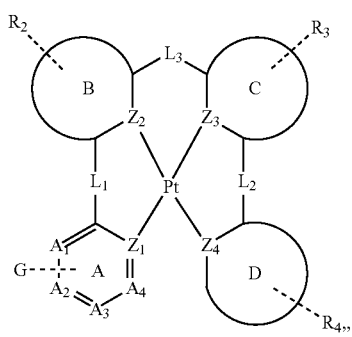

Formula I is provided, wherein G has the structure

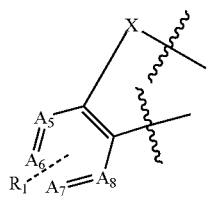

and wherein G is fused to any two adjacent carbon atoms on ring A. Ring B, ring C, and ring D are 5- or 6-membered carbocyclic or heterocyclic aromatic rings. $L_1$, $L_2$, and $L_3$ are independently selected from the group consisting of a single bond, BR, NR, PR, O, S, Se, C=O, S=O, $SO_2$, CRR', SiRR', and GeRR'. At least one of $L_1$, $L_2$, and $L_3$ is not a single bond, and X is selected from the group consisting of BR, NR, PR, O, S, Se, C=O, S=O, $SO_2$, CRR', SiRR', and GeRR', $Z_1$, $Z_2$, $Z_3$, and $Z_4$ are nitrogen or carbon atoms, and $A_1$, $A_2$, $A_3$, $A_4$, $A_5$, $A_6$, $A_7$, and $A_8$ comprise carbon or nitrogen, $R_1$, $R_2$, $R_3$, and $R_4$ independently represent mono-, di-, tri-, or tetra-substitution, wherein $R_1$ is optionally fused, $R_2$ is optionally fused to ring B, $R_3$ is optionally fused to ring C, and $R_4$ is optionally fused to ring D. R, R', $R_1$, $R_2$, $R_3$, and $R_4$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one embodiment, the first device is a consumer product. In another embodiment, the first device is an organic light-emitting device. In one embodiment, the first device comprises a lighting panel. In one embodiment, the organic layer is an emissive layer and the compound is an emissive dopant. In another embodiment, the organic layer is an emissive layer and the compound is a non-emissive dopant.

In one embodiment, the organic layer further comprises a host. In another embodiment, the host comprises a triphenylene containing benzo-fused thiophene or benzo-fused furan, wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, CH=CH—$C_nH_{2n+1}$, C≡$CC_nH_{2n+1}$, $Ar_1$, $Ar_1$—$Ar_2$, $C_nH_{2n}$—$Ar_1$, or no substitution, wherein $Ar_1$ and $Ar_2$ are independently selected from the group consisting of benzene, biphenyl, naphthalene, triphenylene, carbazole, and heteroaromatic analogs thereof, and n is from 1 to 10.

In one embodiment, the host has the formula

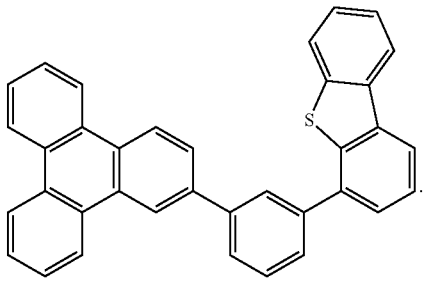 [SMILES: c1cc(-c2ccc3c4ccccc4c4ccccc4c3c2)cc(-c2cccc3c2sc2ccccc23)c1]

In another embodiment, the host is selected from the group consisting of

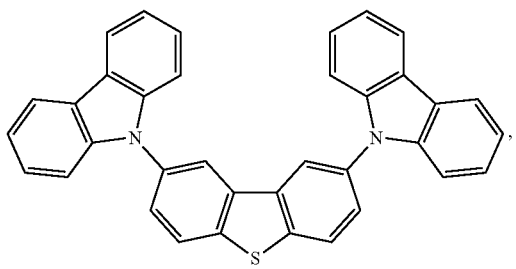

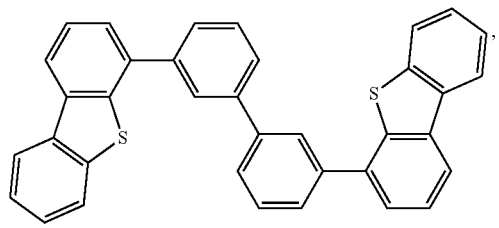

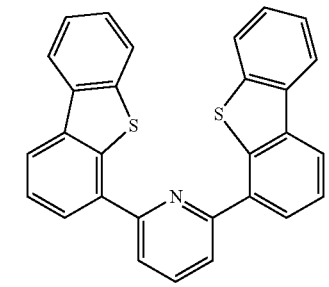

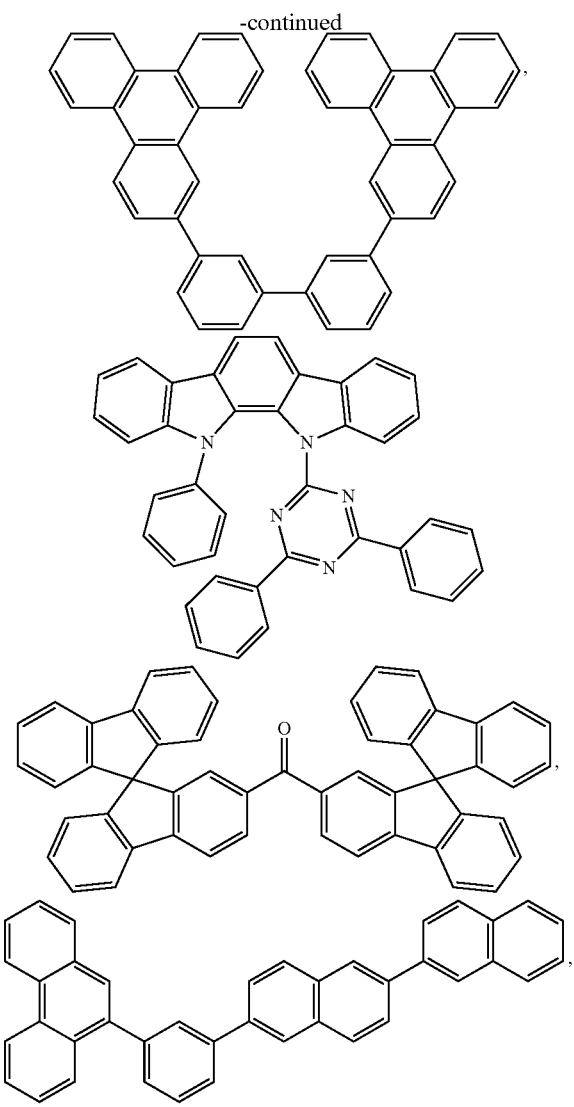

and combinations thereof.

In one embodiment, the host is a metal complex.

Figure 4:
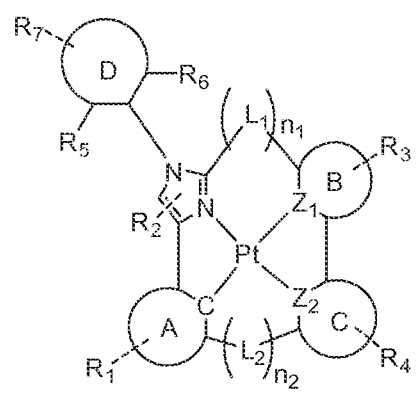
FIG. 4 shows a compound of Formula I'.

A novel class of tetradentate platinum (II) compounds are provided (as illustrated in FIG. 4). The compounds comprise: (i) two ligands that each contain at least one 5-membered carbocyclic or heterocyclic ring, (ii) one of the ligands comprises an imidazole ring with a twisted aryl group attached at N–1, and (iii) in the same ligand as the imidazole, a 6-membered carbocyclic or heterocyclic ring that is attached to the platinum via a carbon atom. These properties, taken together, may make the compounds particularly suitable for use in an OLED.

Although the first demonstrated PHOLED contained a platinum complex, namely 2,3,7,8,12,13,17,18-octaethyl-21H,23H-porphine platinum (II) (PtOEP), platinum complexes have not found any practical use in state-of-the-art PHOLEDs. (*Nature*, 1998, 395, 151). Compared to iridium complexes, platinum(II) complexes generally have a relatively long excited state lifetime and a lower quantum yield. In addition, platinum (II) complexes adopt a square planar geometry, which often causes excimer formation. Therefore, these complexes may have broadened emission spectrum at higher doping concentration in an OLED.

Bidentate and tridentate Pt (II) complexes have been reported, but, generally, these compounds have limited application in OLEDs. These complexes often have poor thermal stability and device stability, thereby limiting their application in OLEDs.

Tetradentate Pt(II) complexes have also been disclosed in literature, but, similar to the bidentate and tridentate Pt(II) complexes, these tetradentate Pt(II) complexes may have limited use in OLEDs.

As discussed above, the tetradentate platinum (II) complexes provided herein have several beneficial characteristics. First, the compounds comprise two ligands that each contain a 5-membered carbocyclic or heterocyclic ring. The first ligand comprises an imidazole ring and ring A. The second ligand comprises ring B and ring C, and one of ring B and ring C must be a 5-membered carbocyclic or heterocyclic ring. The other of ring B and ring C may be either a 5 or 6-membered carbocyclic or heterocyclic ring. Preferably, ring A and one of ring B and ring C is a 6-membered carbocyclic or heterocyclic ring, i.e., each ligand contains one 5-membered ring and one 6-membered ring. Without being bound by theory, it is believed that the basic ligand structure may be used to tune the energy levels and improve triplet energy because a 5-membered ring generally has a higher triplet energy than a 6-membered ring.

Second, a ligand contains an imidazole ring with a twisted aryl attached to N–1 of the imidazole (illustrated in FIG. 4). By incorporating a twisted aryl moiety into the tetradentate architecture, the Pt(II) complexes may demonstrate higher stability and, thus, provide longer device lifetimes. Without being bound by theory, it is believed that twisting the aryl group out of the plane of the imidazole ring, thus breaking the conjugation and making the compound less planar, may result in bluer emission, improved sublimation and improved efficiency. Specifically, the compounds may be less prone to triplet-triplet annihilation and self-quenching, because they have more three-dimensional character.

Third, ring A of the first ligand is attached to the platinum via a carbon atom. Without being bound by theory, it is believed that such a ligand system may provide high triplet.

Taken together, the features of these compounds may provide beneficial properties that make these compounds particularly suitable for use in OLEDs. For example, the compounds may provide improved blue emission, improved stability and improved efficiency.

Cyclometallated tetradentate Pt(II) compounds comprising an imidazole ring with a twisted aryl group are provided. The compounds have the formula:

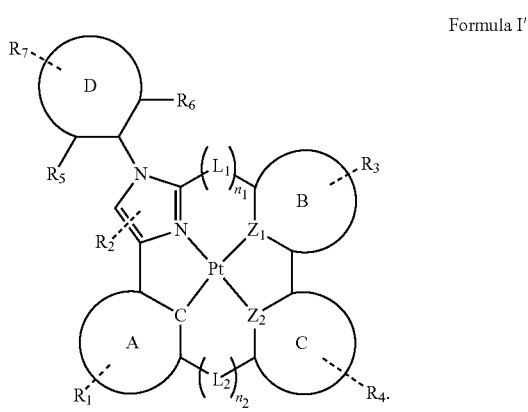

Formula I'

Ring A, ring B, ring C and ring D are each independently a 5- or 6-membered carbocyclic or heterocyclic ring. $L_1$ and $L_2$ are independently selected from the group consisting of a single bond, BR, NR, O, Se, C=O, S=O, $SO_2$, CRR', SiRR', and GeRR'. $n_1$ is 0 or 1. $n_2$ is 0 or 1. $n_1+n_2$ is at least equal to 1. $Z_1$ and $Z_2$ are independently a nitrogen atom or a carbon atom. $R_1$, $R_2$, $R_3$, $R_4$, and $R_7$ may represent mono-, di-, tri-, or tetra-substitutions. $R_1$ is optionally fused to ring A. $R_3$ is optionally fused to ring B. $R_4$ is optionally fused to ring C. $R_7$ is optionally fused to ring D. $R_3$ and $R_4$ are optionally joined to form into a ring. At least one of ring B and ring C is a 5-membered carbocyclic or heterocyclic ring. $R_1$, $R_2$, $R_3$, $R_4$, $R_5$, $R_6$, and $R_7$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. At least one of $R_5$ and $R_6$ is not hydrogen or deuterium.

When $n_1$ or $n_2$ is equal to 0, there is no connection, i.e., no single bond or other substitution at $L_1$ or $L_2$. Compounds 1'-3' are non-limiting examples of compounds where $n_1$ is 0. Alternatively, Compounds 26'-28' are non-limiting examples of compounds where $n_2$ is 0.

In one embodiment, at least one of $R_5$ and $R_6$ is an alkyl. In another aspect, at least one of $R_5$ and $R_6$ is an alkyl containing at least 3 carbons. In yet another aspect, at least one of $R_5$ and $R_6$ is a cycloalkyl.

In one embodiment, each of $R_5$ and $R_6$ is an aryl.

In one embodiment, $R_3$ or $R_4$ is a substituted aryl. In another embodiment, $R_3$ or $R_4$ is a 2,6-disubstituted aryl.

Preferably, $R_3$ or $R_4$ is

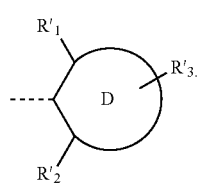

$R'_1$ and $R'_2$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. At least one of $R'_1$ and $R'_2$ is not hydrogen or deuterium. D is 5-membered or 6-membered carbocyclic or heterocyclic ring that is optionally further substituted with $R'_3$. $R'_3$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the compound has the formula:

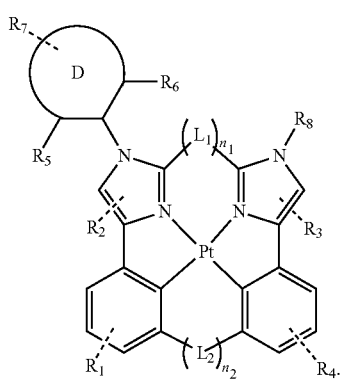

Formula II'

$R_8$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In another embodiment, the compound has the formula:

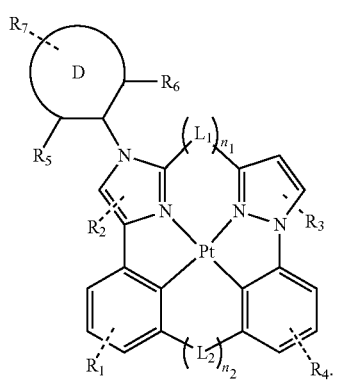

Formula III'

In yet another embodiment, the compound has the formula:

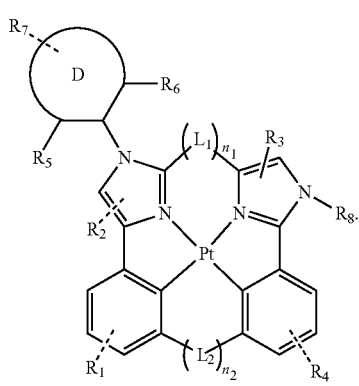

Formula IV'

$R_8$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In a further embodiment, the compound has the formula:

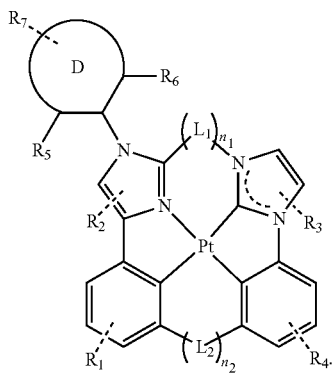

Formula V'

In another embodiment, the compound has the formula:

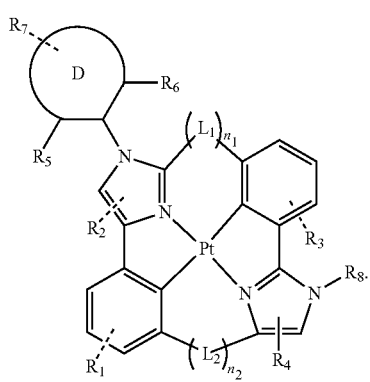

Formula VI'

$R_8$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In yet another embodiment, the compound has the formula:

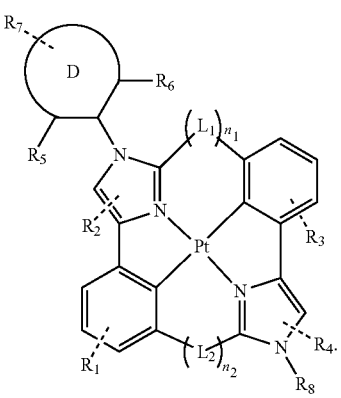

Formula VII'

$R_8$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In another embodiment, the compound has the formula:

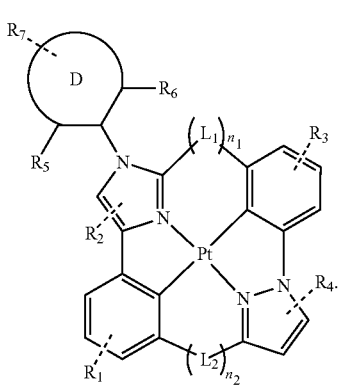

Formula VIII'

In yet another embodiment, the compound has the formula:

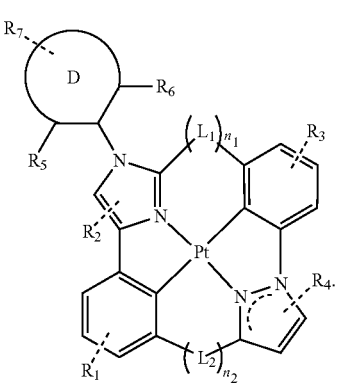

Formula IX'

Specific examples of cyclometallated tetradentate Pt(II) compounds comprising an imidazole ring with a twisted aryl group are provided. In one aspect, the compound is selected from the group consisting of:
Compound 1'
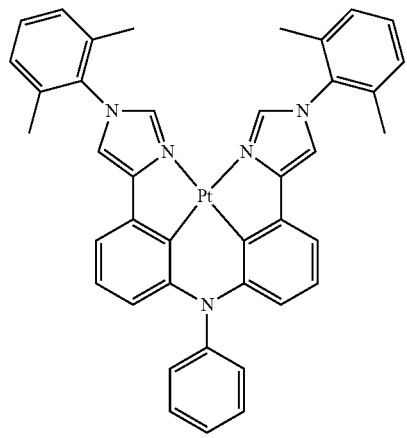
Compound 2'
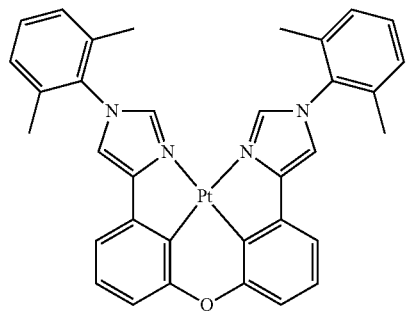
Compound 3'
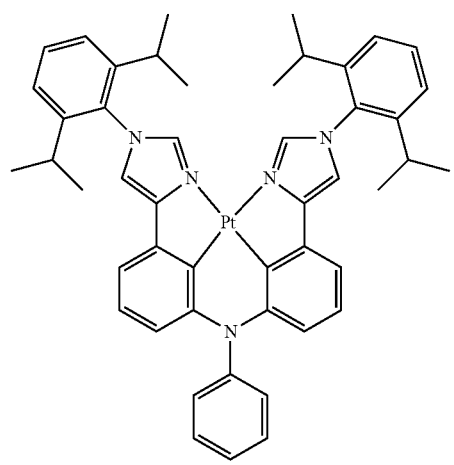
Compound 4'
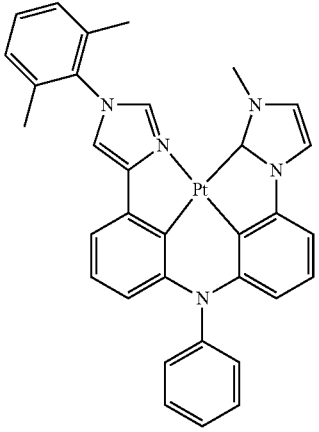
Compound 5'
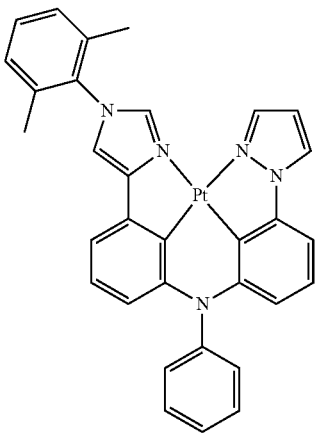
Compound 6'
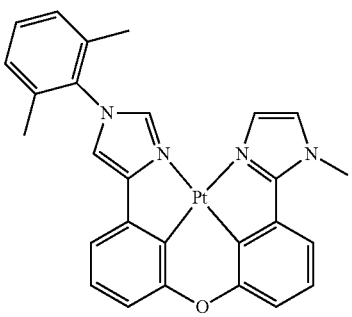

Compound 7'
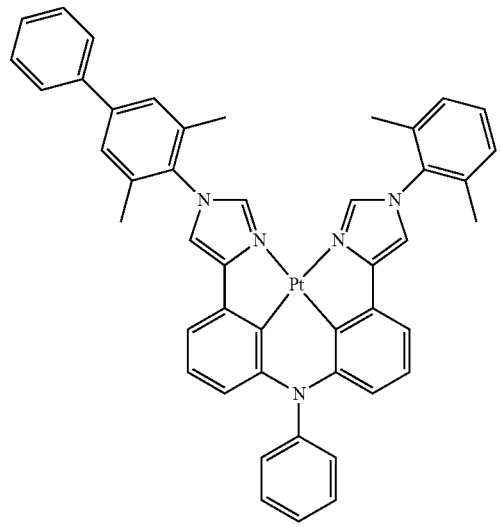
Compound 8'
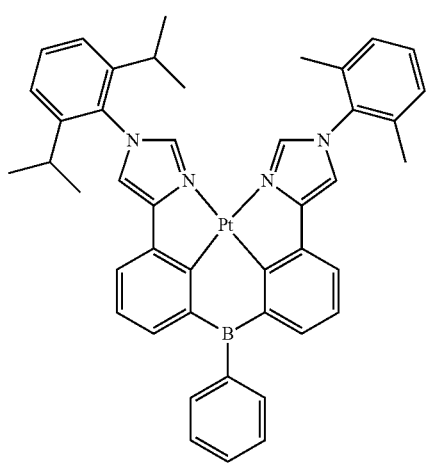
Compound 9'
Compound 10'
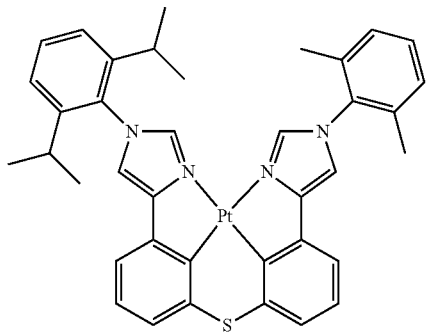
Compound 11'
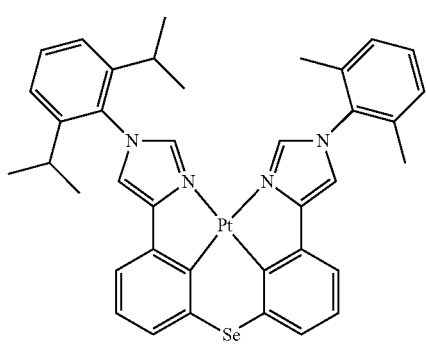
Compound 12'
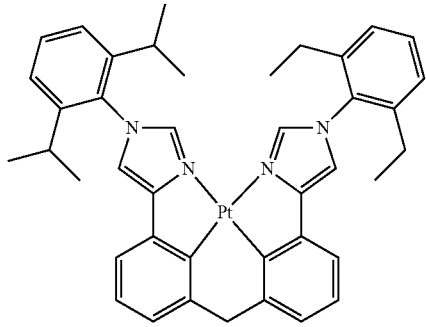
Compound 13'
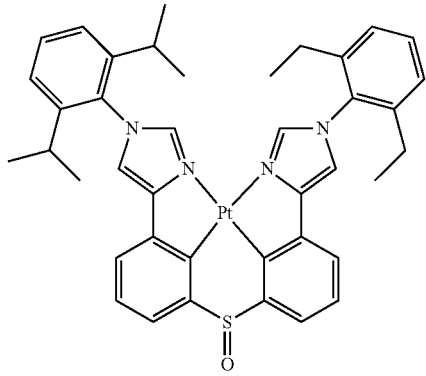

Compound 14'
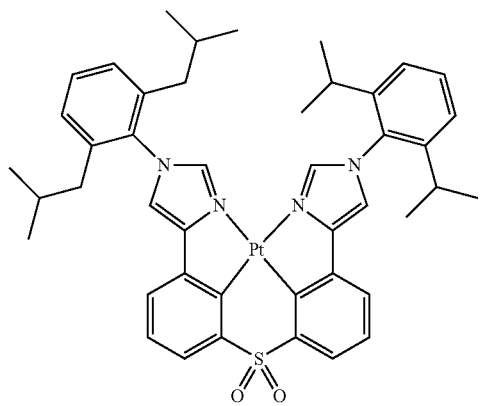
Compound 15'
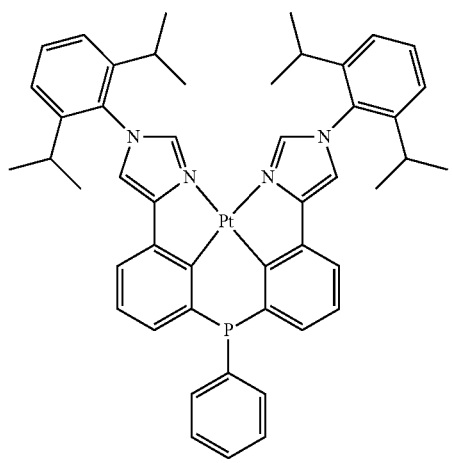
Compound 16'
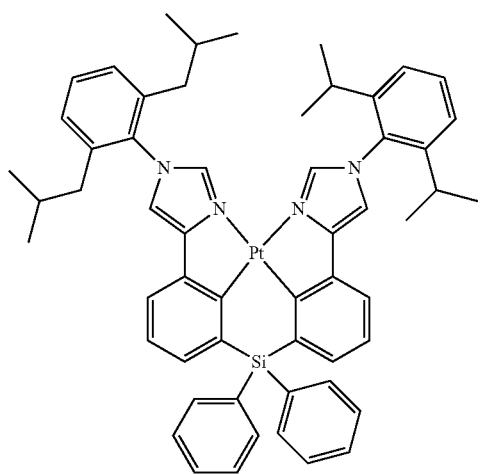
Compound 17'
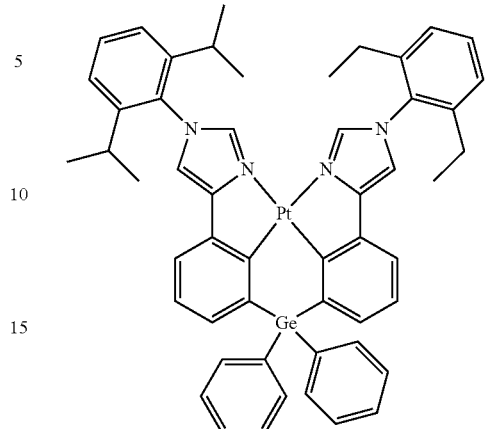
Compound 18'
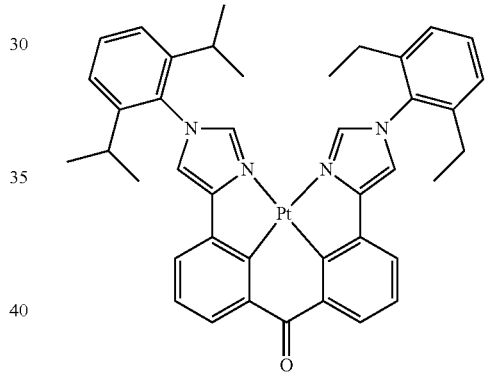
Compound 19'
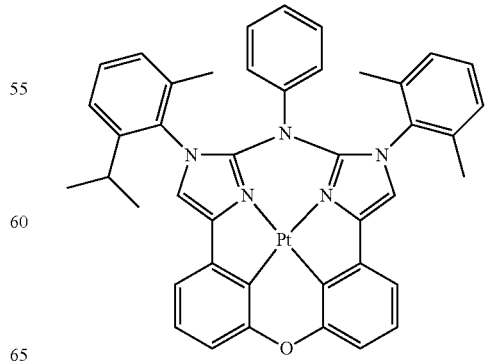

-continued
Compound 20'
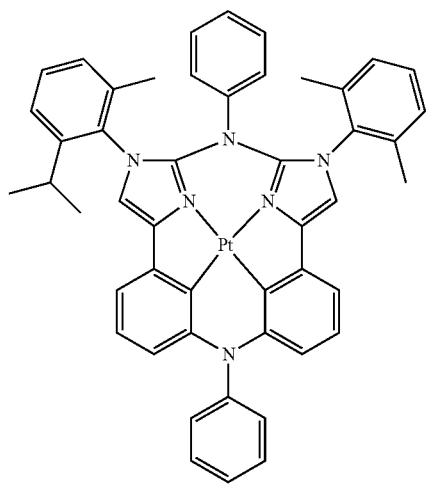
Compound 21'
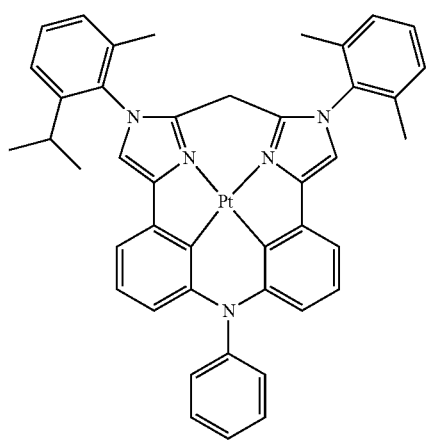
Compound 22'
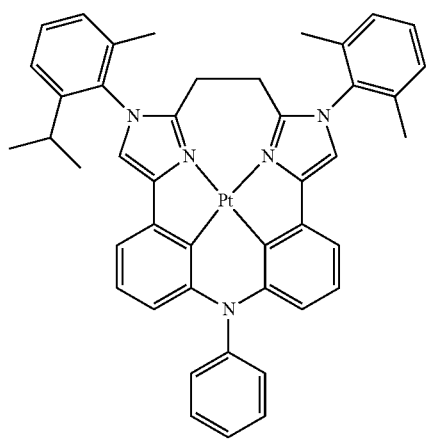
Compound 23'
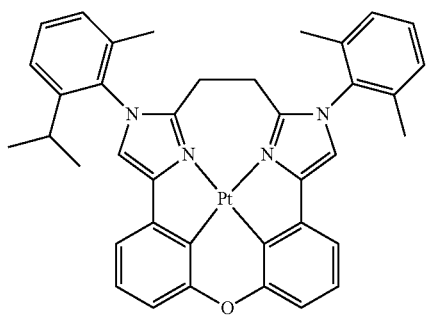
Compound 24'
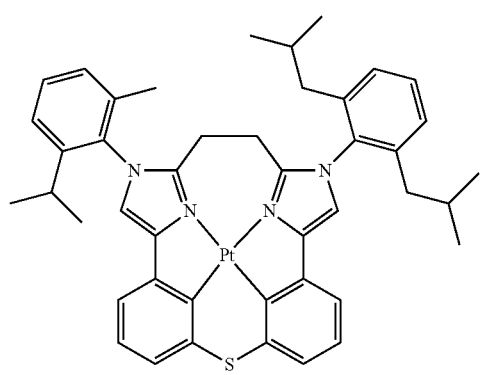
Compound 25'
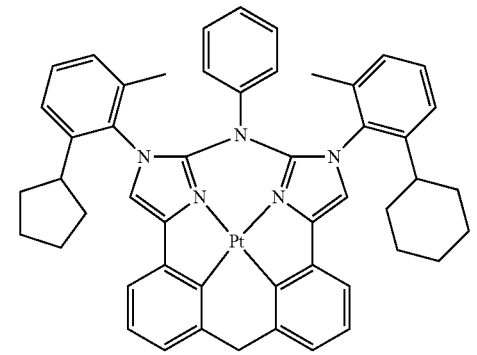
Compound 26'

Compound 27'
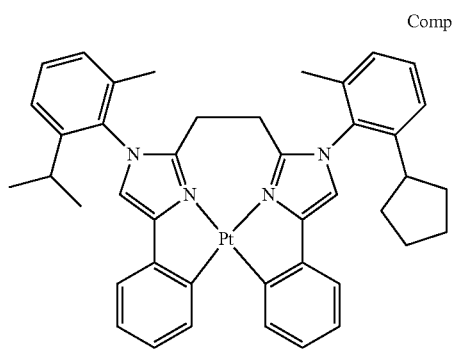
Compound 31'
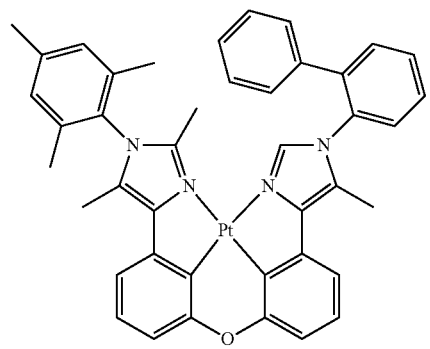
Compound 28'
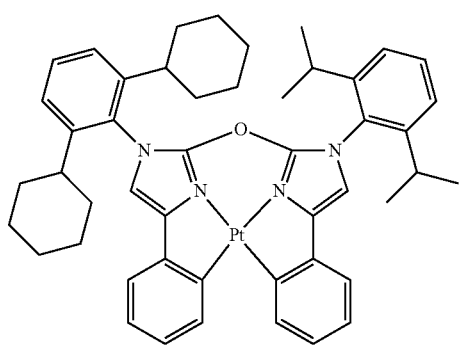
Compound 32'
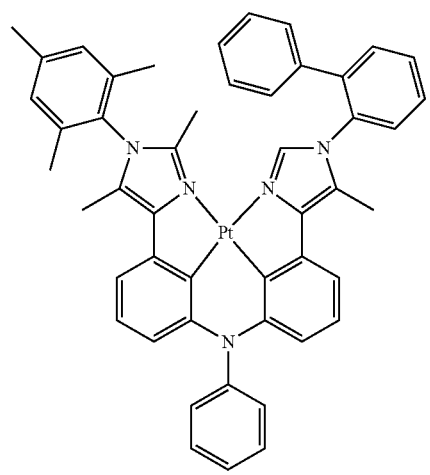
Compound 29'
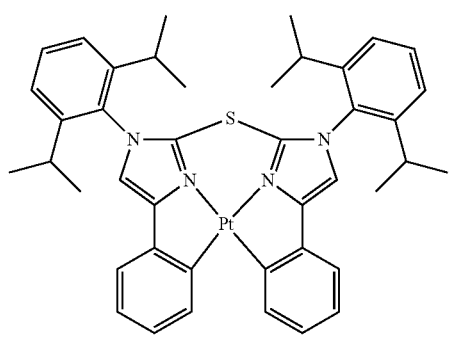
Compound 33'
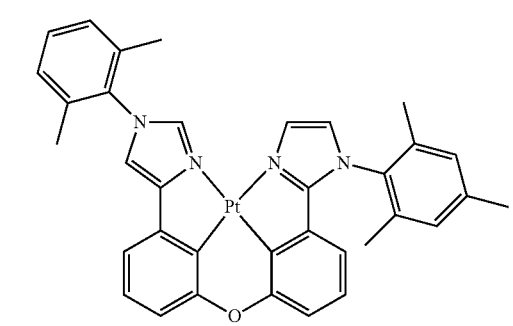
Compound 30'
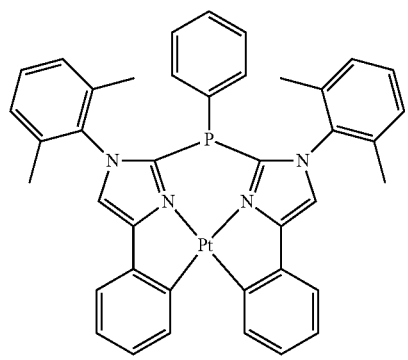
Compound 34'
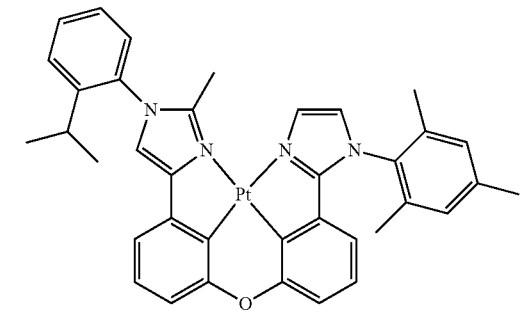

Compound 35'
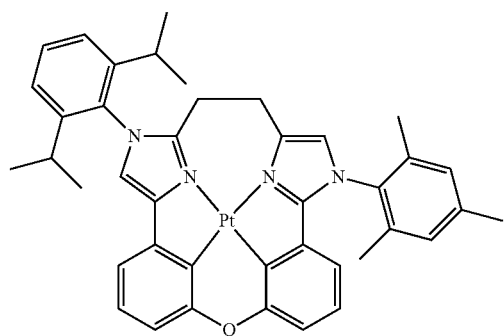
Compound 36'
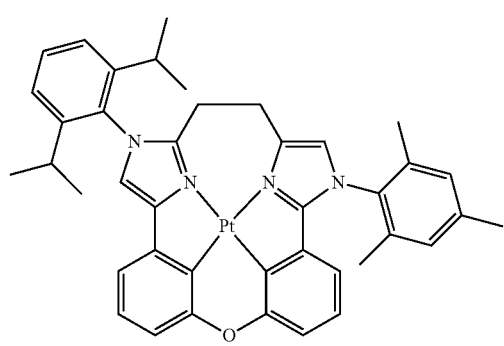
Compound 37'
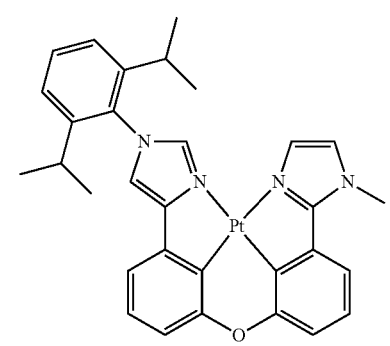
Compound 38'
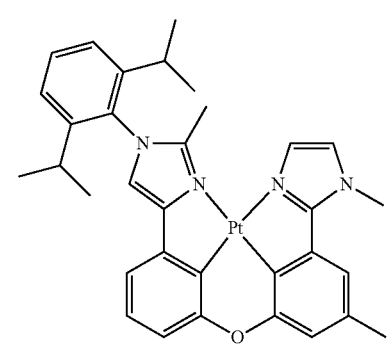
Compound 39'
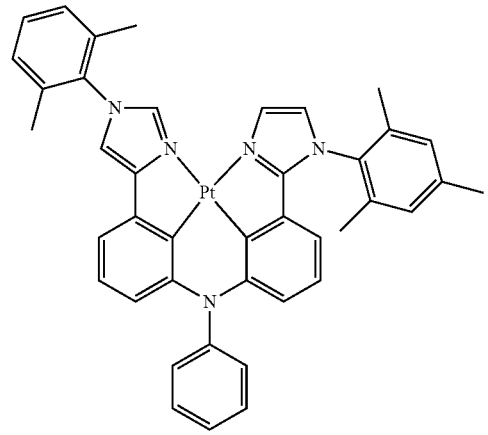
Compound 40'
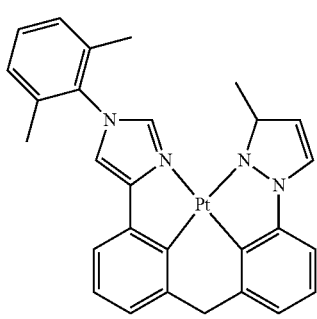
Compound 41'
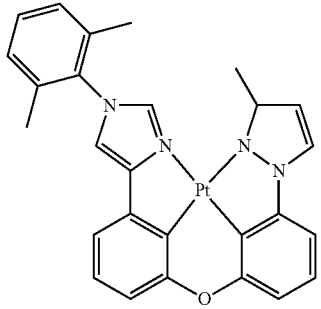
Compound 42'
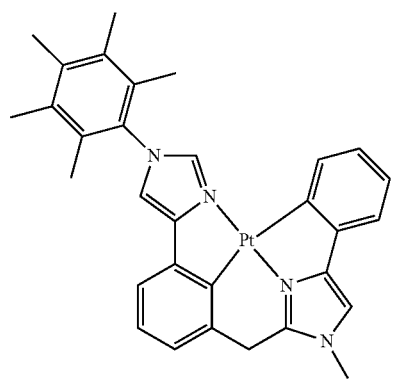

Compound 43'
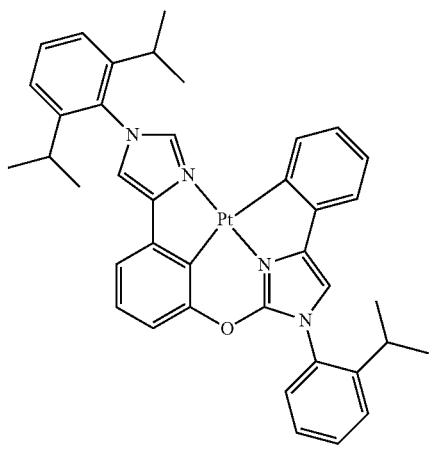
Compound 44'
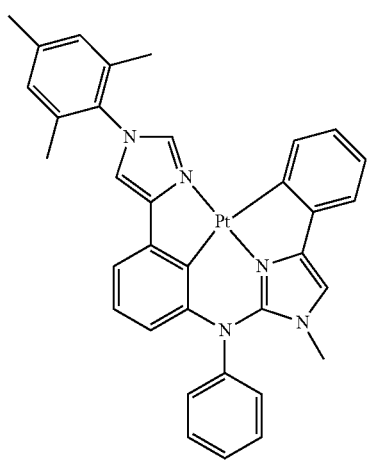
Compound 45'
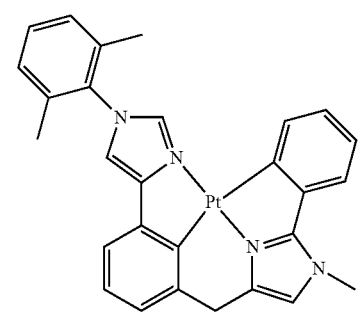
Compound 46'
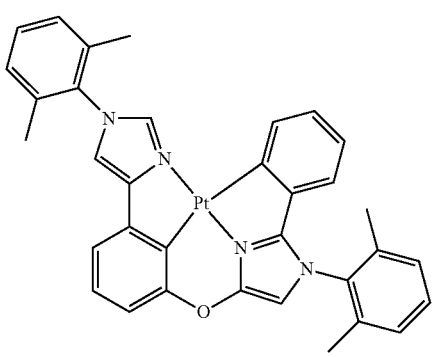
Compound 47'
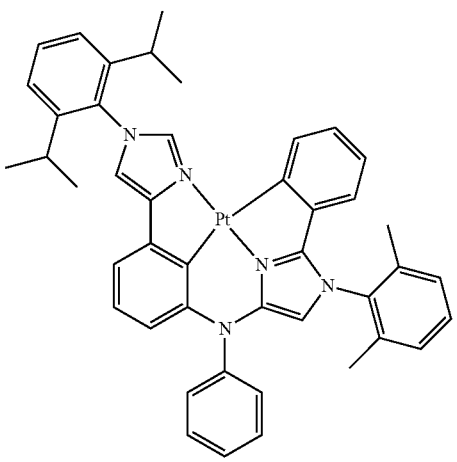
Compound 48'
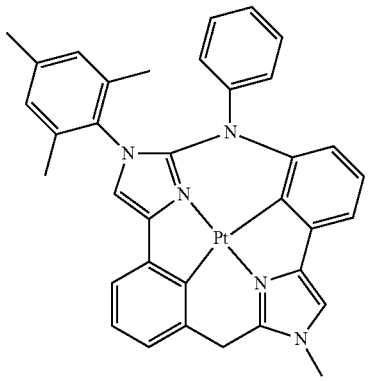
Compound 49'
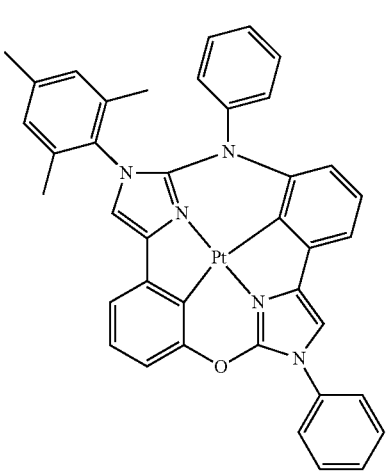

Compound 50'
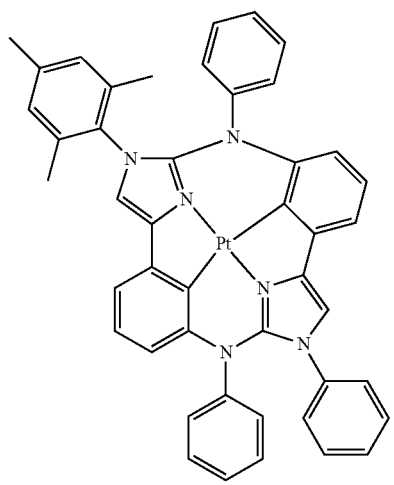
Compound 51'
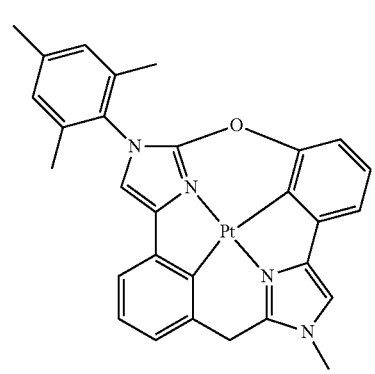
Compound 52'
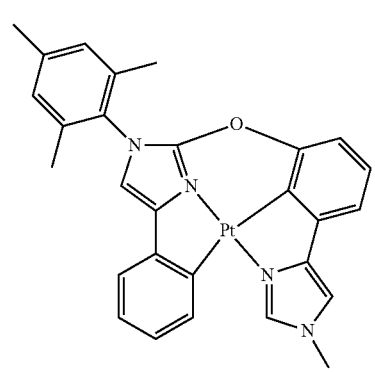
Comound 53'
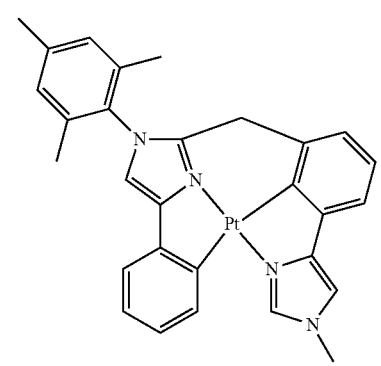
Compound 54'
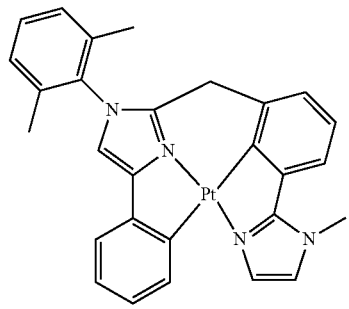
Compound 55'
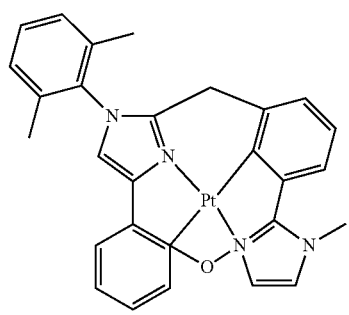
Compound 56'
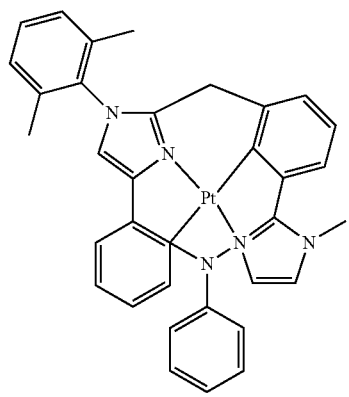
Compound 57'
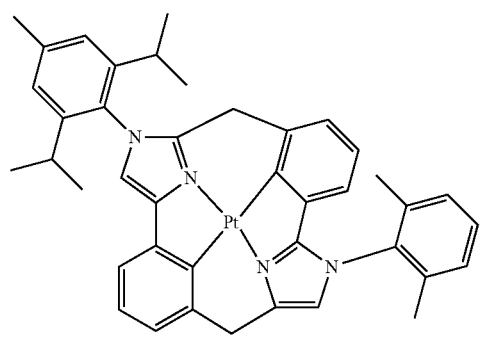

-continued

Compound 58'
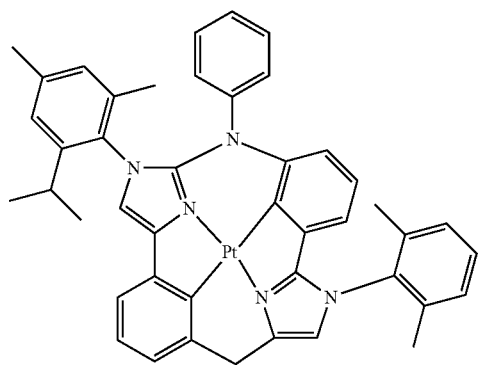

Compound 59'
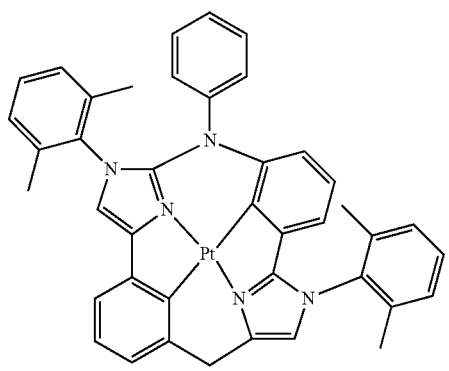

Compound 60'
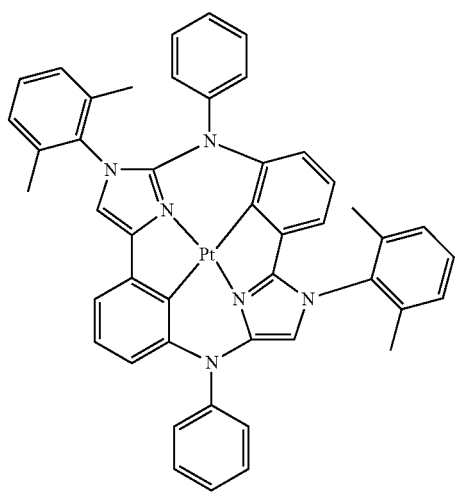

Compound 61'
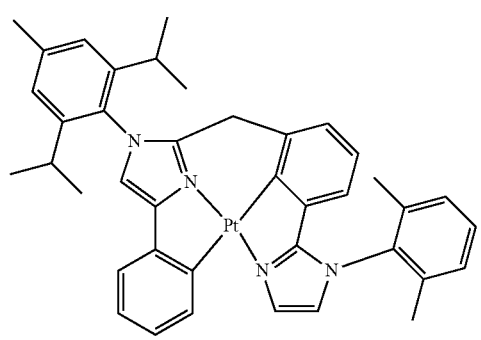

-continued

Compound 62'
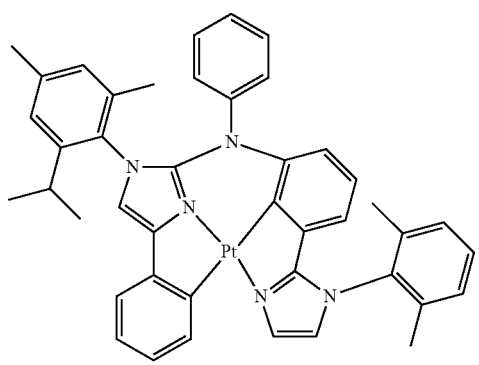

Compound 63'
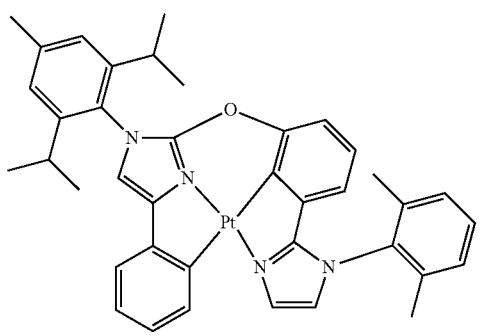

Compound 64'
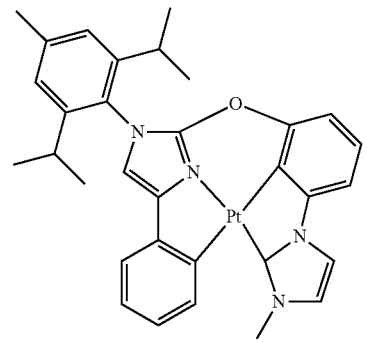

Compound 65'
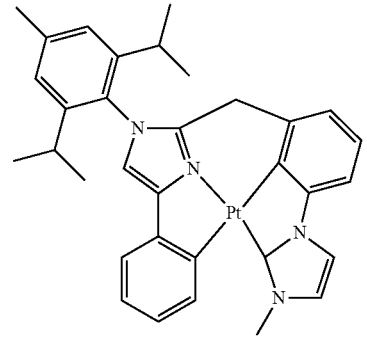

Additionally, a first device comprising an organic light emitting device is provided. The organic light emitting device further comprises an anode, a cathode, and an organic layer. The organic layer is disposed between the anode and the cathode, and it comprises a compound having the formula:

Formula I

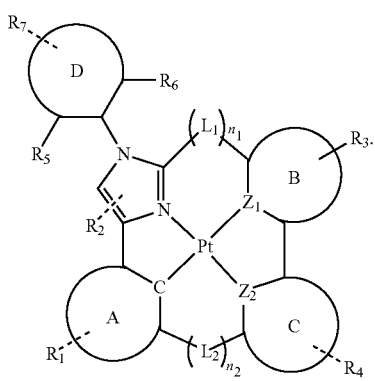

Ring A, ring B, ring C and ring D are each independently a 5- or 6-membered carbocyclic or heterocyclic ring. $L_1$ and $L_2$ are independently selected from the group consisting of a single bond, BR, NR, O, Se, C=O, S=O, $SO_2$, CRR', SiRR', and GeRR'. $n_1$ is 0 or 1. $n_2$ is 0 or 1. $n_1+n_2$ is at least equal to 1. $Z_1$ and $Z_2$ are independently a nitrogen atom or a carbon atom. $R_1$, $R_2$, $R_3$, $R_4$, and $R_7$ may represent mono-, di-, tri-, or tetra-substitutions. $R_1$ is optionally fused to ring A. $R_3$ is optionally fused to ring B. $R_4$ is optionally fused to ring C. $R_7$ is optionally fused to ring D. $R_3$ and $R_4$ are optionally joined to form into a ring. At least one of ring B and ring C is a 5-membered carbocyclic or heterocyclic ring. $R_1$, $R_2$, $R_3$, $R_4$, $R_5$, $R_6$, and $R_7$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. At least one of $R_5$ and $R_6$ is not hydrogen or deuterium.

The various specific embodiments discussed above for compounds having Formula I' are also applicable to a compound having Formula I' that is used in the first device. In particular, specific aspects of ring A, ring B, ring C, ring D, $L_1$, $L_2$, $n_1$, $n_2$, $R_1$, $R_2$, $R_3$, $R_4$, $R_5$, $R_6$, $R_7$, $R'_1$, $R'_2$, $R'_3$, Formulas II'-IX', and Compounds 1'-65' of the compound having Formula I' are also applicable to a compound having Formula I' that is used in a device.

In one embodiment, the organic layer is an emissive layer and the compound is an emissive dopant.

In one embodiment, the organic layer further comprises a host. In another embodiment, the host comprises a triphenylene containing benzo-fused thiophene or benzo-fused furan, and any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, CH=CH—$C_nH_{2n+1}$, C≡$CC_nH_{2n+1}$, $Ar_1$, $Ar_1$—$Ar_2$, $C_nH_{2n}$—$Ar_1$, or no substitution. n is from 1 to 10. $Ar_1$ and $Ar_2$ are independently selected from the group consisting of benzene, biphenyl, naphthalene, triphenylene, carbazole, and heteroaromatic analogs thereof.

In one embodiment, the host has the formula:

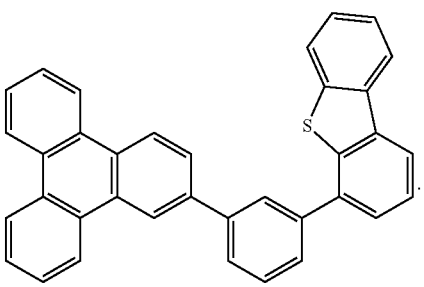

In another embodiment, the host is selected from the group consisting of:

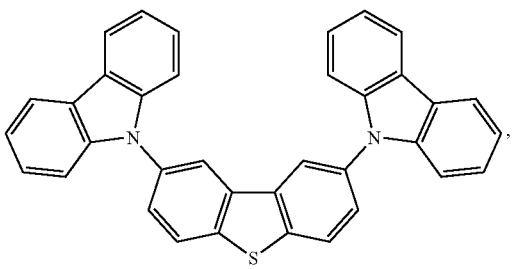

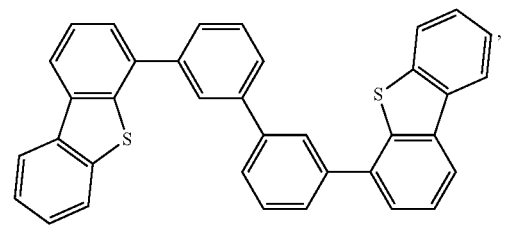

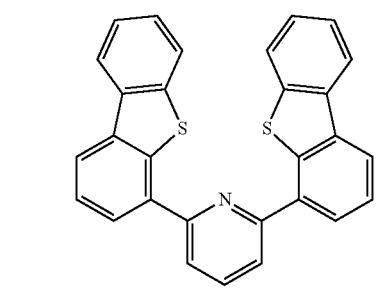

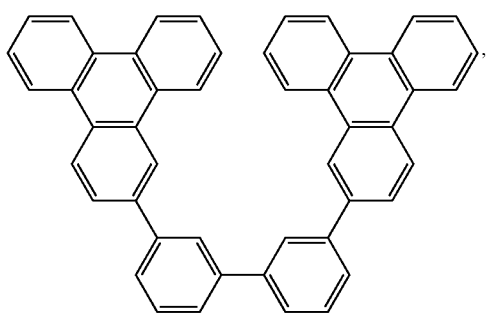

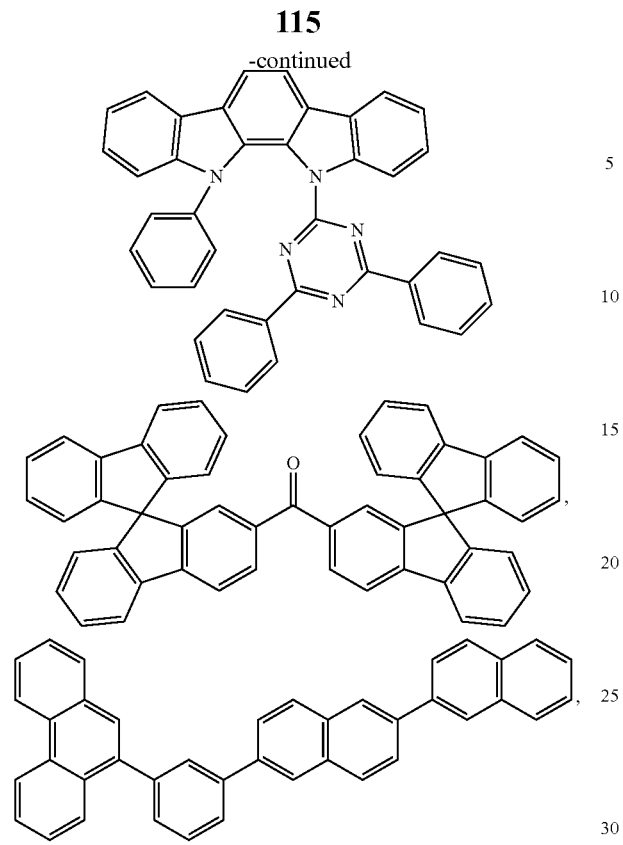

and combinations thereof.

In yet another embodiment, the host is a metal complex.

In one embodiment, the organic layer is an emissive layer and the compound is a non-emissive dopant.

In one embodiment, the first device is a consumer product. In another embodiment, the first device is an organic light emitting device. In yet another embodiment, the first device comprises a lighting panel.

Device Examples

All device examples were fabricated by high vacuum (<10-7 Torr) thermal evaporation (VTE). The anode electrode is 800 Å or 1200 Å of indium tin oxide (ITO). The cathode consisted of 10 Å of LiF followed by 1000 Å of Al. All devices were encapsulated with a glass lid sealed with an epoxy resin in a nitrogen glove box (<1 ppm of $H_2O$ and $O_2$) immediately after fabrication, and a moisture getter was incorporated inside the package.

In some devices, the organic stack of the devices consisted of sequentially, from the ITO surface, 100 Å of Compound A as the hole injection layer (HIL), 300 Å of 4,4'-bis[N-(1-naphthyl)-N-phenylamino]biphenyl (α-NPD) as the hole transporting later (HTL), 300 Å of Compound B doped with Compound 4 as the emissive layer (EML), 50 Å of Compound B as BL, and 450 Å of Alq as the ETL. Comparative Device Examples were fabricated in a manner similar to that of the Device Examples, except that Compound X was used as the emitter instead of Compound 4. The device results and data are summarized in Tables 1 and 2 from those devices. As used herein, Compound A, Compound B, Alq, α-NPD, and Compound X have the following structures:

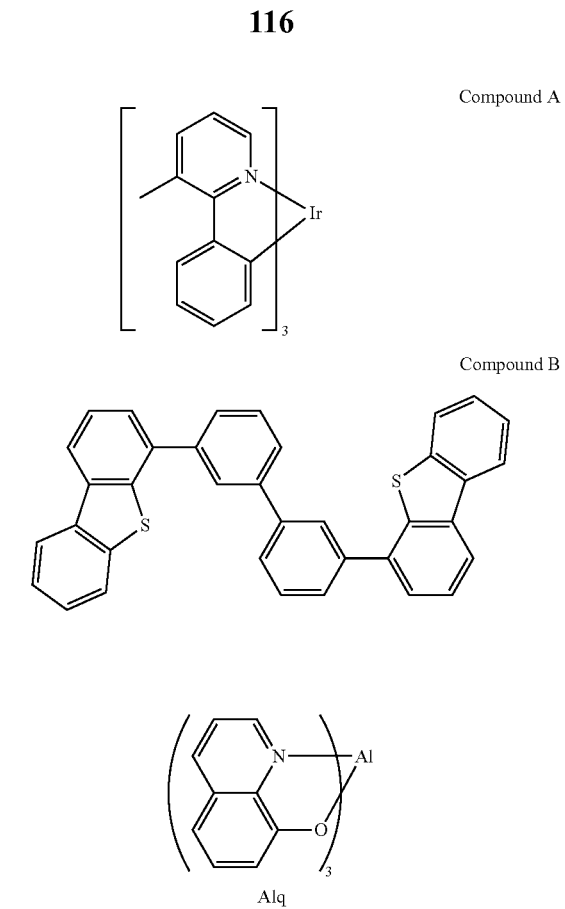

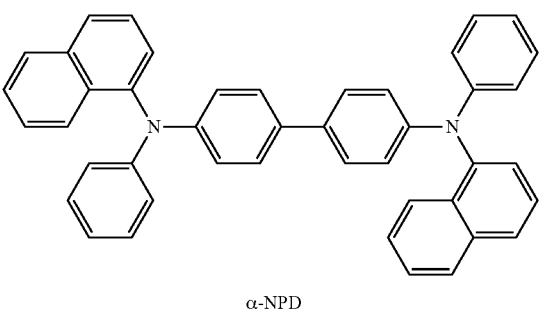

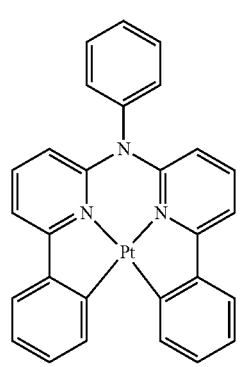

-continued

Compound 4

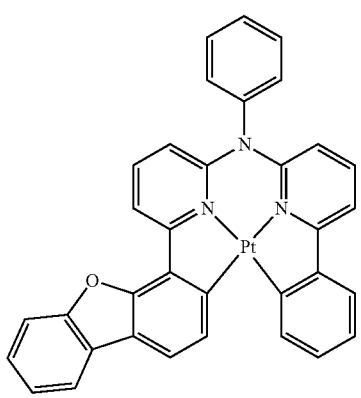

In some devices, the organic stack of the devices consisted of sequentially, from the ITO surface, 100 Å of LG101 (purchased from LG Chem) as the hole injection layer (HIL), 300 Å of either NPD or TAPC as the hole transporting layer (HTL), 300 Å of UGH3 doped with the emitter at either 15% or 20% as the emissive layer (EML), 50 Å of Compound B' as blocking layer (BL), and 300 Å of Alq or 3TPYMB as the electron transporting layer (ETL).

As used herein, the following compounds have the following structures:

Compound B'

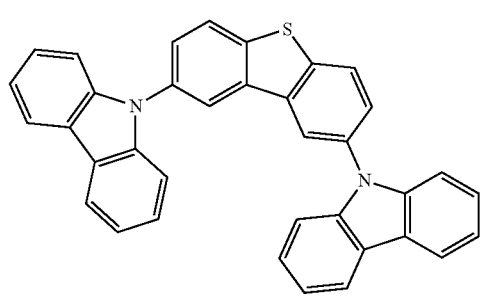

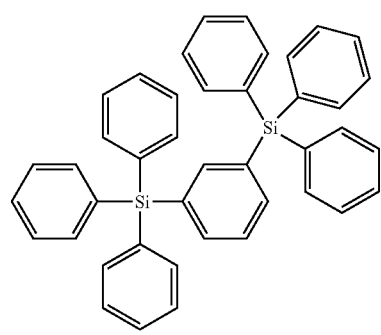

UGH3

-continued

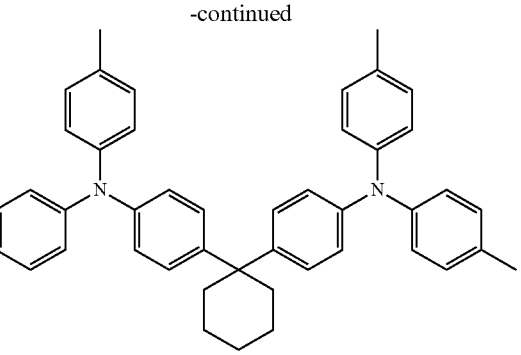

TAPC

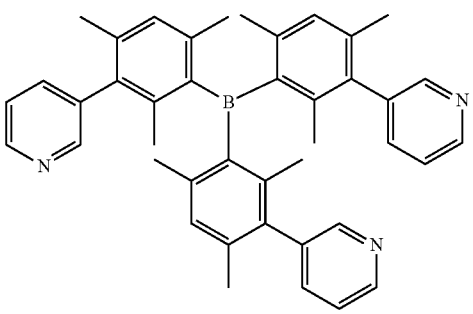

3TPYMB

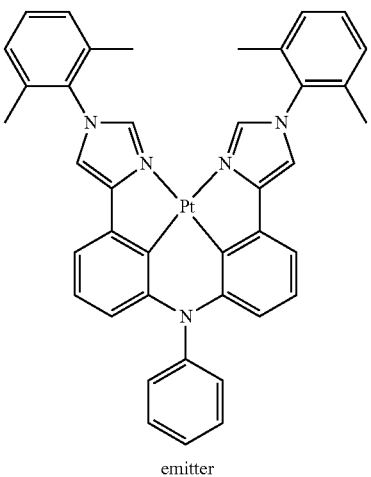

emitter

The device examples are detailed in Table 3, and the corresponding device data is summarized in Table 4.

TABLE 1

VTE Phosphorescent OLEDs

| Example | HIL | HTL | EML (doping %) | | BL | ETL |
|---|---|---|---|---|---|---|
| Example 1 | Compound A | NPD | Compound B | Compound 4 20% | Compound B | Alq |
| Comparative Example 1 | compound A | NPD | Compound B | Compound X 15% | Compound B | Alq |

TABLE 2

VTE Device Data

| | 1931 CIE | | | FWHM | At 1000 nits | | | | At 40 mA/cm² | |
|---|---|---|---|---|---|---|---|---|---|---|
| | | | | | Voltage | LE | EQE | PE | $L_0$ | LT80% |
| Example | x | y | $\lambda_{max}$ | (nm) | (V) | (Cd/A) | (%) | (lm/W) | (nits) | (h) |
| Example 1 | 0.422 | 0.552 | 538 | 64 | 8.4 | 10.6 | 4.0 | 4.0 | 2001 | 145 |
| Comparative Example 1 | 0.357 | 0.581 | 514 | 60 | 9.7 | 8.2 | 2.8 | 2.7 | 2989 | 58 |

OLED devices incorporating compounds of Formula have demonstrated superior properties. As a merely illustrative example, Example 1, which incorporates Compound 4 containing a dibenzofuran moiety, has a higher efficiency (10.6 Cd/A, 4.0% EQE, 4.0 lm/W) than the Comparative Example, which uses Compound X, lacking any dibenzo (DBX) fragment (9.7 Cd/A, 2.8% EQE, 2.7 lm/W). Devices incorporating Compound 4 also demonstrated a longer lifetime (145 h) in comparison to Compound X (58 h) and a lower turn-on voltage (8.4 V) versus the Comparative Example (9.7 V). These results indicate that incorporating compounds of Formula I, which bear one or more DBX groups, results in devices with highly desirable properties.

TABLE 3

VTE PHOLEDs

| Example | HIL | HTL | EML doping % | BL | ETL |
|---|---|---|---|---|---|
| 1 | LG101 | TAPC | 15 | Compound B' | 3TPYMB |
| 2 | LG101 | NPD | 15 | Compound B' | Alq |
| 3 | LG101 | TAPC | 20 | Compound B' | Alq |

TABLE 4

VTE Device Data

| | 1931 CIE | | $\lambda_{max}$ | FWHM | At 1000 nits | | | | 40 mA/cm² |
|---|---|---|---|---|---|---|---|---|---|
| | | | | | Voltage | LE | EQE | PE | Lo |
| Example | X | Y | (nm) | (nm) | (V) | (Cd/A) | (%) | lm/W | (nits) |
| 1 | 0.126 | 0.169 | 468 | 14 | 8.3 | 15.1 | 12.3 | 5.7 | 2,824 |
| 2 | 0.127 | 0.176 | 468 | 14 | 6.5 | 11.6 | 9.2 | 5.6 | 2,116 |
| 3 | 0.13 | 0.196 | 470 | 18 | 7.6 | 14.5 | 10.6 | 6 | 2,692 |

DFT calculations were used to predict the properties of inventive compounds and comparative compounds. The HOMO, LUMO, the HOMO-LUMO energy gap and triplet energies for each structure were calculated using DFT calculations with the Gaussian software package at the B3LYP/cep-31 g functional and basis set. The DFT calculations are summarized in Table 5. Ex. is an abbreviation for Example.

TABLE 5

| | | DFT Data | | | |
|---|---|---|---|---|---|
| Ex. | Structure | HOMO (eV) | LUMO (eV) | Gap (eV) | T₁ (nm) |
| 4 | Compound 1' | −4.54 | −0.97 | −3.57 | 452 |
| 5 | Compound 2' | −4.05 | −0.90 | −3.15 | 486 |
| 6 | Compound 3' | −4.04 | −0.74 | −3.31 | 493 |

TABLE 5-continued
| | | DFT Data | | | |
|---|---|---|---|---|---|
| Ex. | Structure | HOMO (eV) | LUMO (eV) | Gap (eV) | $T_1$ (nm) |
| 7 | 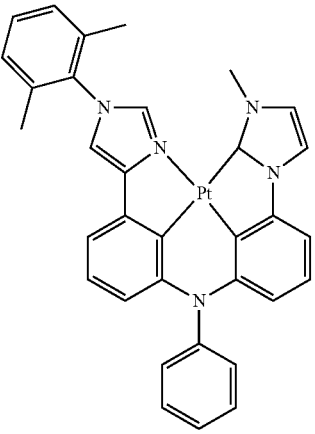<br>Compound 4' | −4.17 | −0.94 | −3.22 | 507 |
| 8 | 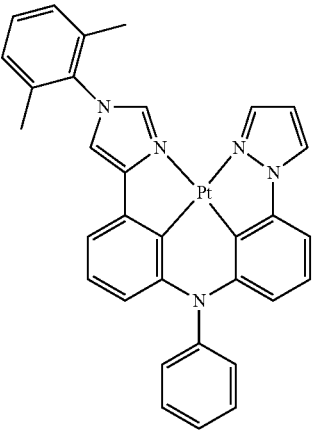<br>Compound 5' | −4.31 | −1.04 | −3.27 | 531 |
| 9 | 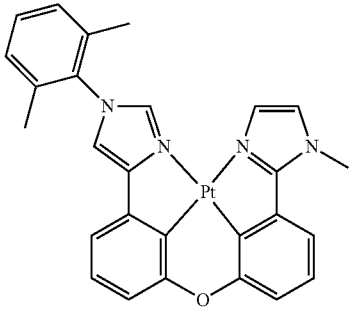<br>Compound 6' | −4.59 | −0.99 | −3.60 | 496 |

TABLE 5-continued

| | | DFT Data | | | |
|---|---|---|---|---|---|
| Ex. | Structure | HOMO (eV) | LUMO (eV) | Gap (eV) | $T_1$ (nm) |
| 10 | Compound 7' | −4.04 | −1.43 | −2.61 | 537 |
| 11 | Comparitive Compound 1' | −4.78 | −1.65 | −3.13 | 567 |
| 12 | Comparative Compound 2' | −4.55 | −1.67 | −2.88 | 566 |

TABLE 5-continued

| | | DFT Data | | | |
|---|---|---|---|---|---|
| Ex. | Structure | HOMO (eV) | LUMO (eV) | Gap (eV) | $T_1$ (nm) |
| 13 | Comparative Compound 3' | −4.09 | −1.21 | −2.88 | 527 |
| 14 | Comparative Compound 4' | −4.08 | −1.57 | −2.51 | 589 |
| 15 | Comparative Compound 5' | −4.45 | −2.24 | −2.21 | 755 |

Table 5 shows HOMO, LUMO energy levels, the HOMO-LUMO energy gap and triplet energies for a series of imidazole Pt (II) compounds comprising two ligands that each contain a 5-membered carbocyclic or heterocyclic ring, i.e., Compounds 1'-6', in comparison to compounds comprising only one ligand with a 5-membered carbocyclic or heterocyclic ring, i.e., Comparative Compounds 1' and 2'. The most common aromatic six member ring that coordinates neutrally in emissive organometallic compounds is pyridine. It can be seen in this table that replacing a six member ring with a five member heterocyclic ring offers advantages with regards to tuning the energy levels and triplet energy. For example, Comparative Compound 1' with pyridine is predicted to have a LUMO energy of −1.65 eV and a triplet of 567 nm. In all cases, when pyridine is replaced by a five member heterocyclic ring, such as imidazole, pyrazole, and imidazole-carbene, it results in a higher energy LUMO and triplet allowing for compounds with desirable blue emission.

Comparative Compounds 3' and 4' are analogous to the twisted aryl inventive Compound 2' and Compound 7'. From the data, it can be seen that compounds lacking a twisted aryl have significantly lower triplet energy, which is thought to be due to increased delocalization on the N-aryl substituent. For example, Compound 2' is calculated to have a triplet wavelength of 486 nm compared to 527 nm for Comparative Compound 3'. The effect of further delocalization on the N-aryl substituent can be minimized by employing a twisted aryl. For example, Compound 7' has a triplet wavelength of 537 nm, compared to the corresponding non-twisted compound, Comparative Compound 4', which has a triplet wavelength of 589 nm.

Comparative Compound 5' shows a tetradentate compounds with ligands similar to the inventive compounds, but ring A is bound to the platinum via a nitrogen atom. Specifically, Comparative Compound 5' contains a first ligand having a twisted aryl imidazole and a neutral pyridine, i.e., ring A, and a second ligand having an anionic imidazole and a benzene. Conversely, both 5-membered rings in the inventive compounds are neutrally bound nitrogen chelates, e.g., imidazole, and the 6-membered rings are anionic carbon chelates, e.g., phenyl. From the data, it can be seen that the inventive compounds may provide high triplet emission. For example, Comparative Compound 5' is predicted by calculation to have a profoundly low triplet energy of 755 nm.

Based on DFT calculations, the triplet transition of Comparative Compound 5' may be based on an intra-ligand charge transfer transition (ILCT) from one side of the ligand bridged by oxygen to the other. The HOMO for Comparative Compound 5' is localized predominantly on the 5-member ring anionic nitrogen chelate and phenyl ring, and the LUMO is localized on the neutrally coordinated pyridine and imidazole. Therefore, the photophysical properties of compounds having ring A bound to the platinum via a nitrogen atom may be very different than the typical metal-ligand charge transfer (MLCT) character predicted for the inventive compounds. For example, the calculated LUMO of Comparative Compound 5' is −2.24 eV, while the calculated LUMO of Compound 1' is −0.97 eV. Therefore, the coordination of ring A to the platinum via a nitrogen atom may result in a large and undesirable lowering of the triplet energy. Alternatively, the inventive compounds, in which ring A coordinates to the platinum via a carbon atom, may have a high triplet energy.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as tong as the compound is typically used as a hole injecting/transporting material. Examples of the material include, but not limit to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

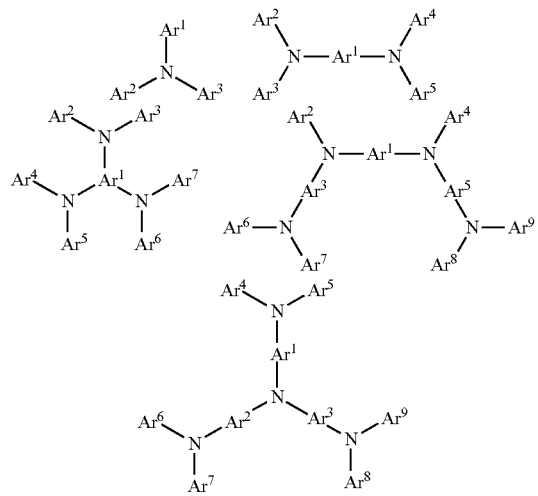

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group.

Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one embodiment, $Ar^1$ to $Ar^9$ is independently selected from the group consisting of:

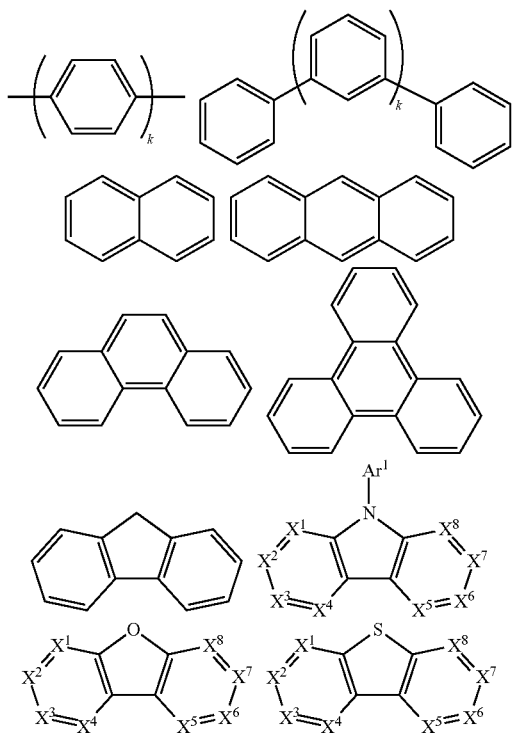

k is an integer from 1 to 20; $X^1$ to $X^8$ is C (including CH) or N; $Ar^1$ has the same group defined above.

Examples of metal complexes used in HIL or HTL include, but not limit to the following general formula:

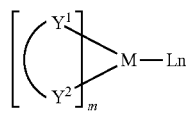

M is a metal, having an atomic weight greater than 40; $(Y^1-Y^2)$ is a bidentate ligand, $Y^1$ and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one embodiment, $(Y^1-Y^2)$ is a 2-phenylpyridine derivative.

In another embodiment, $(Y^1-Y^2)$ is a carbene ligand.

In another embodiment, M is selected from Ir, Pt, Os, and Zn.

In a further embodiment, the metal complex has a smallest oxidation potential in solution vs. Fc$^+$/Fc couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant.

Examples of metal complexes used as host are preferred to have the following general formula:

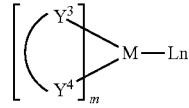

M is a metal; $(Y^3-Y^4)$ is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one embodiment, the metal complexes are:

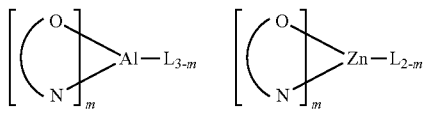

(O—N) is a bidentate having metal coordinated to atoms O and N.

In another embodiment, M is selected from Ir and Pt.

In a further embodiment, $(Y^3-Y^4)$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one embodiment, host compound contains at least one of the following groups in the molecule:

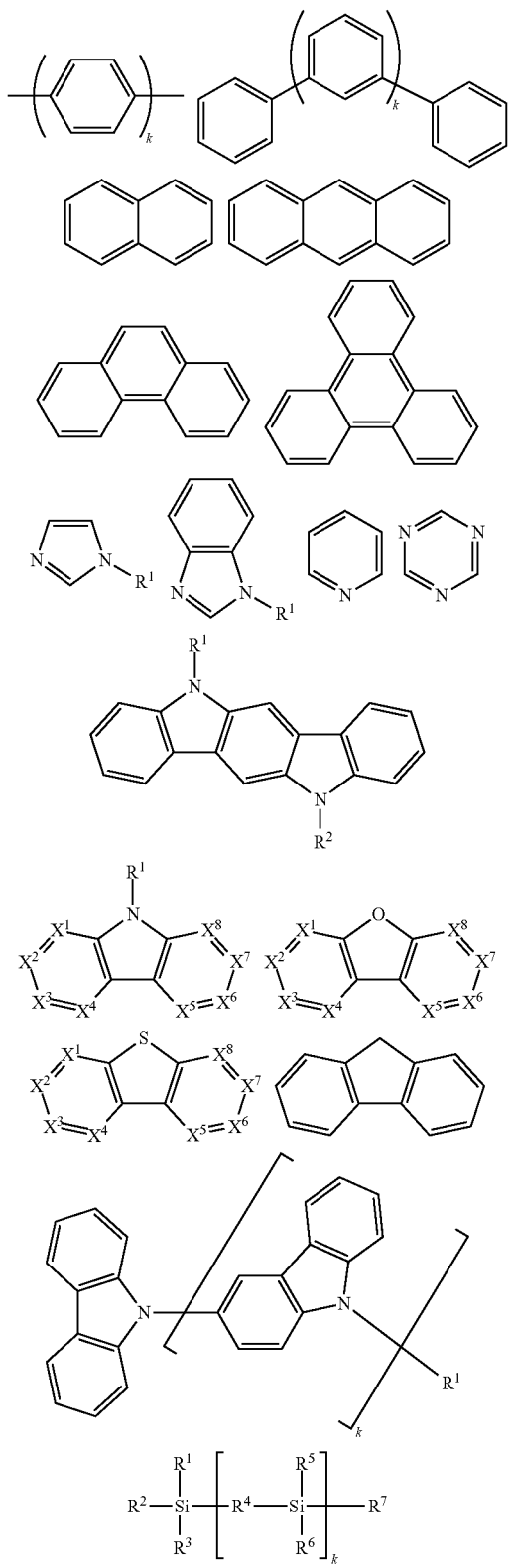

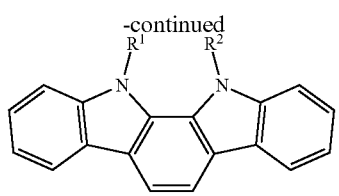

$R^1$ to $R^7$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 0 to 20.

$X^1$ to $X^8$ is selected from C (including CH) or N.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one embodiment, compound used in HBL contains the same molecule used as host described above.

In another embodiment, compound used in HBL contains at least one of the following groups in the molecule:

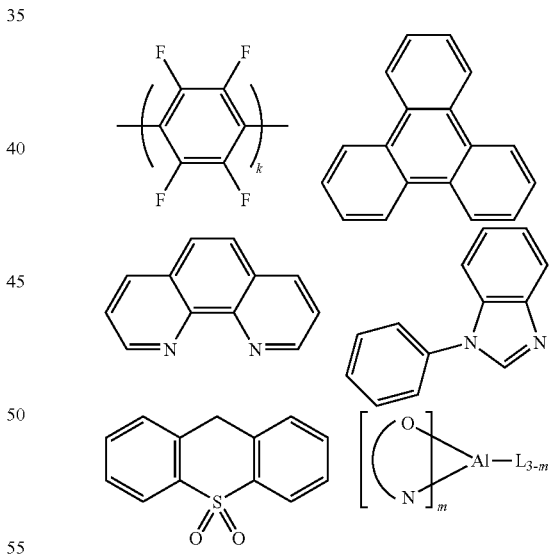

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one embodiment, compound used in ETL contains at least one of the following groups in the molecule:

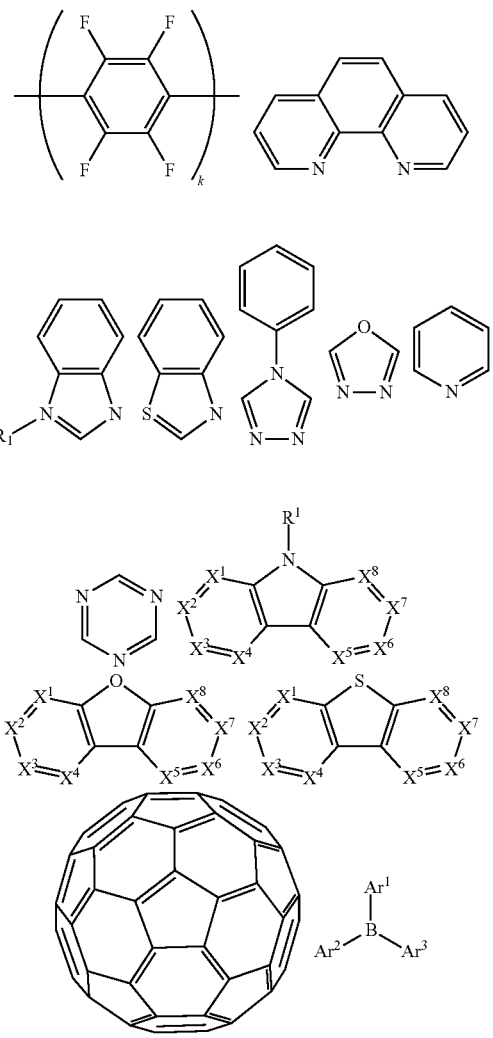

$R^1$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

$Ar^1$ to $Ar^3$ has the similar definition as Ar's mentioned above.

k is an integer from 0 to 20.

$X^1$ to $X^8$ is selected from C (including CH) or N.

In another embodiment, the metal complexes used in ETL contains, but not limit to the following general formula:

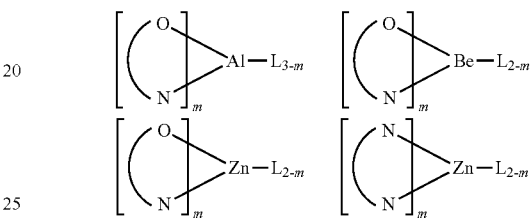

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of the OLED device, the hydrogen atoms can be partially or fully deuterated.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 6 below. Table 6 lists non-limiting classes of materials, non-limiting examples of compounds for each class, and references that disclose the materials.

TABLE 6

| MATERIAL | EXAMPLES OF MATERIAL | PUBLICATIONS |
|---|---|---|
| Hole injection materials | | |
| Phthalocyanine and porphryin compounds | | Appl. Phys. Lett. 69, 2160 (1996) |

TABLE 6-continued

| MATERIAL | EXAMPLES OF MATERIAL | PUBLICATIONS |
|---|---|---|
| Starburst triarylamines | 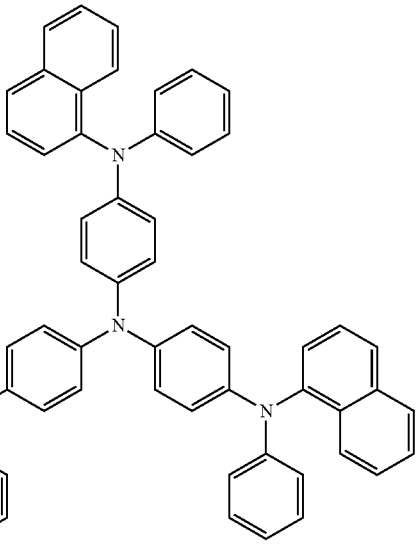 | J. Lumin. 72-74, 985 (1997) |
| $CF_x$ Fluorohydrocarbon polymer | $-\!\!\left[CH_xF_y\right]_{\!n}\!\!-$ | Appl. Phys. Lett. 78, 673 (2001) |
| Conducting polymers (e.g., PEDOT:PSS, polyaniline, polypthiophene) | 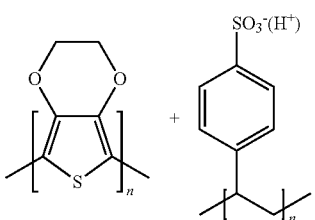 | Synth. Met. 87, 171 (1997) WO2007002683 |
| Phosphonic acid and sliane SAMs | 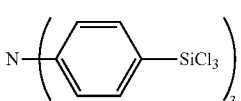 | US20030162053 |
| Triarylamine or polythiophene polymers with conductivity dopants | 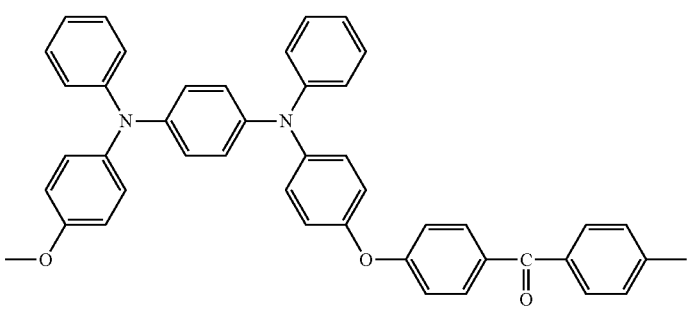 and | EP1725079A1 |

TABLE 6-continued
| MATERIAL | EXAMPLES OF MATERIAL | PUBLICATIONS |
|---|---|---|
| | 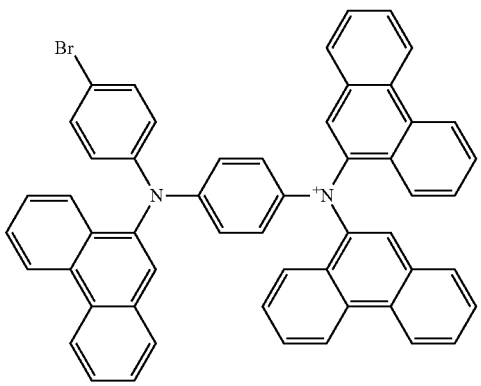 [SMILES: Brc1ccc(N(c2ccc([NH+](c3cc4ccccc4c4ccccc34)c3cc4ccccc4c4ccccc34)cc2)c2cc3ccccc3c3ccccc23)cc1] | |
| Arylamines complexed with metal oxides such as molybdenum and tungsten oxides | 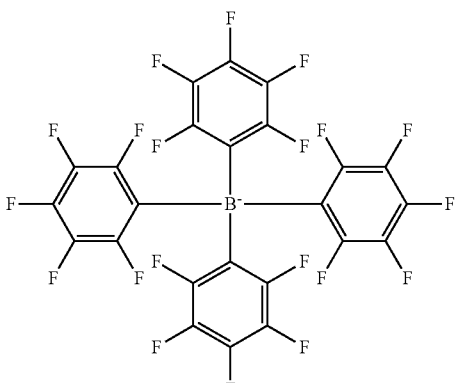 | SID Symposium Digest, 37, 923 (2006) WO2009018009 |
| p-type semiconducting organic complexes | 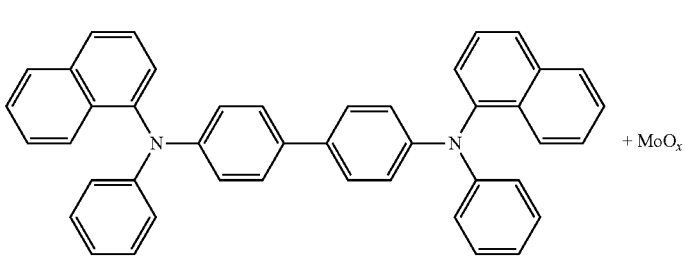 [SMILES: c1ccc(N(c2ccc(-c3ccc(N(c4ccccc4)c4cccc5ccccc45)cc3)cc2)c2cccc3ccccc23)cc1] | US20020158242 |
| Metal organometallic complexes | 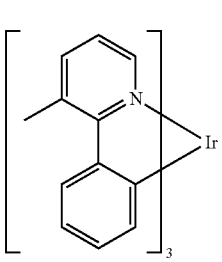 | US20060240279 |

TABLE 6-continued

| MATERIAL | EXAMPLES OF MATERIAL | PUBLICATIONS |
| --- | --- | --- |
| Cross-linkable compounds | | US20080220265 |
| Hole transporting materials | | |
| Triarylamines (e.g., TPD, α-NPD) | | Appl. Phys. Lett. 51, 913 (1987) |
| | | U.S. Pat. No. 5,061,569 |
| | | EP650955 |

TABLE 6-continued

| MATERIAL | EXAMPLES OF MATERIAL | PUBLICATIONS |
|---|---|---|
| | | J. Mater. Chem. 3, 319 (1993) |
| | | Appl. Phys. Lett. 90, 183503 (2007) |
| | | Appl. Phys. Lett. 90, 183503 (2007) |

TABLE 6-continued

| MATERIAL | EXAMPLES OF MATERIAL | PUBLICATIONS |
| --- | --- | --- |
| Triaylamine on spirofluorene core | | Synth. Met. 91, 209 (1997) |
| Arylamine carbazole compounds | | Adv. Mater. 6, 677 (1994), US20080124572 |
| Triarylamine with (di)benzothiophene/ (di)benzofuran | | US20070278938, US20080106190 |
| Indolocarbazoles | | Synth. Met. 111, 421 (2000) |

TABLE 6-continued

| MATERIAL | EXAMPLES OF MATERIAL | PUBLICATIONS |
|---|---|---|
| Isoindole compounds | | Chem. Mater. 15, 3148 (2003) |
| Metal carbene complexes | | US20080018221 |

Phosphorescent OLED host materials
Red hosts

| | | |
|---|---|---|
| Arylcarbazoles | | Appl. Phys. Lett. 78, 1622 (2001) |
| Metal 8-hydroxyquinolates (e.g., Alq$_3$, BAlq) | | Nature 395, 151 (1998) |
| | | US20060202194 |

TABLE 6-continued

| MATERIAL | EXAMPLES OF MATERIAL | PUBLICATIONS |
|---|---|---|
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |
| Zinc complexes | | WO2009062578 |

TABLE 6-continued
| MATERIAL | EXAMPLES OF MATERIAL | PUBLICATIONS |
|---|---|---|
| | Green hosts | |
| Arylcarbazoles | 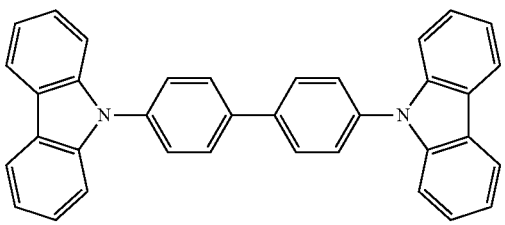 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 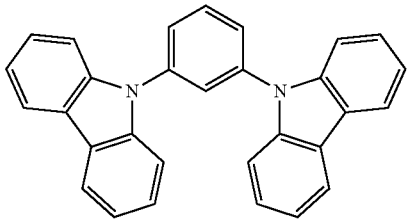 [SMILES: c1cc(-n2c3ccccc3c3ccccc32)cc(-n2c3ccccc3c3ccccc32)c1] | US20030175553 |
| | 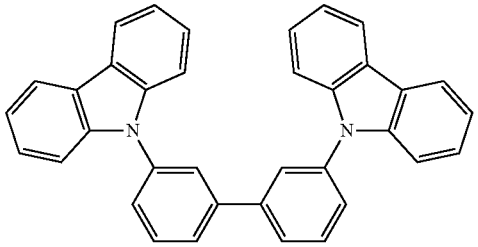 [SMILES: c1cc(-c2cccc(-n3c4ccccc4c4ccccc43)c2)cc(-n2c3ccccc3c3ccccc32)c1] | WO2001039234 |
| Aryltriphenylene compounds | 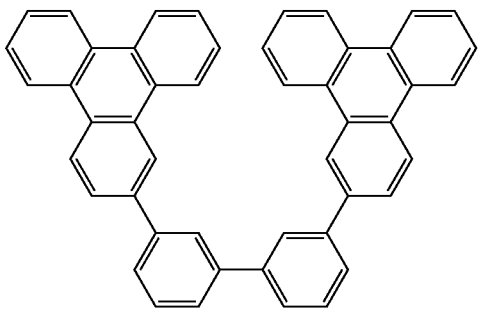 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 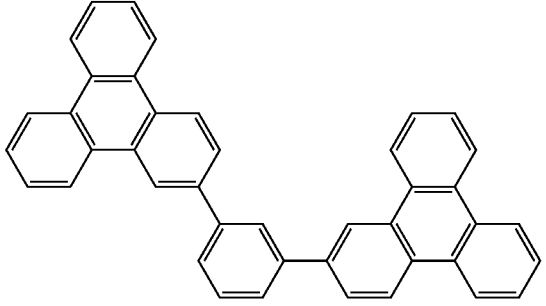 [SMILES: c1cc(-c2ccc3c4ccccc4c4ccccc4c3c2)cc(-c2ccc3c4ccccc4c4ccccc4c3c2)c1] | US20060280965 |
| | 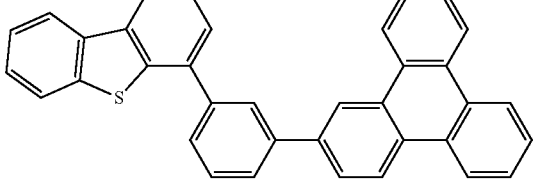 | WO2009021126 |

TABLE 6-continued
| MATERIAL | EXAMPLES OF MATERIAL | PUBLICATIONS |
|---|---|---|
| Donor acceptor type molecules | 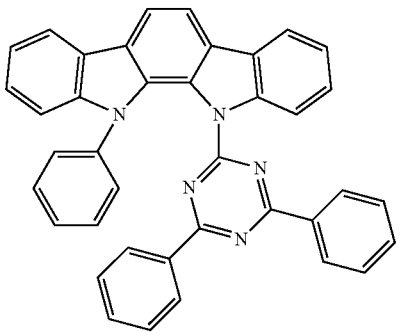 [SMILES: c1ccc(-c2nc(-c3ccccc3)nc(-n3c4ccccc4c4ccc5c6ccccc6n(-c6ccccc6)c5c43)n2)cc1] | WO2008056746 |
| Aza-carbazole/DBT/DBF | 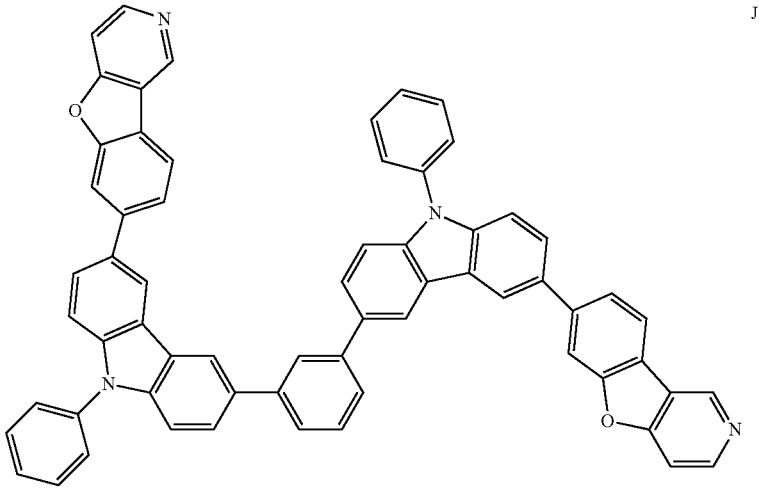 | JP2008074939 |
| Polymers (e.g., PVK) | 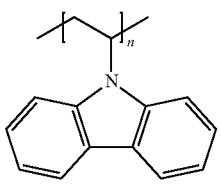 | Appl. Phys. Lett. 77, 2280 (2000) |
| Spirofluorene compounds | 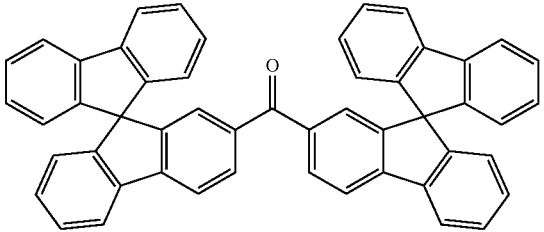 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 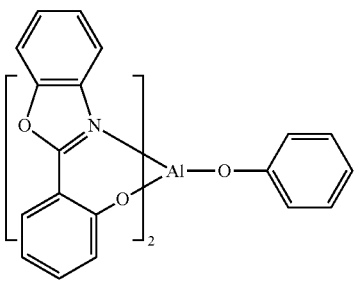 | WO2005089025 |

TABLE 6-continued

| MATERIAL | EXAMPLES OF MATERIAL | PUBLICATIONS |
|---|---|---|
| | | WO2006132173 |
| | | JP200511610 |
| Spirofluorene-carbazole compounds | | JP2007254297 |
| | | JP2007254297 |
| Indolocabazoles | | WO2007063796 |

TABLE 6-continued
| MATERIAL | EXAMPLES OF MATERIAL | PUBLICATIONS |
|---|---|---|
| | 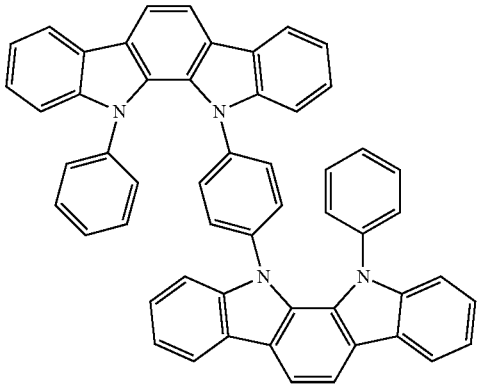 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 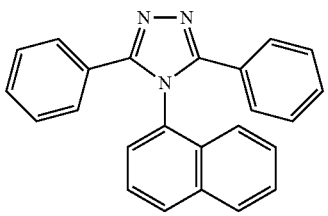 [SMILES: c1ccc(-c2nnc(-c3ccccc3)n2-c2cccc3ccccc23)cc1] | J. Appl. Phys. 90, 5048 (2001) |
| | 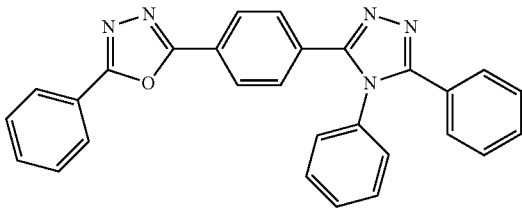 [SMILES: c1ccc(-c2nnc(-c3ccc(-c4nnc(-c5ccccc5)n4-c4ccccc4)cc3)o2)cc1] | WO2004107822 |
| Tetraphenylene complexes | 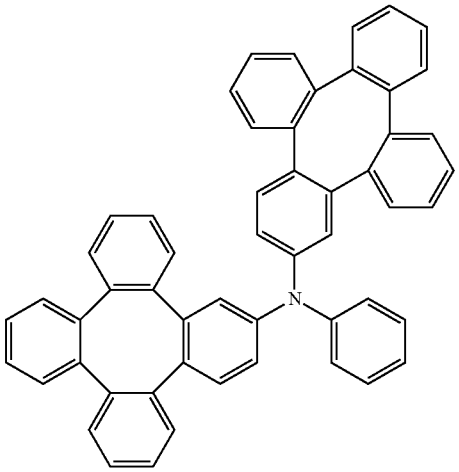 [SMILES: c1ccc(N(c2ccc3c(c2)-c2ccccc2-c2ccccc2-c2ccccc2-3)c2ccc3c(c2)-c2ccccc2-c2ccccc2-c2ccccc2-3)cc1] | US20050112407 |
| Metal phenoxypyridine compounds | 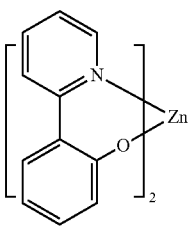 | WO2005030900 |

TABLE 6-continued

| MATERIAL | EXAMPLES OF MATERIAL | PUBLICATIONS |
|---|---|---|
| Metal coordination complexes (e.g., Zn, Al with N^N ligands) | | US20040137268, US20040137267 |

Blue hosts

| | | |
|---|---|---|
| Arylcarbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |
| | | WO2009086028 |

TABLE 6-continued
| MATERIAL | EXAMPLES OF MATERIAL | PUBLICATIONS |
|---|---|---|
|  | 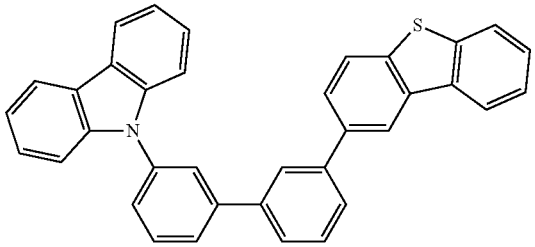 [SMILES: c1cc(-c2cccc(-n3c4ccccc4c4ccccc43)c2)cc(-c2ccc3sc4ccccc4c3c2)c1] | US20090030202, US20090017330 |
| Silicon aryl compounds | 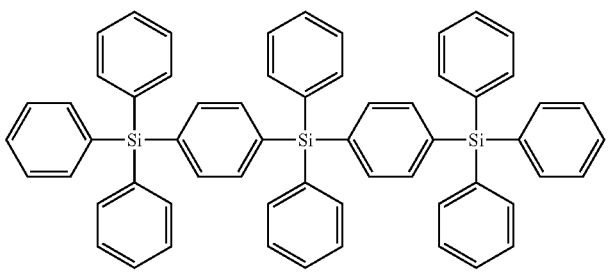 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
|  | 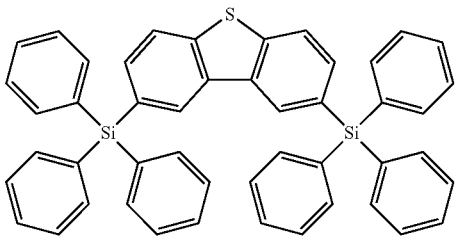 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 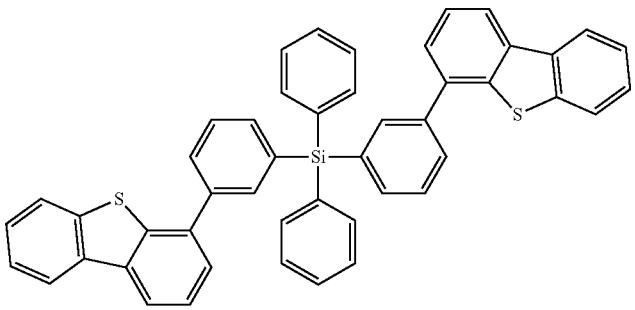 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 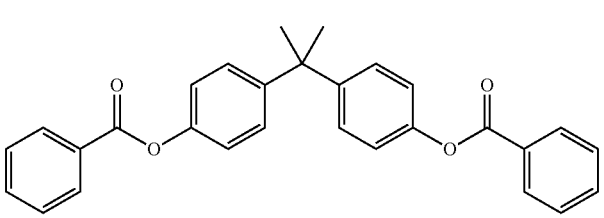 [SMILES: CC(C)(c1ccc(OC(=O)c2ccccc2)cc1)c1ccc(OC(=O)c2ccccc2)cc1] | WO2006100298 |
| High triplet metal organometallic complex | 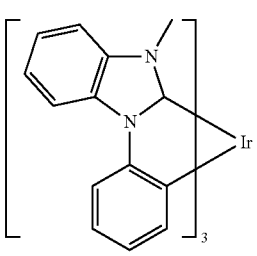 | U.S. Pat. No. 7,154,114 |

TABLE 6-continued

| MATERIAL | EXAMPLES OF MATERIAL | PUBLICATIONS |
|---|---|---|
| | Phosphorescent dopants | |
| | Red dopants | |
| Heavy metal porphyrins (e.g., PtOEP) | | Nature 395, 151 (1998) |
| Iridium(III) organometallic complexes | | Appl. Phys. Lett. 78, 1622 (2001) |
| | | US2006835469 |
| | | US2006835469 |

TABLE 6-continued
| MATERIAL | EXAMPLES OF MATERIAL | PUBLICATIONS |
|---|---|---|
| | 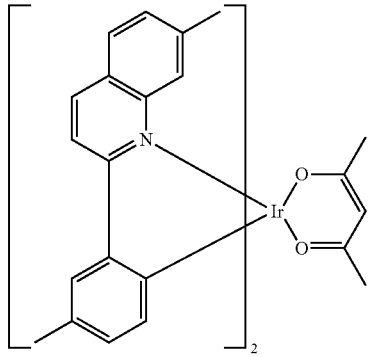 | US20060202194 |
| | 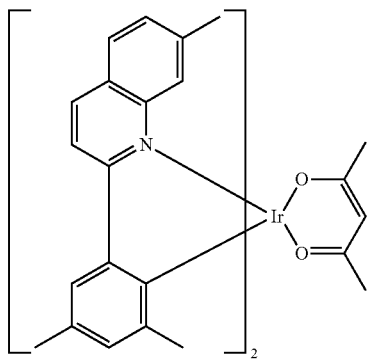 | US20060202194 |
| | 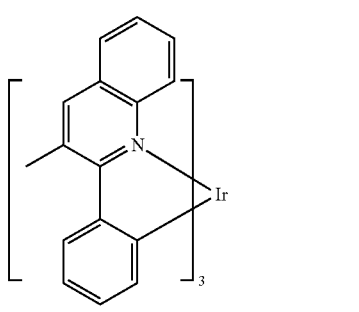 | US20070087321 |
| | 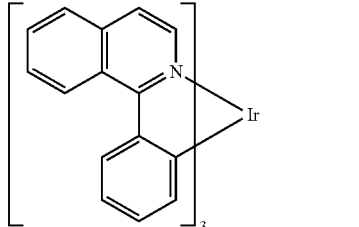 | US20070087321 |
| | 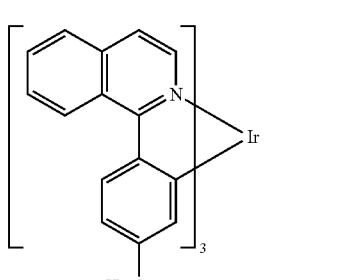 | Adv. Mater. 19, 739 (2007) |

TABLE 6-continued

| MATERIAL | EXAMPLES OF MATERIAL | PUBLICATIONS |
|---|---|---|
| | | WO2009100991 |
| | | WO2008101842 |
| Platinum(II) organometallic complexes | | WO2003040257 |
| Osminum(III) complexes | | Chem. Mater. 17, 3532 (2005) |
| Ruthenium(II) complexes | | Adv. Mater. 17, 1059 (2005) |
| Rhenium (I), (II), and (III) complexes | | US20050244673 |

TABLE 6-continued
| MATERIAL | EXAMPLES OF MATERIAL | PUBLICATIONS |
|---|---|---|
| | Green dopants | |
| Iridium(III) organometallic complexes | 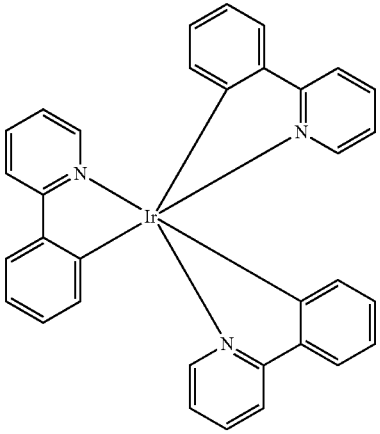 and its derivatives | Inorg. Chem. 40, 1704 (2001) |
| | 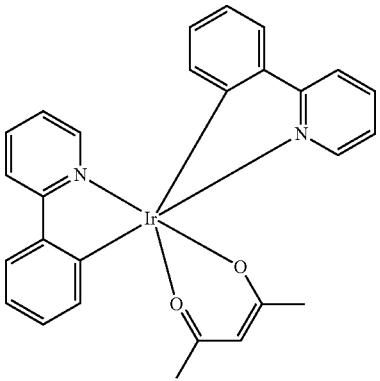 | US20020034656 |
| | 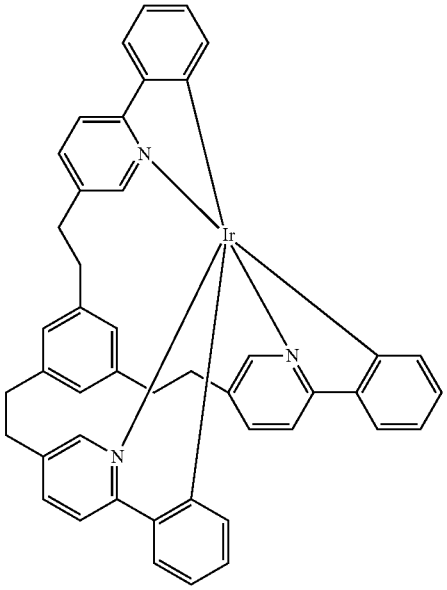 | U.S. Pat. No. 7,332,232 |

TABLE 6-continued

| MATERIAL | EXAMPLES OF MATERIAL | PUBLICATIONS |
| --- | --- | --- |
| | | US20090108737 |
| | | US20090039776 |
| | | U.S. Pat. No. 6,921,915 |
| | | U.S. Pat. No. 6,687,266 |
| | | Chem. Mater. 16, 2480 (2004) |

TABLE 6-continued
| MATERIAL | EXAMPLES OF MATERIAL | PUBLICATIONS |
|---|---|---|
| | 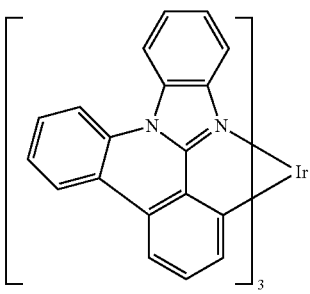 | US20070190359 |
| | 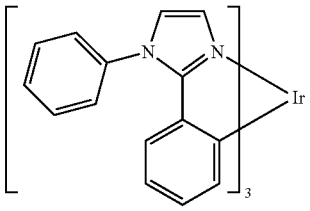 | US 20060008670<br>JP2007123392 |
| | 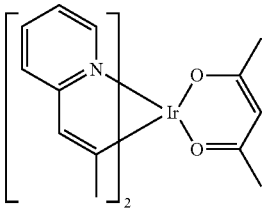 | Adv. Mater. 16, 2003 (2004) |
| | 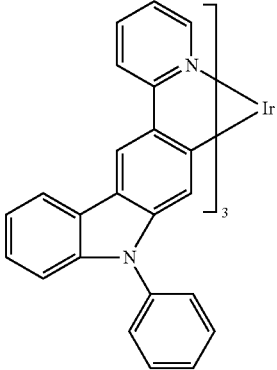 | Angew. Chem. Int. Ed. 2006, 45, 7800 |
| | 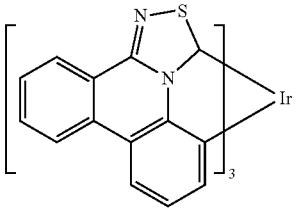 | WO2009050290 |
| | 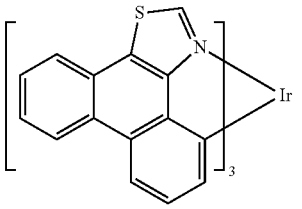 | US20090165846 |

TABLE 6-continued

| MATERIAL | EXAMPLES OF MATERIAL | PUBLICATIONS |
|---|---|---|
| | | US20080015355 |
| Monomer for polymeric metal organometallic compounds | | U.S. Pat. No. 7,250,226, U.S. Pat. No. 7,396,598 |
| Pt(II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |

TABLE 6-continued
| MATERIAL | EXAMPLES OF MATERIAL | PUBLICATIONS |
|---|---|---|
| | 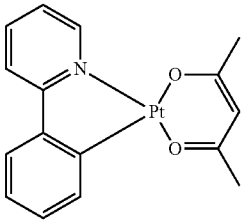 | WO2002015645 |
| | 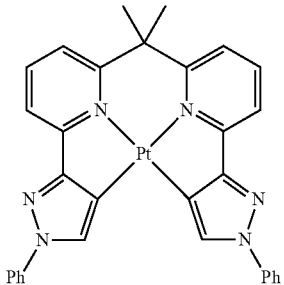 | US20060263635 |
| Cu complexes | 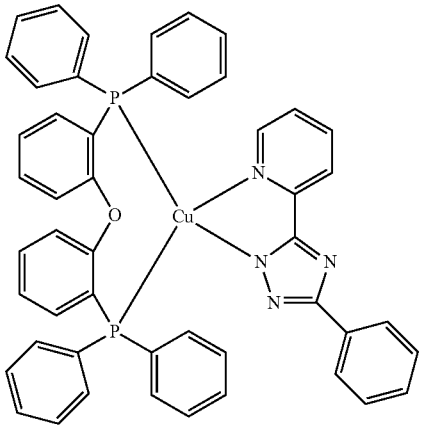 | WO2009000673 |
| Gold complexes | 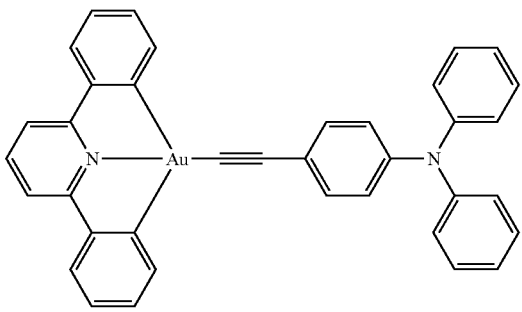 | Chem. Commun. 2906 (2005) |
| Rhenium(III) complexes | 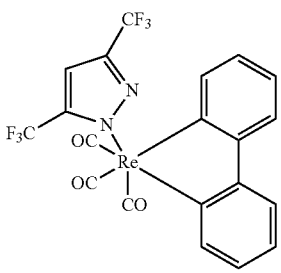 | Inorg. Chem. 42, 1248 (2003) |

TABLE 6-continued

| MATERIAL | EXAMPLES OF MATERIAL | PUBLICATIONS |
| --- | --- | --- |
| Deuterated organometallic complexes | | US20030138657 |
| Organometallic complexes with two or more metal centers | | US20030152802 |
| | | U.S. Pat. No. 7,090,928 |

Blue dopants

| | | |
| --- | --- | --- |
| Iridium(III) organometallic complexes | | WO2002002714 |

TABLE 6-continued

| MATERIAL | EXAMPLES OF MATERIAL | PUBLICATIONS |
|---|---|---|
| | | WO2006009024 |
| | | US20060251923 |
| | | U.S. Pat. No. 7,393,599, WO2006056418, US20050260441, WO2005019373 |
| | | U.S. Pat. No. 7,534,505 |
| | | U.S. Pat. No. 7,445,855 |
| | | US20070190359, US20080297033 |

TABLE 6-continued

| MATERIAL | EXAMPLES OF MATERIAL | PUBLICATIONS |
|---|---|---|
| | | U.S. Pat. No. 7,338,722 |
| | | US20020134984 |
| | | Angew. Chem. Int. Ed. 47, 1 (2008) |
| | | Chem. Mater. 18, 5119 (2006) |
| | | Inorg. Chem. 46, 4308 (2007) |

TABLE 6-continued
| MATERIAL | EXAMPLES OF MATERIAL | PUBLICATIONS |
|---|---|---|
| | 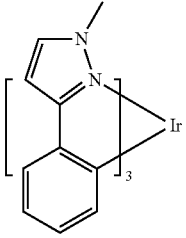 | WO2005123873 |
| | 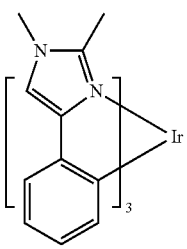 | WO2005123873 |
| | 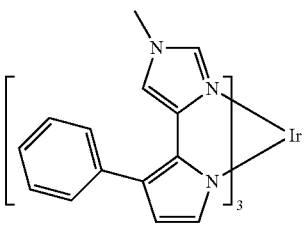 | WO2007004380 |
| | 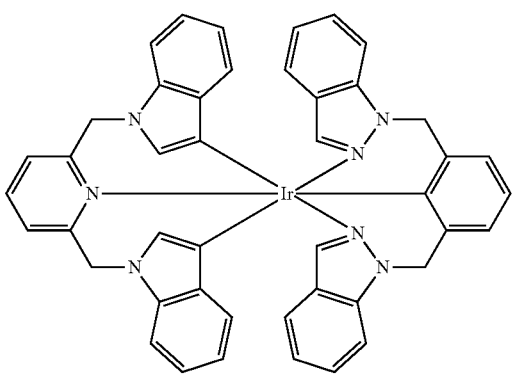 | WO2006082742 |
| Osmium(II) complexes | 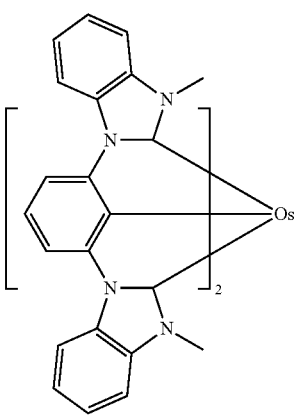 | U.S. Pat. No. 7,279,704 |

TABLE 6-continued

| MATERIAL | EXAMPLES OF MATERIAL | PUBLICATIONS |
|---|---|---|
| | [pyrazolyl-pyridyl Os(PPh₃) complex] | Organometallics 23, 3745 (2004) |
| Gold complexes | Ph₂P-CH₂-PPh₂ bridged Au-Cl / Au-Cl dimer | Appl. Phys. Lett. 74, 1361 (1999) |
| Platinum(II) complexes | [Pt complex with thiophene-pyrimidine and tris(pyrazolyl)borate ligands] | WO2006098120, WO2006103874 |

Exciton/hole blocking layer materials

| MATERIAL | EXAMPLES OF MATERIAL | PUBLICATIONS |
|---|---|---|
| Bathocuprine compounds (e.g., BCP, BPhen) | [BCP structure] | Appl. Phys. Lett. 75, 4 (1999) |
| | [BPhen structure] | Appl. Phys. Lett. 79, 449 (2001) |
| Metal 8-hydroxyquinolates (e.g., BAlq) | [BAlq structure] | Appl. Phys. Lett. 81, 162 (2002) |

TABLE 6-continued

| MATERIAL | EXAMPLES OF MATERIAL | PUBLICATIONS |
| --- | --- | --- |
| 5-member ring electron deficient heterocycles such as triazole, oxadiazole, imidazole, benzoimidazole | | Appl. Phys. Lett. 81, 162 (2002) |
| Triphenylene compounds | | US20050025993 |
| Fluorinated aromatic compounds | | Appl. Phys. Lett. 79, 156 (2001) |

TABLE 6-continued

| MATERIAL | EXAMPLES OF MATERIAL | PUBLICATIONS |
|---|---|---|
| Phenothiazine-S-oxide | | WO2008132085 |

Electron transporting materials

| | | |
|---|---|---|
| Anthracene-benzoimidazole compounds | | WO2003060956 |
| | | US20090179554 |
| Aza triphenylene derivatives | | US20090115316 |

TABLE 6-continued

| MATERIAL | EXAMPLES OF MATERIAL | PUBLICATIONS |
| --- | --- | --- |
| Anthracene-benzothiazole compounds | | Appl. Phys. Lett. 89, 063504 (2006) |
| Metal 8-hydroxyquinolates (e.g., $Alq_3$, $Zrq_4$) | | Appl. Phys. Lett. 51, 913 (1987) U.S. Pat. No. 7,230,107 |
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |

TABLE 6-continued
| MATERIAL | EXAMPLES OF MATERIAL | PUBLICATIONS |
|---|---|---|
|  | 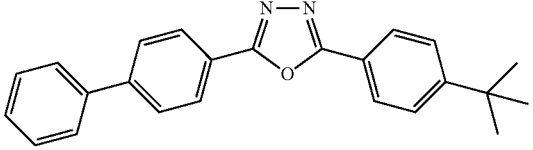 [SMILES: CC(C)(C)c1ccc(-c2nnc(-c3ccc(-c4ccccc4)cc3)o2)cc1] | Appl. Phys. Lett. 55, 1489 (1989) |
|  | 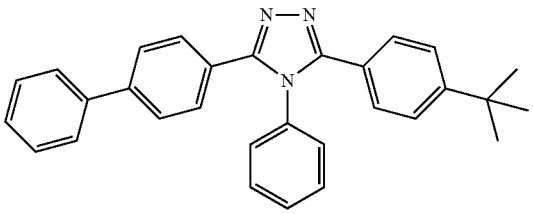 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 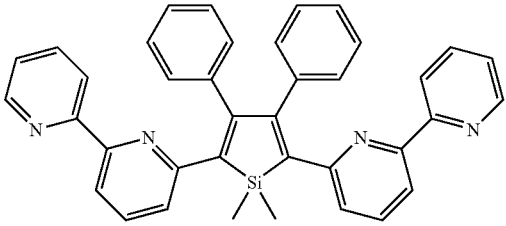 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 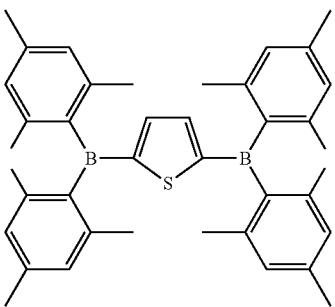 [SMILES: Cc1cc(C)c(B(c2ccc(B(c3c(C)cc(C)cc3C)c3c(C)cc(C)cc3C)s2)c2c(C)cc(C)cc2C)c(C)c1] | J. Am. Chem. Soc. 120, 9714 (1998) |
| Fluorinated aromatic compounds | 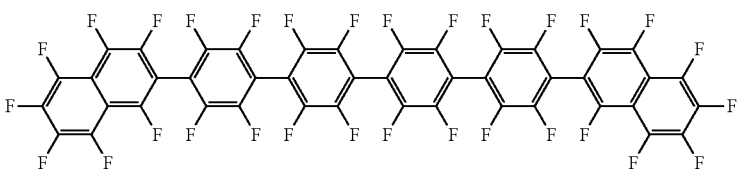 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |
| Fullerene (e.g., C60) | 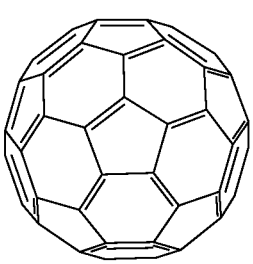 | US20090101870 |

TABLE 6-continued

| MATERIAL | EXAMPLES OF MATERIAL | PUBLICATIONS |
| --- | --- | --- |
| Triazine complexes | | US20040036077 |
| Zn (N^N) complexes | | U.S. Pat. No. 6,528,187 |

EXPERIMENTAL

Chemical abbreviations used throughout this document are as follows: Cy is cyclohexyl, dba is dibenzylideneacetone, EtOAc is ethyl acetate, DME is dimethoxyethane, dppf is 1,1'-bis(diphenylphosphino)ferrocene, S-Phos is dicyclohexyl(2',6'-dimethoxy-[1,1'-biphenyl]-2-yl)phosphine,

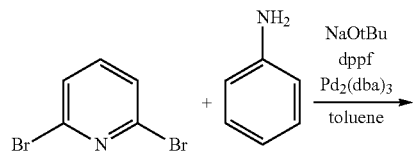

Synthesis of 6-bromo-N-(6-bromopyridin-2-yl)-N-phenylpyridin-2-amine

To a 500 mL 3-neck round-bottom flask was added 2,6-dibromopyridine (20 g, 84 mmol), aniline (3.1 mL, 33.8 mmol), dppf (0.749 g, 1.351 mmol), sodium t-butoxide (8.11 g, 84 mmol), and 250 mL toluene. Nitrogen was bubbled directly into the reaction mixture. $Pd_2(dba)_3$ (0.62 g, 0.68 mmol) was added to the reaction mixture which was heated to reflux overnight. The reaction mixture was cooled and diluted with ethyl acetate and water and tittered through Celite® to remove insoluble material. The layers were separated and the aqueous layer extracted with ethyl acetate. The organic layers were washed with brine, dried over magnesium sulfate, filtered, and evaporated. The residue was purified by column chromatography eluting with dichloromethane to give 6-bromo-N-(6-bromopyridin-2-yl)-N-phenylpyridin-2-amine (6.3 g, 46%).

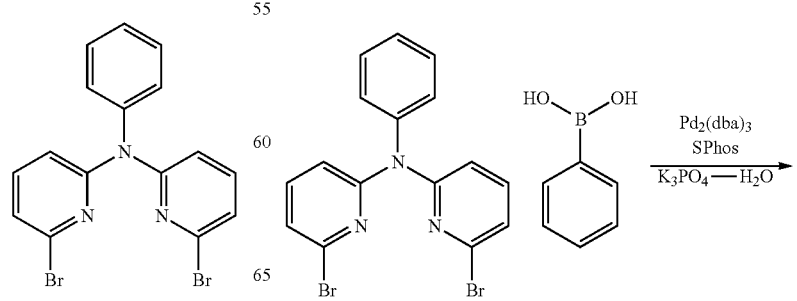

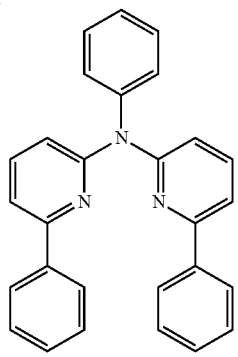

6-Bromo-N-(6-bromopyridin-2-yl)-N-phenylpyridin-2-amine (7 g, 17.3 mmol), phenylboronic acid (5.3 g, 43.2 mmol), Pd$_2$(dba)$_3$ (0.32 g, 0.35 mmol), dicyclohexyl(2',6'-dimethoxy-[1,1'-biphenyl]-2-yl)phosphine (0.57 g, 1.38 mmol), potassium phosphate tribasic monohydrate (11.94 g, 51.8 mmol), toluene (200 mL) and water (20 mL) were added to a flask and degassed with nitrogen. The reaction mixture was heated to reflux for 16 h before being cooled to room n temperature. Water was added and the layers separated, washing the aqueous twice with EtOAc and combined organics with water and brine. After removal of the solvent, the crude product was chromatographed on silica gel with 9/1 (v/v) hexane/EtOAc to give 5.6 g of a white solid, which was recrystallized from hexane to give 5.1 g of pure (HPLC purity: 100%) product as confirmed by NMR and GC/MS.

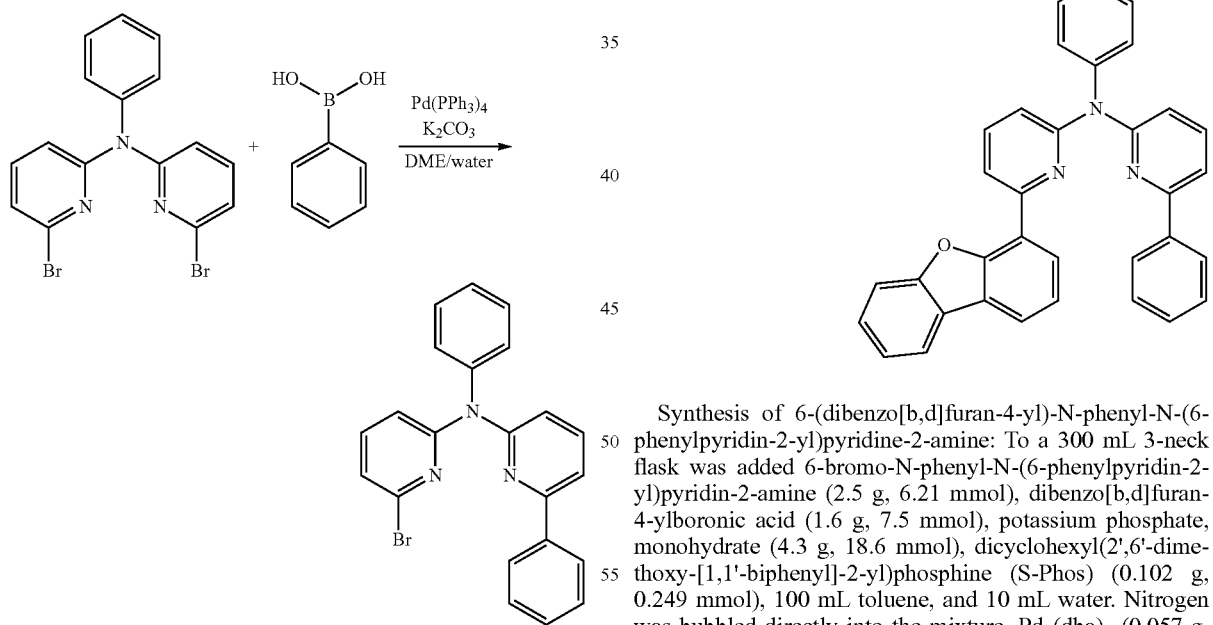

Synthesis of 6-bromo-N-phenyl-N-(6-phenylpyridin-2-yl)pyridine-2-amine

To a 1 L 3-neck round-bottom flask was added 6-bromo-N-(6-bromopyridin-2-yl)-N-phenylpyridin-2-amine (5.3 g, 13.08 mmol), phenylboronic acid (1.595 g, 13.08 mmol), potassium carbonate (5.42 g, 39.3 mmol), 200 mL dimethoxyethane and 100 mL water. Nitrogen was bubbled directly into the mixture. Pd(PPh$_3$)$_4$ (0.151 g, 0.131 mmol) was added and the reaction mixture was heated to 105° C. overnight under nitrogen. The reaction mixture was diluted with ethyl acetate and water. The layers were separated and the aqueous layer extracted with ethyl acetate. The organic layers were dried over magnesium sulfate, filtered, and evaporated leaving a yellow oil. The material was purified by column chromatography using a reverse phase column eluting with 80/20 (v/v) acetonitrile/water to give 6-bromo-N-phenyl-N-(6-phenylpyridin-2-yl)pyridine-2-amine (2.84 g, 45%).

Synthesis of 6-(dibenzo[b,d]furan-4-yl)-N-phenyl-N-(6-phenylpyridin-2-yl)pyridine-2-amine: To a 300 mL 3-neck flask was added 6-bromo-N-phenyl-N-(6-phenylpyridin-2-yl)pyridin-2-amine (2.5 g, 6.21 mmol), dibenzo[b,d]furan-4-ylboronic acid (1.6 g, 7.5 mmol), potassium phosphate, monohydrate (4.3 g, 18.6 mmol), dicyclohexyl(2',6'-dimethoxy-[1,1'-biphenyl]-2-yl)phosphine (S-Phos) (0.102 g, 0.249 mmol), 100 mL toluene, and 10 mL water. Nitrogen was bubbled directly into the mixture. Pd$_2$(dba)$_3$ (0.057 g, 0.062 mmol) was added and the reaction mixture heated to reflux overnight under nitrogen. Water was added to the reaction mixture and the layers were separated. The aqueous layer was extracted with ethyl acetate. The organic layers were washed with brine, dried over magnesium sulfate, filtered, evaporated. The material was purified by column chromatography eluting with 8/2/2.5 hexane/dichloromethane/ethyl acetate to give 6-(dibenzo[b,d]furan-4-yl)-N-phenyl-N-(6-phenylpyridin-2-yl)pyridine-2-amine (2.7 g, 88%).

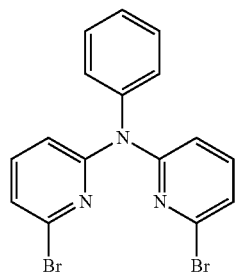

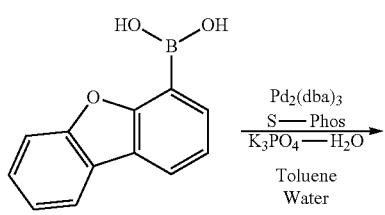

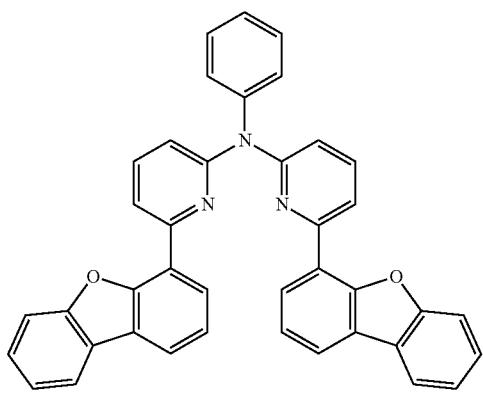

Synthesis of 6-(dibenzo[b,d]furan-4-yl)-N-(6-(dibenzo[b,d]furan-4-yl)pyridin-2-yl)-N-phenylpyridin-2-amine To a 500 mL 3-neck round-bottom flask was added 6-bromo-N-(6-bromopyridin-2-yl)-N-phenylpyridin-2-amine (4.4 g, 10.9 mmol), dibenzo[b,d]furan-4-ylboronic acid (5.1 g, 23.9 mmol), Pd$_2$(dba)$_3$ (0.10 g, 0.11 mmol), dicyclohexyl(2',6'-dimethoxy-[1,1'-biphenyl]-2-yl)phosphine (0.18 g, 0.43 mmol), and potassium phosphate tribasic monohydrate (12.5 g, 54.3 mmol) in toluene (100 mL) and water (10 mL). Nitrogen was bubbled directly into the reaction mixture for 20 min. and the reaction heated to reflux for 16 h. The reaction mixture was cooled and diluted with ethyl acetate and water and filtered through Celite to remove insoluble material. The layers were separated and the aqueous layer extracted with dichloromethane. The organic layers were washed with brine, dried over magnesium sulfate, filtered, and evaporated. The residue was purified by column chromatography eluting with 95/5 dichloromethane/ethyl acetate to give 2.1 g (87%) of 6-(dibenzo[b,d]furan-4-yl)-N-(6-(dibenzo[b,d]furan-4-yl)pyridin-2-yl)-N-phenylpyridin-2-amine as a white solid. The product was confirmed by LC/MS, NMR and HPLC (purity: 99.96%).

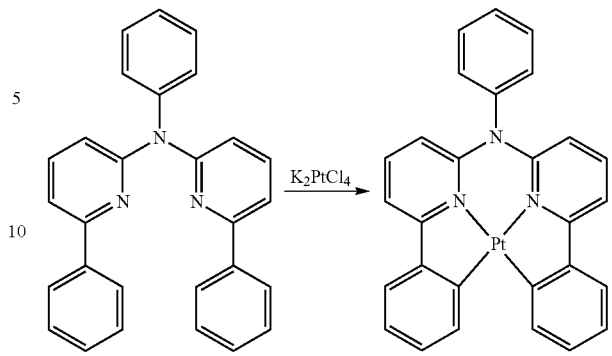

Synthesis of Compound X

N,6-Diphenyl-N-(6-phenylpyridin-2-yl)pyridin-2-amine (1.9 g, 4.8 mmol) and potassium tetrachloroplatinate (1.97 g, 4.8 mmol) were mixed in 100 mL of acetic acid. The mixture was degassed with nitrogen sparge for 20 min. and heated to 140° C. for 4 days. After cooling, water was added and the solid was collected by filtration. The solid was washed of the fit with dichloromethane to give a yellow filtrate that was dried over sodium sulfate and the solvent removed. The crude product was purified by column on silica using dichloromethane as solvent to give 1.1 g of the platinum complex. The complex was sublimed (260° C. 10$^{-5}$ Torr) to give 0.8 g of Compound X as a yellow solid (HPLC purity: 99.3%) as confirmed by NMR and LC/MS.

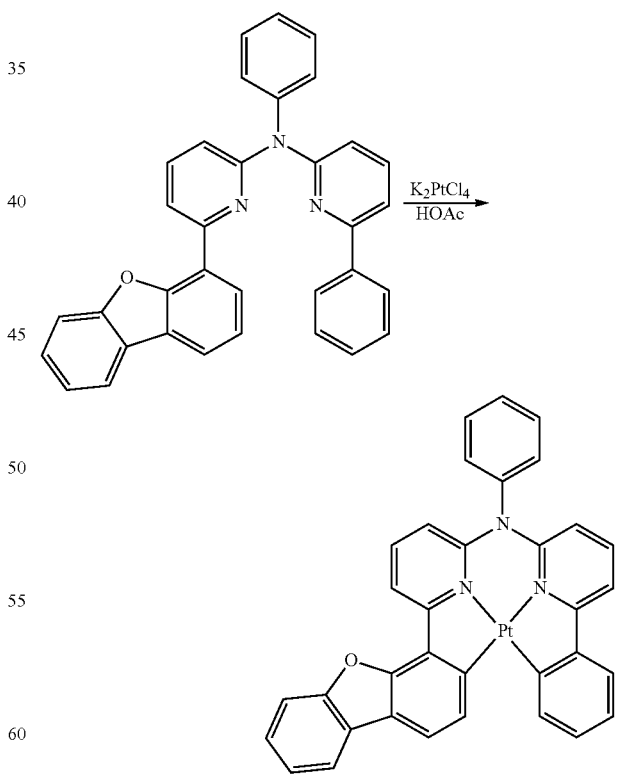

Synthesis of Compound 4

To a 300 mL 3-neck round bottom flask was added K$_2$PtCl$_4$ (2.1 g, 5.0 mmol), 6-(dibenzo[b,d]furan-4-yl)-N- phenyl-N-(6-phenylpyridin-2-yl)pyridin-2-amine (2.7 g, 5.5 mmol), and 100 mL acetic acid. The reaction mixture was purged with nitrogen for 20 minutes. The reaction mixture was heated to 140° C. under nitrogen for 3 days, cooled, and diluted with hexane. A green solid was filtered of and washed with hexane. The material was purified by column chromatography eluting with 60/40 to 70/40 (v/v) dichloromethane/hexane followed by sublimation overnight at 300° C. to yield 0.58 g (17%) of Compound as a yellow solid. The product was confirmed by LC/MS and HPLC (99.1% pure).

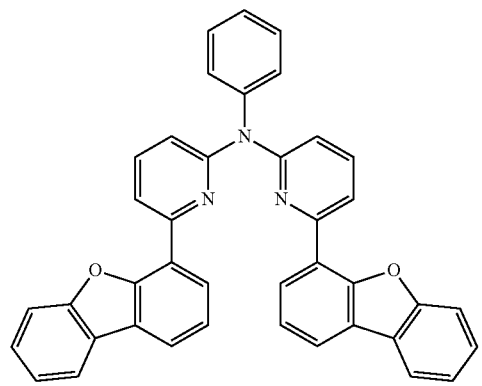

Synthesis of Compound 13

6-(Dibenzo[b,d]furan-4-yl)-N-(6-(dibenzo[b]furan-4-yl)pyridin-2-yl)-N-phenylpyridin-2-amine (1.8 g, 3.1 mmol) and K$_2$PtCl$_4$ (1.3 g, 3.1 mmol) were mixed in 100 mL of acetic acid. The mixture was bubbled with nitrogen for 20 min. before being heated to 140° C. for 4 days. After cooling, water was added and the solid collected by filtration. The solid was washed with dichloromethane to give a yellow filtrate that was concentrated to give a yellow solid. The solid was suspended in dichloromethane and methanol was added to give a precipitate that was filtered and washed with methanol and hexane and dried to give 0.88 g (37%) of Compound 13 as an orange solid. The product was confirmed by LC/MS and HPLC (99.1% pure).

Example 1. Synthesis of Compound 1'

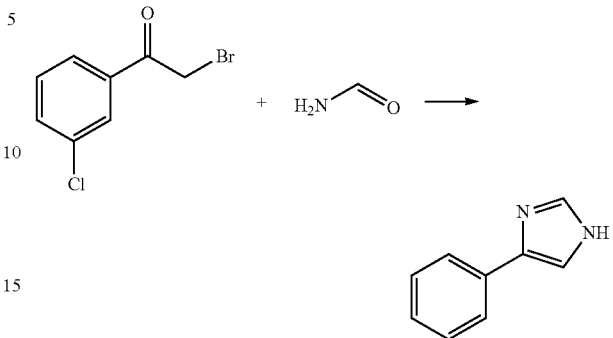

Synthesis of 4-(3-chlorophenyl)-1H-imidazole 2-bromo-1-(3-chlorophenyl)ethanone (20.15 g, 86 mmol) in 80 mL formamide was placed into a 250 mL round-bottomed flask, and the reaction mixture was heated to 165° C. for 2.5 h. The reaction was then cooled and the solid was filtered and washed with water. The filtrate was basified to pH 12, and extracted with ethyl acetate. The organic layer was combined with the crude solid, and chromatographed on silica gel with 3-5% MeOH in DCM to obtain 10.9 g (71%) of 4-(3-chlorophenyl)-1H-imidazole as a solid.

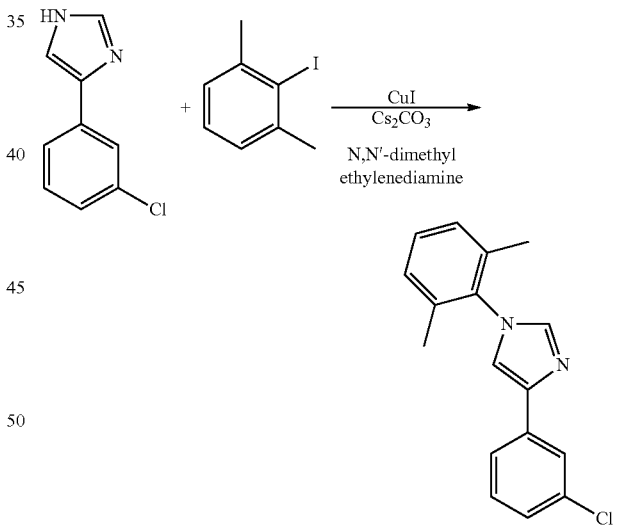

Synthesis of 4-(3-chlorophenyl)-1-(2,6-dimethylphenyl)-1H-imidazole

A pressure flask was charged with 4-(3-chlorophenyl)-1H-imidazole (10.82 g, 60.6 mmol) and 2-iodo-1,3-dimethylbenzene (16.87 g, 72.7 mmol). The reaction mixture was diluted with DMF (60 mL), and copper(I) iodide (1.1 g, 6.1 mmol), N,N-dimethylethane-1,2-diamine (2.6 nit, 24.2 mmol) and cesium carbonate (23.68 g, 72.7 mmol) were added. After degassing with nitrogen, the reaction mixture was stirred in an oil bath at 160° C. for 48 h before being diluted with ethyl acetate and filtered through celite. The filtrate was washed with aqueous LiCl, brine and water. The product was purified by chromatography on silica gel with 0-5% EtOAc in DCM to afford 3.8 g (22%) of 4-(3-chlorophenyl)-1-(2,6-dimethylphenyl)-1H-imidazole.

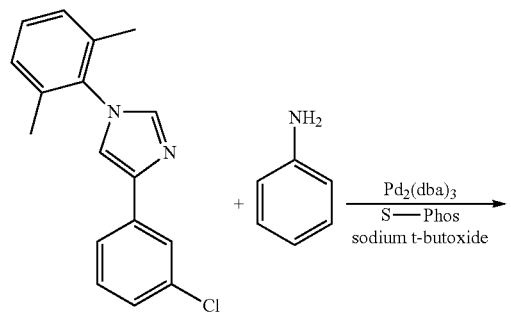

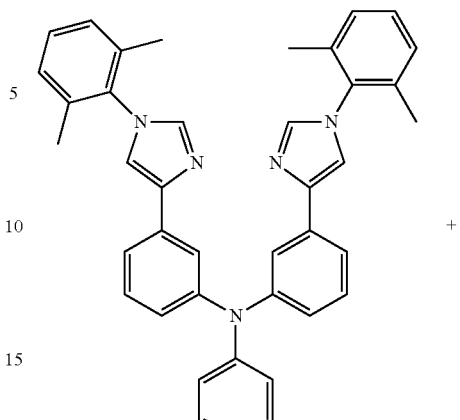

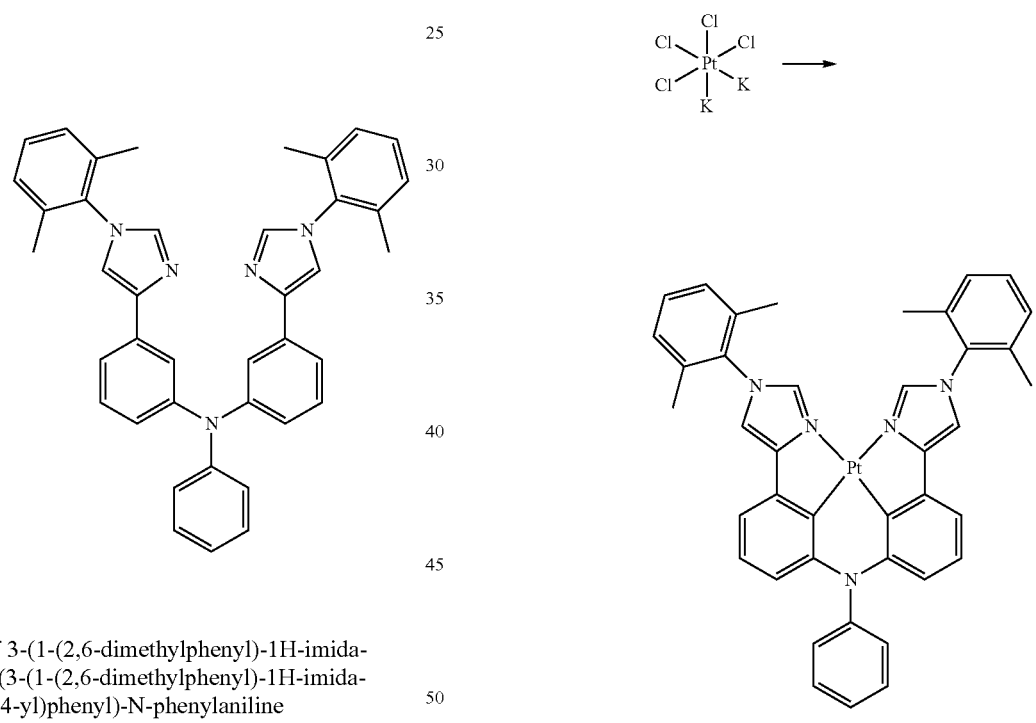

Synthesis of 3-(1-(2,6-dimethylphenyl)-1H-imidazol-4-yl)-N-(3-(1-(2,6-dimethylphenyl)-1H-imidazol-4-yl)phenyl)-N-phenylaniline 4-(3-chlorophenyl)-1-(2,6-dimethylphenyl)-1H-imidazole (5.4 g, 19.1 mmol) and aniline (0.87 mL, 9.5 mmol) in toluene (200 mL) were placed in a 500 mL round-bottomed flask. Sodium tert-butoxide (4.0 g, 41.9 mmol) and dicyclohexyl(2',6'-dimethoxy-[1,1'-biphenyl]-2-yl)phosphine (0.783 g, 1.906 mmol) were added, and the reaction mixture was degassed before Pd$_2$(dba)$_3$ (0.44 g, 0.48 mmol) was added. This was evacuated and backfilled with nitrogen. The reaction was stirred at reflux for 24 h. The mixture was then filtered through celite. Next, the filtrate was concentrated and chromatographed on silica gel with 10-25% ethyl acetate in hexane followed by 10% ethyl acetate in DCM to obtain 2.8 g (51%) of 3-(1-(2,6-dimethylphenyl)-1H-imidazol-4-yl)-N-(3-(1-(2,6-dimethylphenyl)-1H-imidazol-4-yl)phenyl)-N-phenylaniline as a white solid.

Synthesis of the Compound 1'

3-(1-(2,6-dimethylphenyl)-1H-imidazol-4-yl)-N-(3-(1-(2,6-dimethylphenyl)-1H-imidazol-4-yl)phenyl)-N-phenylaniline (1.7 g, 2.9 mmol) and potassium tetrachloroplatinate (1.2 g, 2.9 mmol) in acetic acid (100 mL) were added into a 250 mL flask, which gave a red suspension. The suspension was purged with nitrogen. The reaction mixture was stirred at reflux for 48 h, at which point it was cooled to room temperature and 100 mL of water were added. The product was filtered and purified by column chromatography on silica with 2:1 dichloromethane:hexane to obtain 0.72 g (33%) of Compound 1' as a yellow solid.

Example 2. Synthesis of Compound 2'

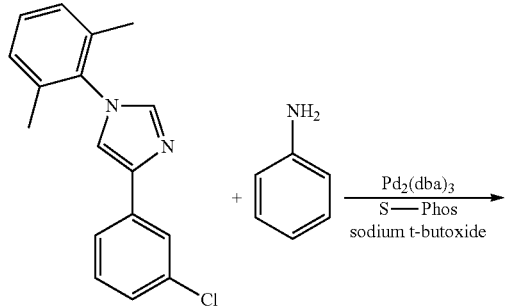

Synthesis of 3-(1-(2,6-dimethylphenyl)-1H-imidazol-4-yl)-N-phenylaniline

A 500 mL round-bottomed flask was charged with 4-(3-chlorophenyl)-1-(2,6-dimethylphenyl)-1H-imidazole (5.39 g, 19.06 tumor) and aniline (0.870 mL, 9.53 mmol) in toluene (200 mL). Sodium tert-butoxide (4.03 g, 41.9 mmol) and dicyclohexyl(2',6'-dimethoxy-[1,1'-biphenyl]-2-yl)phosphine (0.783 g, 1.90 mmol) were added, and the reaction mixture was degassed with nitrogen before Pd$_2$(dba)$_3$ (0.436 g, 0.477 mmol) was added. The reaction flask was evacuated and backfilled with nitrogen, and then stirred at reflux for 24 h. The crude mixture was filtered through celite, and the filtrate was concentrated in vacuo and purified using column chromatography with 10% ethyl acetate in dichloromethane to afford 1.4 g (42%) of 3-(1-(2,6-dimethylphenyl)-1H-imidazol-4-yl)-N-phenylaniline as a solid.

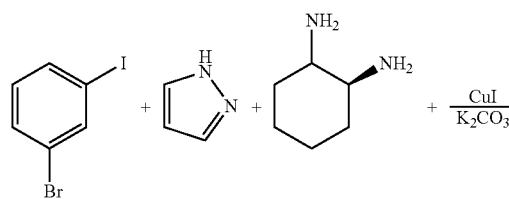

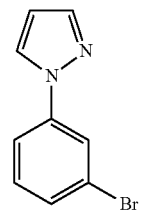

Synthesis of 1-(3-bromophenyl)-1H-pyrazole 1-bromo-3-iodobenzene (18.20 g, 64.3 mmol), 1H-pyrazole (4.38 g, 64.3 mmol), and (1S,2S)-cyclohexane-1,2-diamine (1.5 g, 12.9 mmol) in dioxane (400 mL) were placed into a 1 L round-bottomed flask. Copper(I) iodide 2.0 (0.613 g, 3.22 mmol) and potassium carbonate (17.78 g, 129 mmol) were added, and the reaction mixture was stirred at reflux for 19 h. The crude mixture was then filtered through a pad of celite. The filtrate was diluted with 400 mL of dichloromethane, and was washed with water. The organic layer was concentrated and chromatographed on silica gel with 5% ethyl acetate in hexane to give 7.3 g (51%) of 1-(3-bromophenyl)-1H-pyrazole as a white solid.

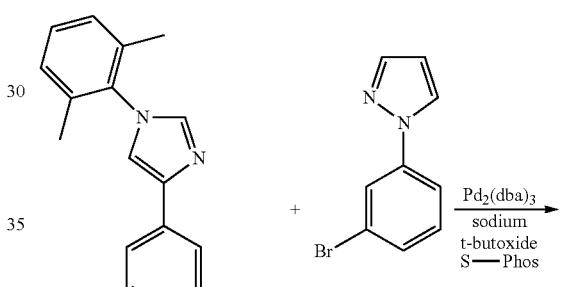

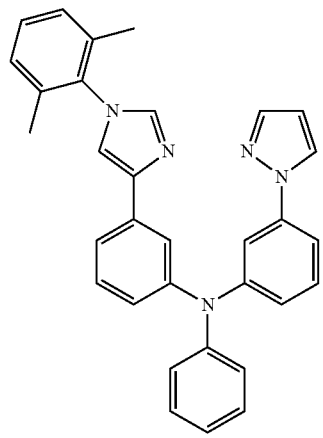

Synthesis of N-(3-(1H-pyrazol-1-yl)phenyl)-3-(1-(2,6-dimethylphenyl)-1H-imidazol-4-yl)-N-phenylaniline A 250 mL round-bottomed flask was charged with 3-(1-(2,6-dimethylphenyl)-1H-imidazol-4-yl)-N-phenylaniline (1.35 g, 3.98 mmol), 1-(3-bromophenyl)-1H-pyrazole (0.89 g, 3.98 mmol), and sodium tert-butoxide (0.459 g, 4.77 mmol) in toluene (80 mL). Pd$_2$(dba)$_3$ (0.091 g, 0.099 mmol) and dicyclohexyl(2',6'-dimethoxy-[1,1'-biphenyl]-2-yl)phosphine (0.163 g, 0.398 mmol) were added. The reaction flask was evacuated and backfilled with nitrogen twice. The reaction was stirred at reflux for 18 h, after which time the crude mixture was concentrated and purified using column chromatography, including elution with dichloromethane-hexane 1:1 followed by neat dichloromethane and finally a gradient of 1-5% ethyl acetate in dichloromethane. This gave 1.18 g (62%) of N-(3-(1H-pyrazol-1-yl)phenyl)-3-(1-(2,6-dimethylphenyl)-1H-imidazol-4-yl)-N-phenylaniline as a pale yellow foam.

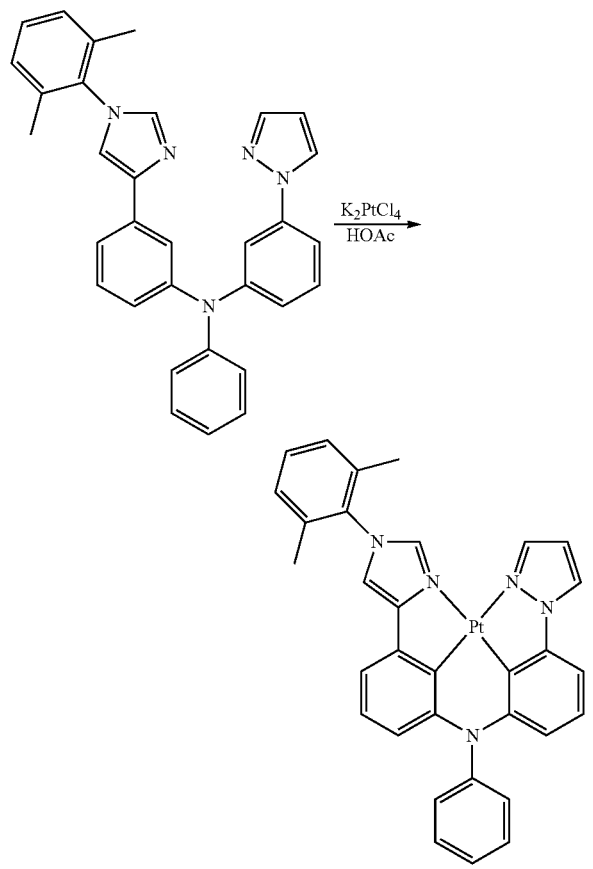

Synthesis of Compound 2'

N-(3-(1H-pyrazol-1-yl)phenyl)-3-(1-(2,6-dimethylphenyl)-1H-imidazol-4-yl)-N-phenylaniline (1.2 g, 2.5 mmol) and potassium tetrachloroplatinate (1.0 g, 2.5 mmol) were added to acetic acid (100 mL) and the mixture was degassed thoroughly with nitrogen before being heated to 130° C. (bath temperature) for 14 h. The reaction was cooled to room temperature, and 100 mL of water was added. After stirring for 20 minutes, the reaction mixture was filtered through a small bed of celite and washed with copious water and then MeOH. After drying, the solid was washed off the celite with DCM. The resulting filtrate was rotovapped to give 1.4 g of a yellow solid. The crude material was chromatographed on silica gel with 9:1 DCM:hexane to give 0.94 g of Compound 2' as a yellow solid (HPLC purity: 97.7%). The product was confirmed by NMR and LC/MS.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:
1. A compound having a formula is selected from the group consisting of:

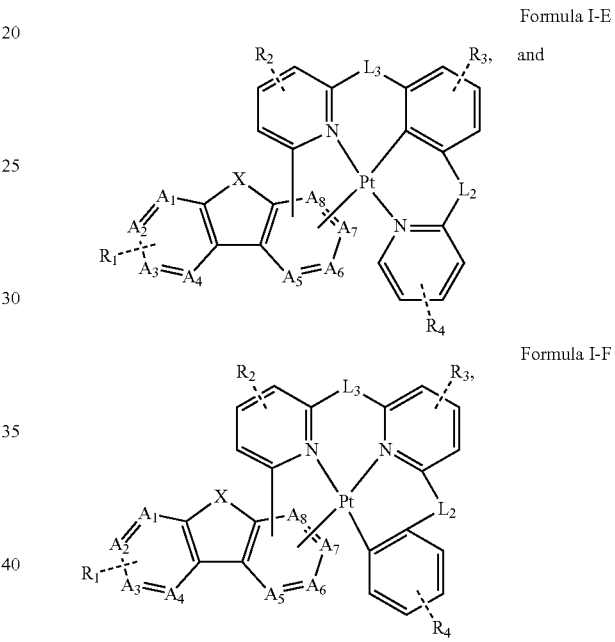

wherein X is selected from the group consisting of BR, NR, PR, O, S, Se, C=O, S=O, SO$_2$, CRR', SiRR', and GeRR';
wherein each of $A_1$, $A_2$, $A_3$, $A_4$, $A_5$, $A_6$, $A_7$, and $A_8$ independently comprise carbon or nitrogen;
wherein at most one of $A_1$, $A_2$, $A_3$, $A_4$ is nitrogen;
wherein at most one of $A_5$, $A_6$, $A_7$, $A_8$ is nitrogen, and the nitrogen is not bound to Pt or the adjacent pyridine ring;
wherein $R_1$, $R_2$, $R_3$, and $R_4$ each independently represent no substitutions up to the maximum possible substitutions;
wherein $R_1$ is optionally fused, $R_2$ is optionally fused, $R_3$ is optionally fused, and $R_4$ is optionally fused;
wherein $L_2$ is selected from the group consisting of BR, NR, PR, O, S, Se, C=O, S=O, SO$_2$, CRR', SiRR', and GeRR';
wherein $L_3$ is selected from the group consisting of a single bond, BR, NR, PR, O, S, Se, C=O, S=O, SO$_2$, CRR', SiRR', and GeRR';
wherein $R_3$ and $L_2$ or $R_4$ and $L_2$ are optionally linked to form a ring; and
wherein R, R', $R_1$, $R_2$, $R_3$, and $R_4$ are selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfonyl, sulfonyl, phosphino, and combinations thereof.

2. The compound of claim 1, wherein the compound has a neutral charge.

3. The compound of claim 1, wherein one of $A_1$, $A_2$, $A_3$, and $A_4$, is a nitrogen atom and/or one of $A_5$, $A_6$, $A_7$, and $A_8$ is a nitrogen atom.

4. The compound of claim 1, wherein $L_3$ is independently selected from the group consisting of O, S, and NR.

5. The compound of claim 4, wherein $L_3$ is NR, and R is phenyl or substituted phenyl.

6. The compound of claim 4, wherein $L_3$ is O.

7. The compound of claim 1, wherein X is selected from the group consisting of O, S, and NR.

8. The compound of claim 7, wherein X is O.

9. The compound of claim 1, wherein the compound has the structure of Formula I-E,

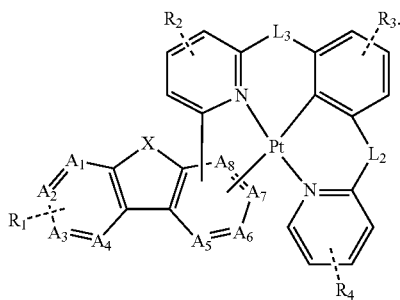

Formula I-E

10. The compound of claim 1, wherein the compound has the structure of Formula I-F,

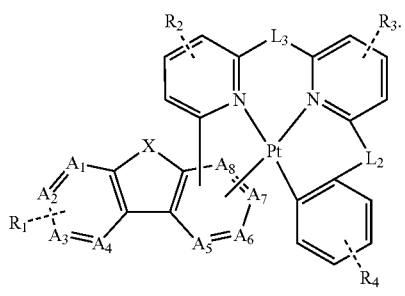

Formula I-F

11. A first device comprising a first organic light emitting device, comprising:
  an anode;
  a cathode; and
  an organic layer, disposed between the anode and the cathode, comprising a compound having a structure selected from the group consisting of:

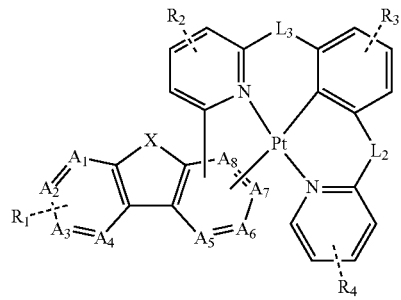

Formula I-E

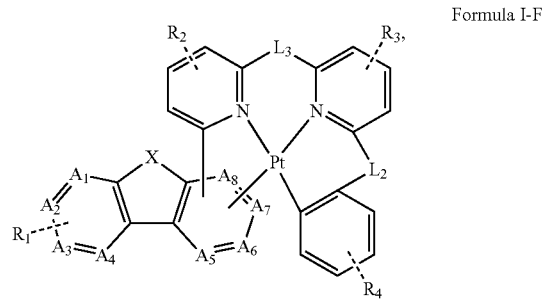

Formula I-F wherein X and Y are each independently is selected from the group consisting of BR, NR, PR, O, S, Se, C=O, S=O, $SO_2$, CRR', SiRR', and GeRR';

wherein each of $A_1$, $A_2$, $A_3$, $A_4$, $A_5$, $A_6$, $A_7$, and $A_8$ independently comprise carbon or nitrogen;

wherein at most one of $A_1$, $A_2$, $A_3$, $A_4$ is nitrogen;

wherein at most one of $A_5$, $A_6$, $A_7$, $A_8$ is nitrogen, and the nitrogen is not bound to Pt or the adjacent pyridine ring;

wherein $R_1$, $R_2$, $R_3$, and $R_4$ each independently represent no substitutions up to the maximum possible substitutions;

wherein $R_1$ is optionally fused, $R_2$ is optionally fused, $R_3$ is optionally fused, and $R_4$ is optionally fused;

wherein $L_2$ is selected from the group consisting of BR, NR, PR, O, S, Se, C=O, S=O, $SO_2$, CRR', SiRR', and GeRR';

wherein $L_3$ is selected from the group consisting of a single bond, BR, NR, PR, O, S, Se, C=O, S=O, $SO_2$, CRR', SiRR', and GeRR';

wherein $R_3$ and $L_2$ or $R_4$ and $L_2$ are optionally linked to form a ring; and wherein R, R', $R_1$, $R_2$, $R_3$, and $R_4$ are selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfonyl, sulfonyl, phosphino, and combinations thereof.

12. The compound of claim 1, wherein $L_2$ is selected from the group consisting of NR, O, and S.

13. The compound of claim 1, wherein L₃ is NR.
14. A compound selected from the group consisting of
Compound 61
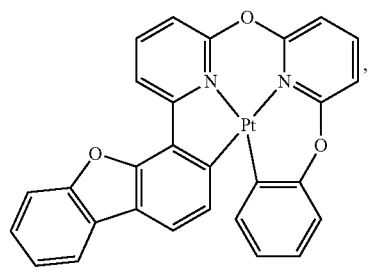
Compound 62
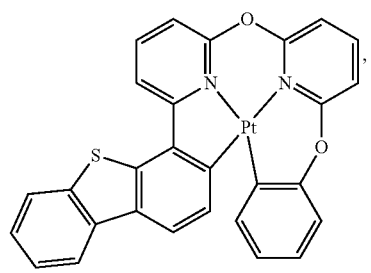
Compound 63
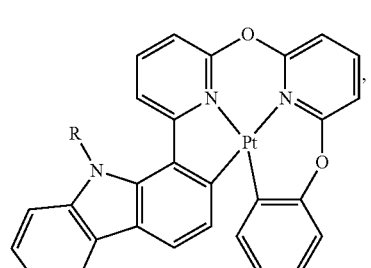
Compound 64
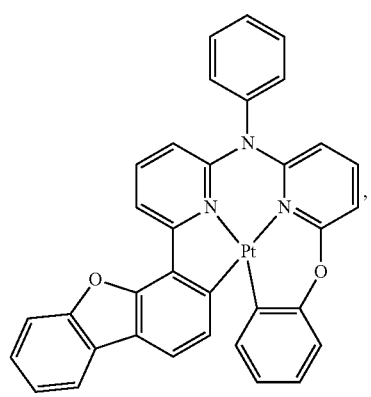
Compound 65
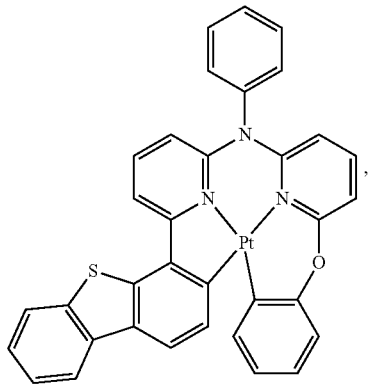
Compound 66
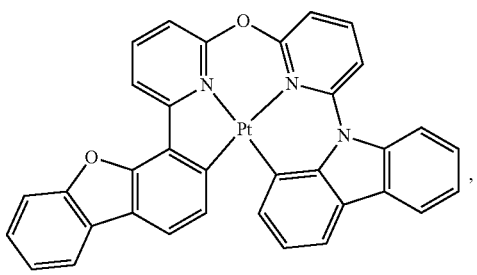
Compound 67
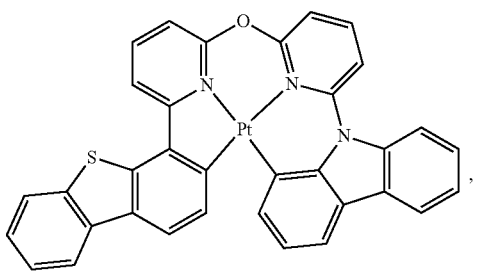
Compound 68

-continued
Compound 69
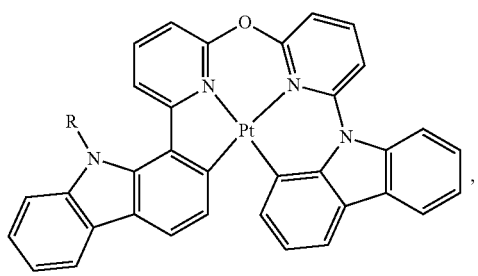
Compound 70
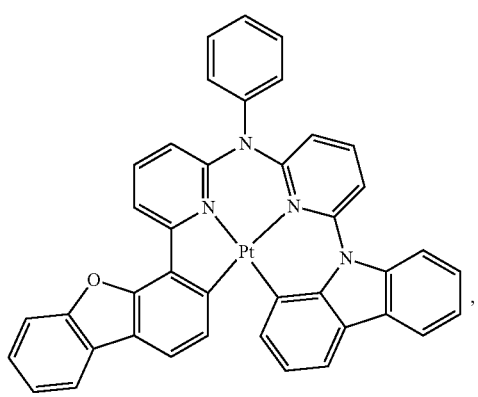
Compound 71
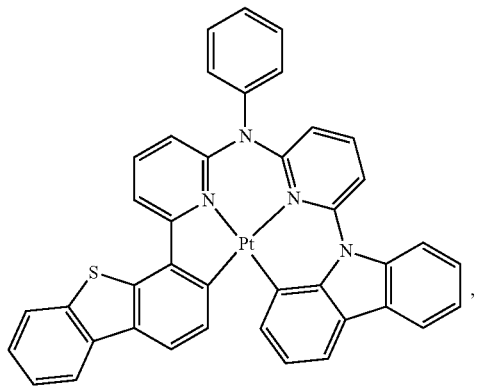
Compound 72
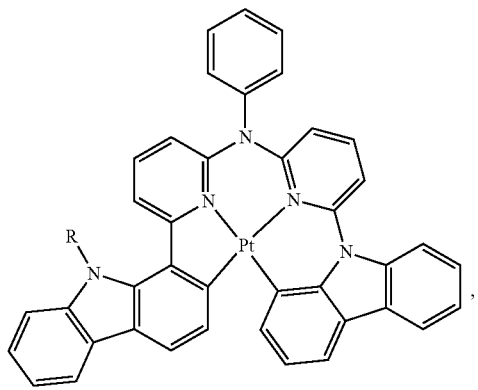
-continued
Compound 73
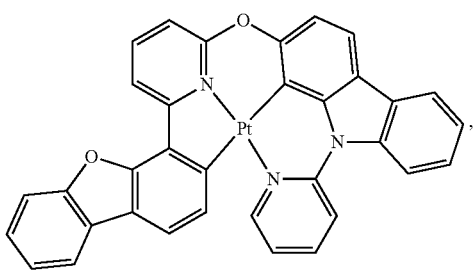
Compound 74
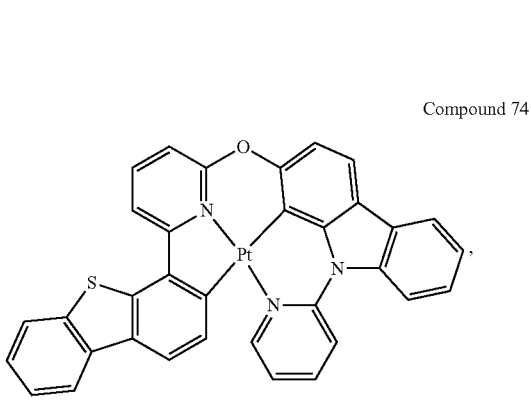
Compound 75
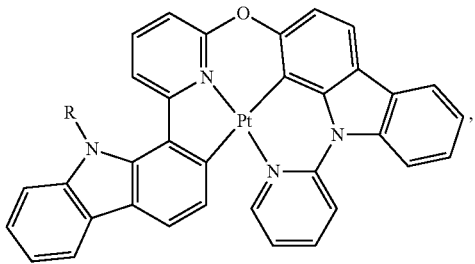
Compound 76
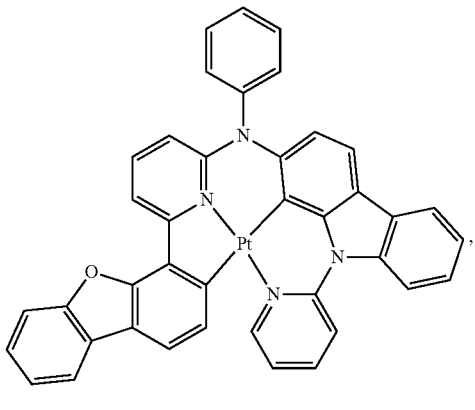

Compound 77
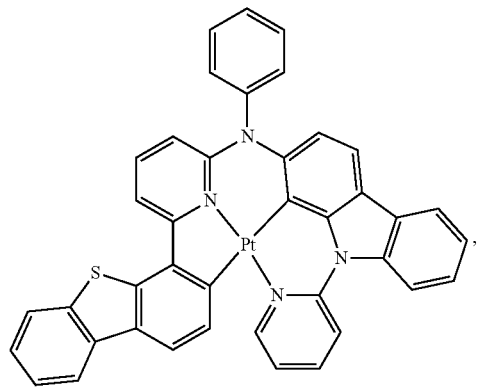
Compound 78
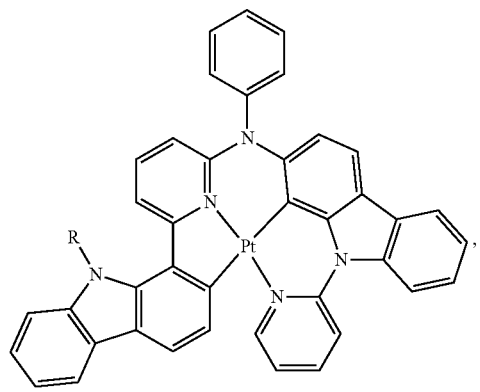
Compound 163
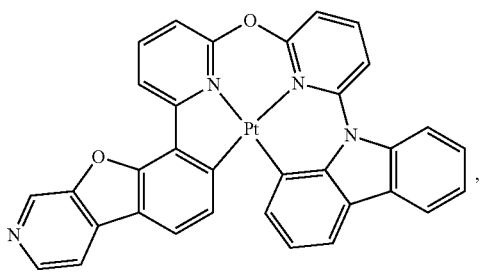
Compound 164
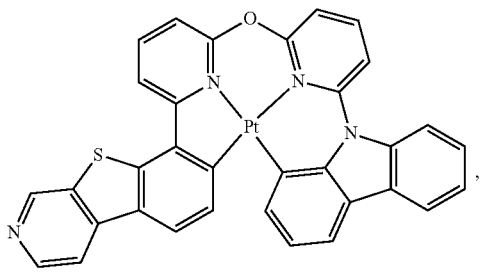
Compound 165
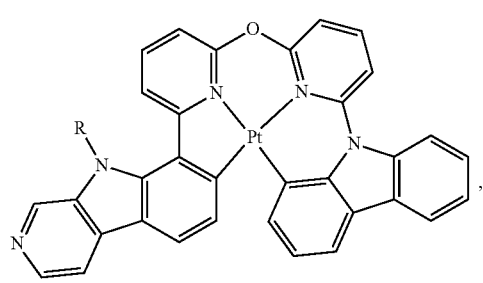
Compound 166
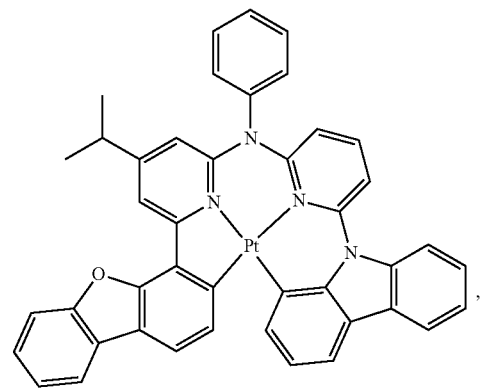
Compound 167
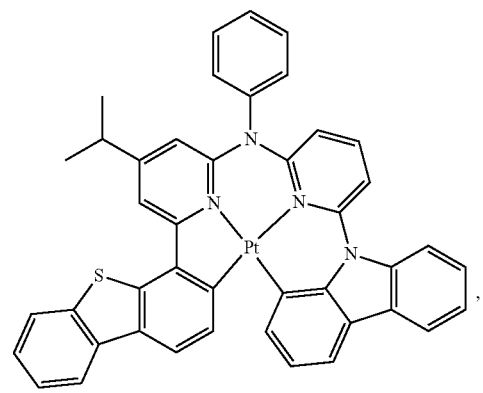
Compound 168
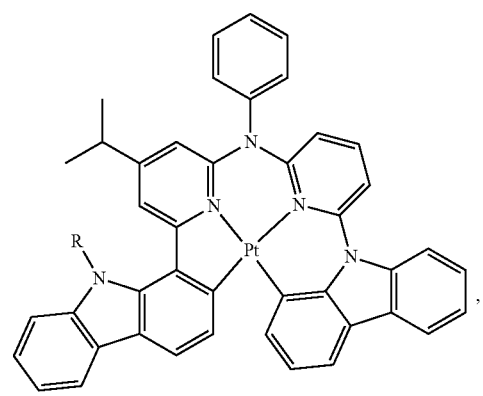

-continued
Compound 169
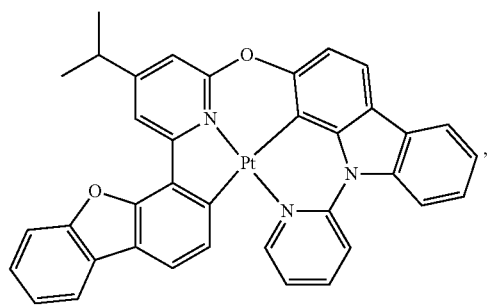
Compound 170
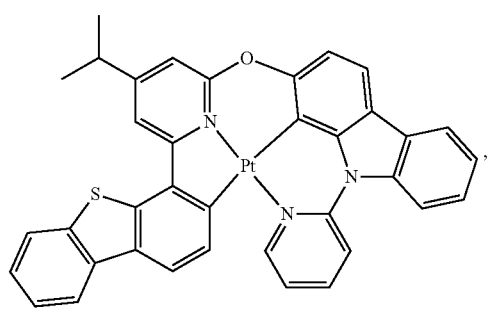
Compound 171
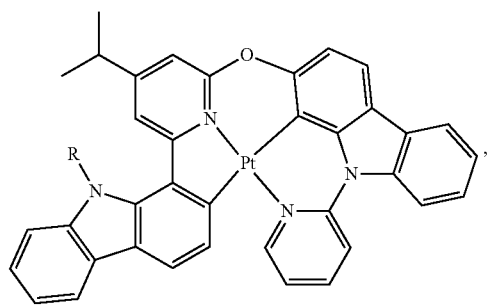
Compound 172
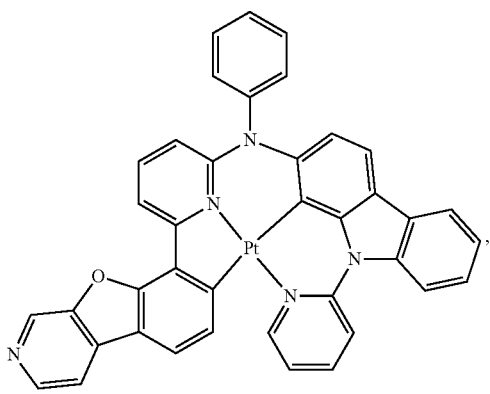
-continued
Compound 173
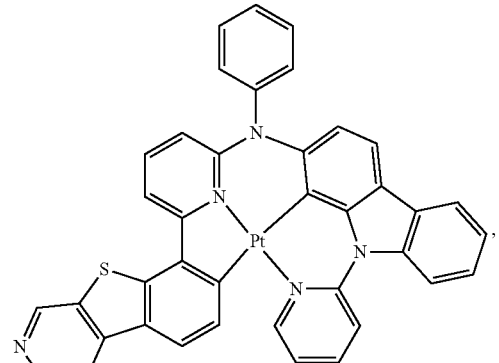
Compound 174
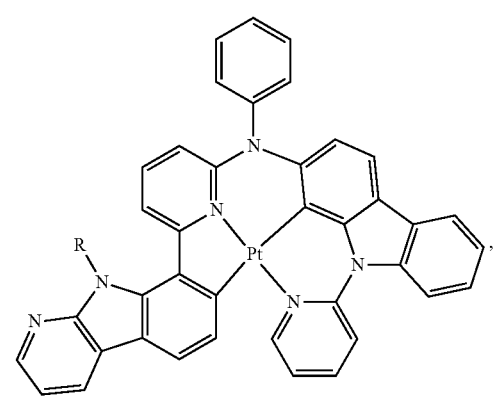
Compound 175
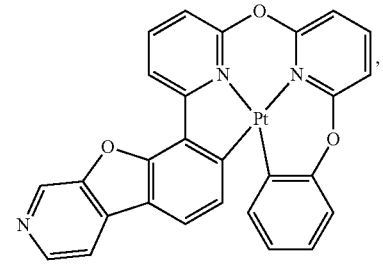
Compound 176
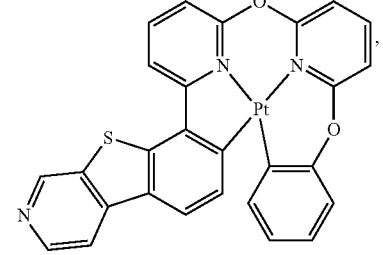
Compound 177
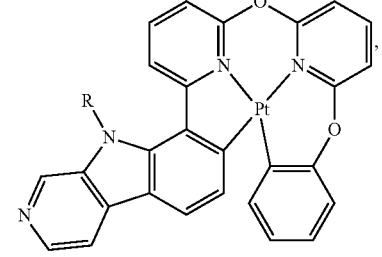

Compound 178
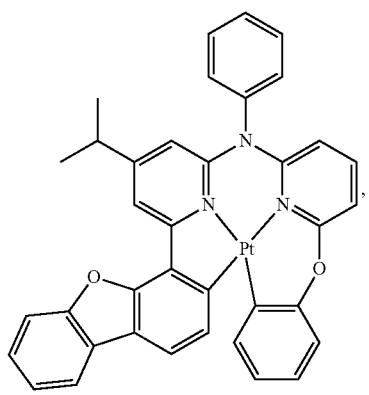
Compound 179
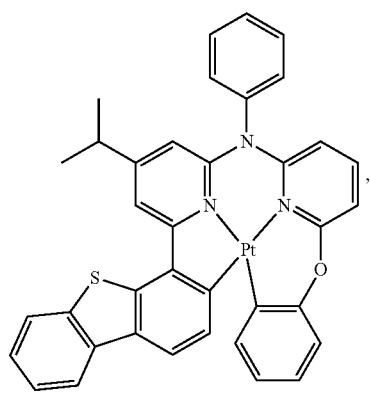
and
Compound 180
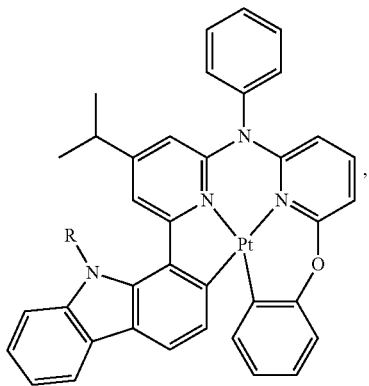
wherein R is independently selected from the group consisting of hydrogen, deuterium, halide, alkyl, cycloalkyl, heteroalkyl, arylalkyl, aryl, heteroaryl, acyl and combinations thereof.
15. The first device of claim 11, wherein the compound is selected from the group consisting of
Compound 61
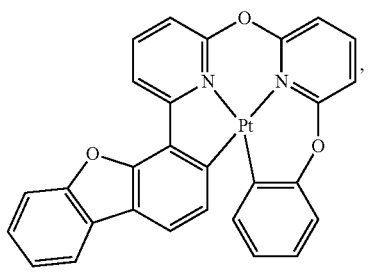
Compound 62
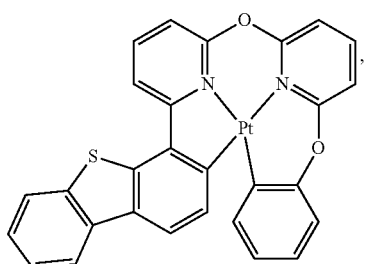
Compound 63
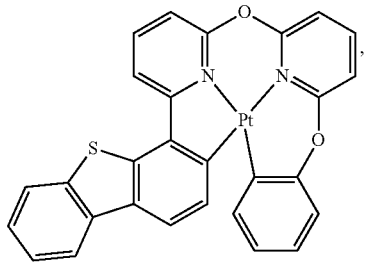
Compound 64
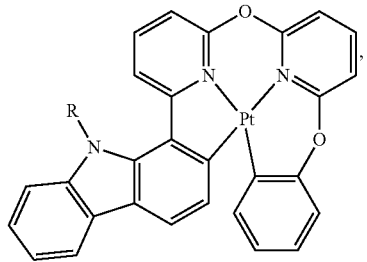
Compound 65
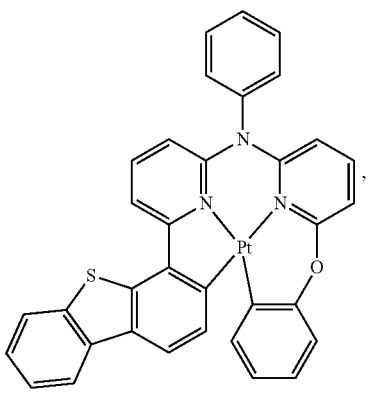

Compound 66
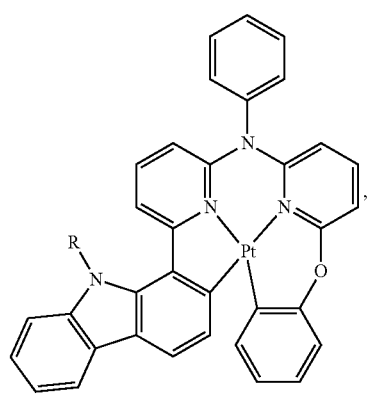
Compound 67
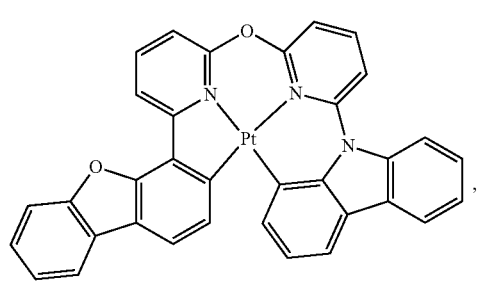
Compound 68
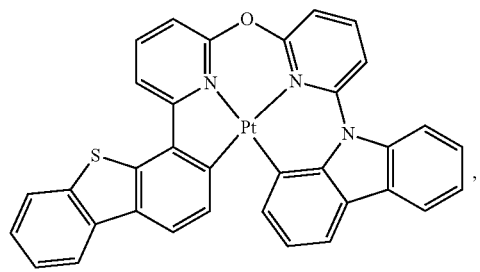
Compound 69
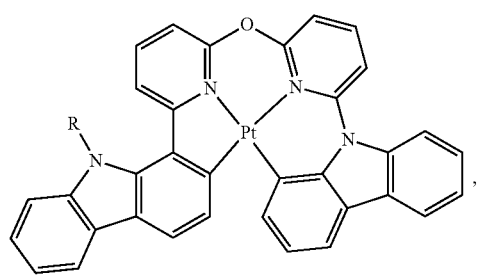
Compound 70
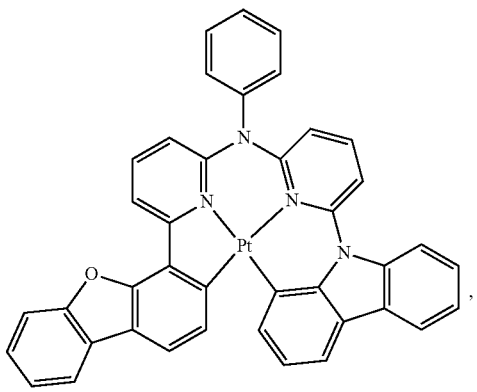
Compound 71
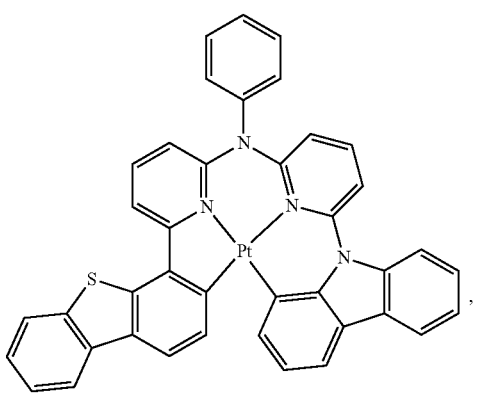
Compound 72
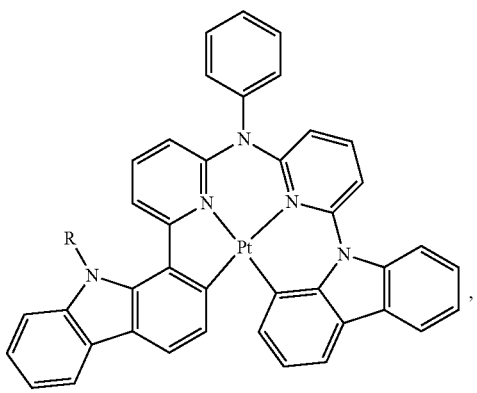
Compound 73
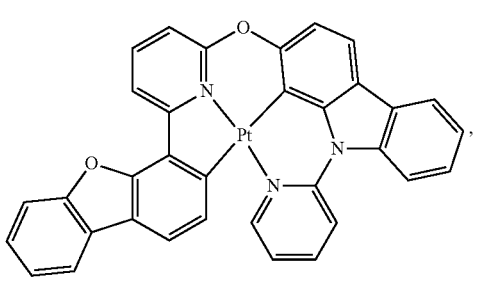

Compound 74
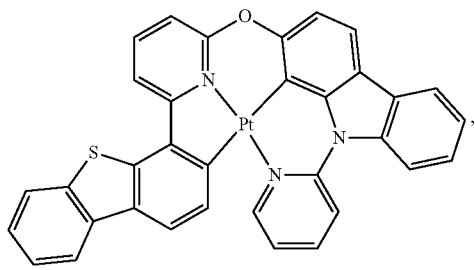
Compound 75
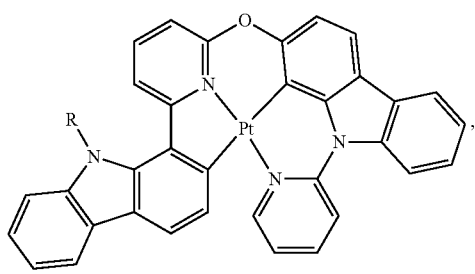
Compound 76
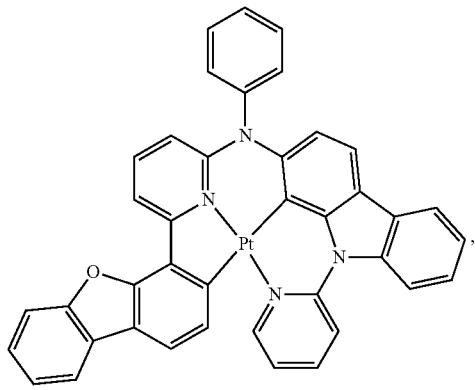
Compound 77
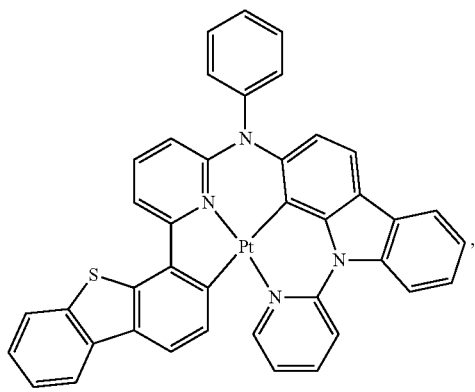
Compound 78
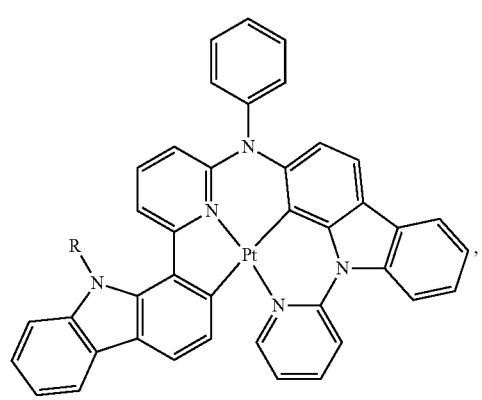
Compound 163
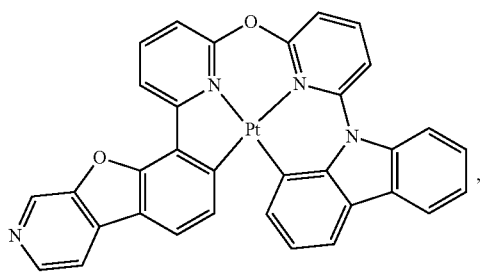
Compound 164
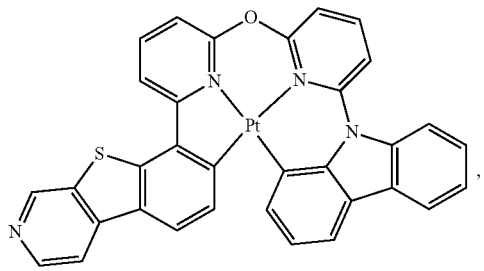
Compound 165
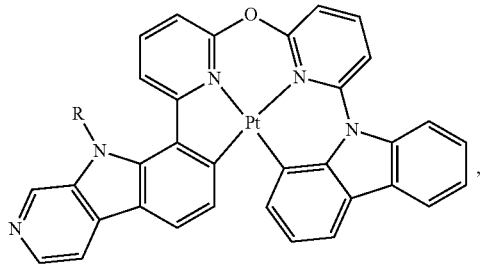

Compound 166
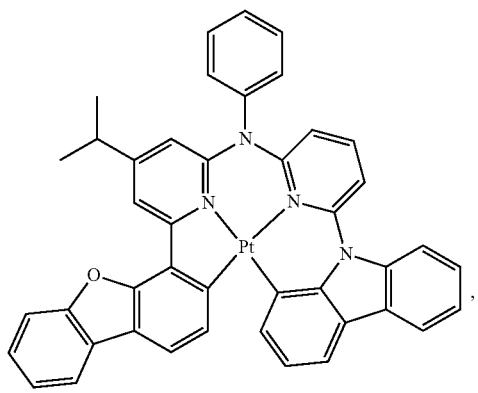
Compound 167
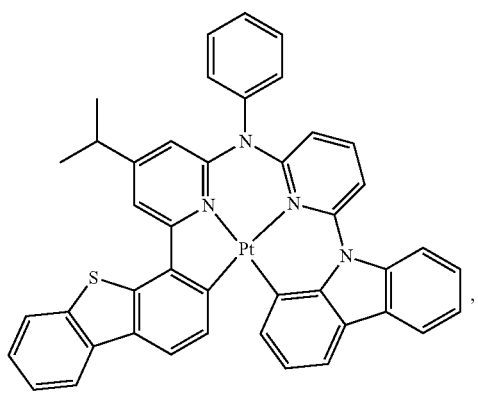
Compound 168
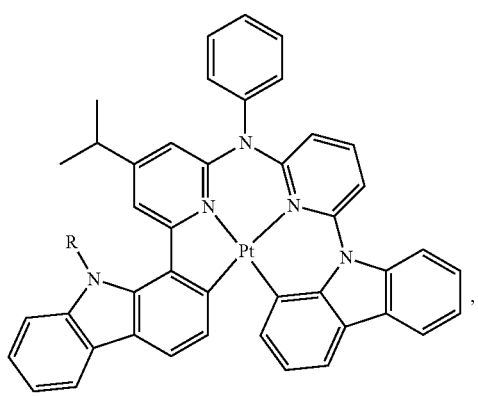
Compound 169
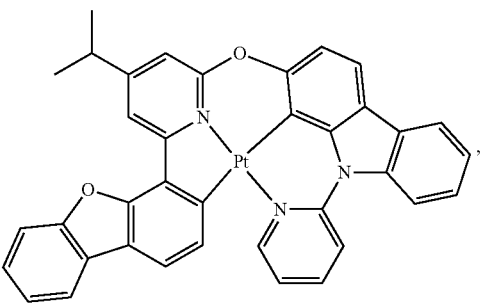
Compound 170
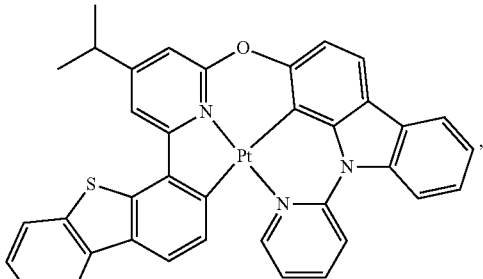
Compound 171
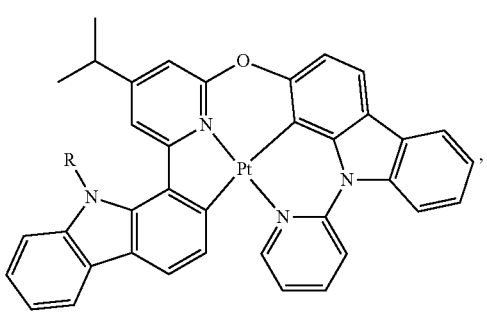
Compound 172
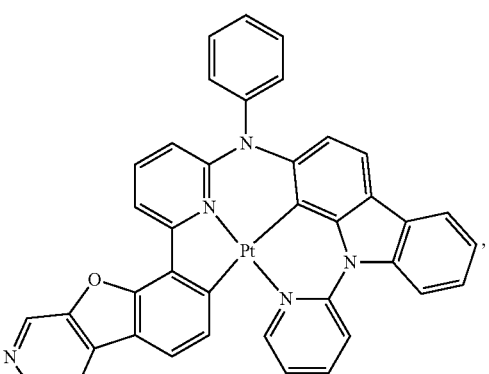
Compound 173
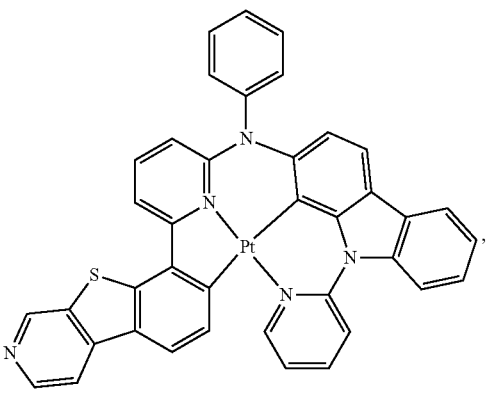

wherein R is independently selected from the group consisting of hydrogen, deuterium, halide, alkyl, cycloalkyl, heteroalkyl, arylalkyl, aryl, heteroaryl, acyl and combinations thereof.

16. The first device of claim 11, wherein the first device is selected from the group consisting of a consumer product, an organic light-emitting device, and a lighting panel.

17. The first device of claim 11, wherein the organic layer is an emissive layer and the compound is an emissive dopant or a non-emissive dopant.

18. The first device of claim 11, wherein the organic layer further comprises a host comprising a triphenylene containing benzo-fused thiophene or benzo-fused furan;
  wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CC_nH_{2n+1}$, $Ar_1$, $Ar_1-Ar_2$, and $C_nH_{2n}-Ar_1$;
  wherein n is from 1 to 10; and
  wherein $Ar_1$ and $Ar_2$ are independently selected from the group consisting of benzene, biphenyl, naphthalene, triphenylene, carbazole, and heteroaromatic analogs thereof.

19. The first device of claim 11, wherein the organic layer further comprises a host having the formula:
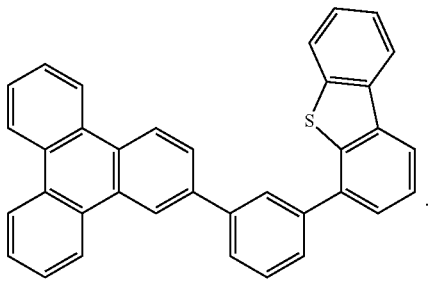 [SMILES: c1cc(-c2ccc3c4ccccc4c4ccccc4c3c2)cc(-c2cccc3c2sc2ccccc23)c1]
20. The first device of claim 11, wherein the organic layer further comprises a host selected from the group consisting of
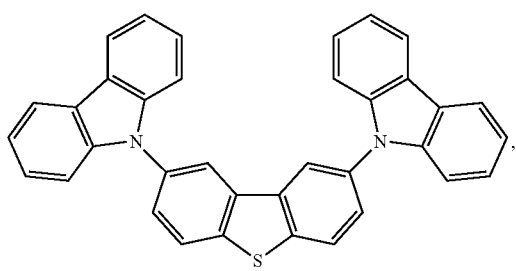
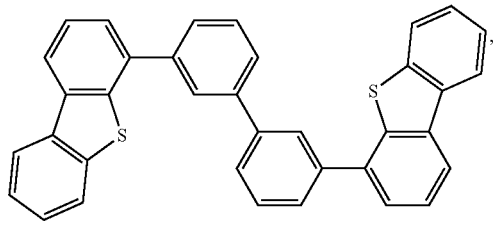
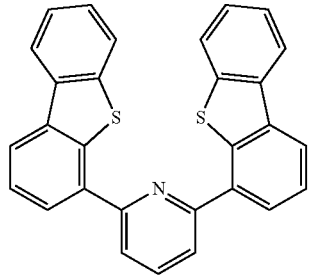
-continued
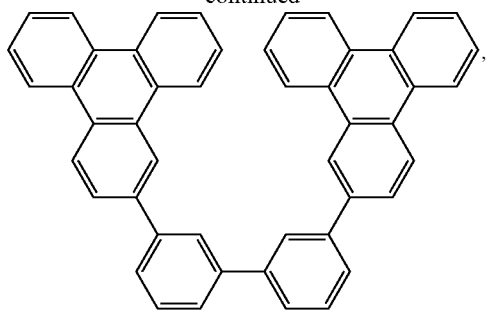
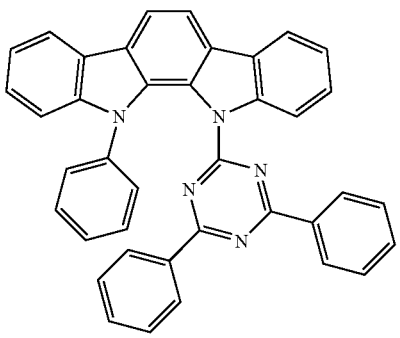
and combinations thereof.
* * * * *

UNITED STATES PATENT AND TRADEMARK OFFICE
CERTIFICATE OF CORRECTION

PATENT NO. : 9,783,564 B2
APPLICATION NO. : 13/588968
DATED : October 10, 2017
INVENTOR(S) : Gregg Kottas et al.

It is certified that error appears in the above-identified patent and that said Letters Patent is hereby corrected as shown below:

In the Specification

Column 10, Line 37, please delete the word "cycloakenyl" and insert --cycloalkenyl--

Column 13, Line 26, please delete the word "cycloakenyl" and insert --cycloalkenyl--

Column 198, Line 45, please delete the word "tittered" and insert --filtered--

Column 202, Line 25, please delete the word "fit" and insert --frit--

Column 204, Line 64, please delete "nit," and insert --mL--

Column 207, Line 42, please delete the word "tumor" and insert --mmol--

In the Claims

Claim 1, Column 211, Line 4, please delete the first instance of the word "sulfonyl" and insert --sulfinyl--

Signed and Sealed this
Twenty-fourth Day of April, 2018

Andrei Iancu
*Director of the United States Patent and Trademark Office*